US008409566B2

(12) United States Patent
Murphy et al.

(10) Patent No.: US 8,409,566 B2
(45) Date of Patent: Apr. 2, 2013

(54) THERAPEUTIC AND DIAGNOSTIC APPLICATIONS BASED ON THE ROLE OF THE CXCR-4 GENE IN TUMORIGENESIS

(75) Inventors: Gerald P. Murphy, Seattle, WA (US); Bridgette Murphy, legal representative, Seattle, WA (US); Alton L. Boynton, Kingston, WA (US); Anil Sehgal, Dublin, CA (US)

(73) Assignee: Northwest Biotherapeutics, Inc., Bethesda, MD (US)

( * ) Notice: Subject to any disclaimer, the term of this patent is extended or adjusted under 35 U.S.C. 154(b) by 329 days.

(21) Appl. No.: 12/367,308

(22) Filed: Feb. 6, 2009

(65) Prior Publication Data

US 2010/0062003 A1    Mar. 11, 2010

Related U.S. Application Data

(60) Division of application No. 10/985,324, filed on Nov. 9, 2004, now abandoned, which is a continuation of application No. 09/647,501, filed as application No. PCT/US99/07431 on Mar. 29, 1999, now Pat. No. 6,863,887.

(60) Provisional application No. 60/079,916, filed on Mar. 30, 1998, provisional application No. 60/104,656, filed on Oct. 16, 1998.

(51) Int. Cl.
*A61K 39/395* (2006.01)
*A61K 35/12* (2006.01)
(52) U.S. Cl. .............. 424/130.1; 424/178.1; 424/277.1
(58) Field of Classification Search .................. None
See application file for complete search history.

(56) References Cited

U.S. PATENT DOCUMENTS

| 4,958,009 A | | 9/1990 | Bjorn et al. | |
|---|---|---|---|---|
| 5,141,736 A | * | 8/1992 | Iwasa et al. | 530/387.3 |
| 5,543,503 A | | 8/1996 | Chuntharapai et al. | |
| 5,563,048 A | * | 10/1996 | Honjo et al. | 435/69.1 |
| 5,776,457 A | | 7/1998 | Lee et al. | |
| 5,798,229 A | | 8/1998 | Strittmatter et al. | |
| 5,840,856 A | | 11/1998 | Chuntharapai et al. | |
| 2001/0033841 A1 | * | 10/2001 | Luster et al. | 424/146.1 |
| 2005/0271665 A1 | * | 12/2005 | Mueller et al. | 424/145.1 |

FOREIGN PATENT DOCUMENTS

| EP | 1 072 273 A1 | 1/2001 |
|---|---|---|
| WO | WO 92/17497 A1 | 10/1992 |
| WO | WO 99/47158 | 9/1999 |
| WO | WO 99/50461 A1 | 10/1999 |
| WO | WO 00/09152 A1 | 2/2000 |

OTHER PUBLICATIONS

Sehgal et al J Sur Onco, 69:99-104, 1998.*
Shibuta et al, Int J Cancer, 73:656-662, 1997.*
Burger et al , Blood 107: 1761-1767, 2006.*
Banks, abstract, Neuroscience 2008, 9 (Suppl 3):S2 doi:10.1186/1471-2202-9-S3-S2.*
Wikstrand, Cancer and Metastasis Reviews 18: 451-464, 1999.*
Kryczek et al, Am J Physiol Cell Physiol 292: C987-995, 2007.*
Bleul et al., "The Lymphocyte Chemoattractant SDF-1 is a Ligand For LESTR/fusin and Blocks HIV-1 Entry," *Nature* 382:829-832 (1996).
Bogler et al., "The *p53* Gene and Its Role in Human Brain Tumors," *GLIA* 15: 308-327 (1995).
Broaddus et al., "Antiproliferative Effect of c-*myc* Antisense Phosphorothioate Oligodeoxynucleotides in Malignant Glioma Cells," *Neurosurgery* 41:908-915 (1997).
De Risi et al., "Use of a cDNA Microarray to Analyse Gene Expression Patterns in Human Cancer," *Nature, Genetics* 14:457 (1996).
Doranz et al., "Chemokine Receptors as Fusion Cofactors for Human Immunodeficiency Virus Type 1 (HIV-1)," *Immunol. Res.* 16:15 (1997).
Eibl et al., "Expression of Variant CD44 Epitopes in Human Astrocytic Brain Tumors," *J. of Neurooncol.*, U26:165-170 (1995).
Endres et al., "CD4-Independent Infection to HIV-2 Is Mediated by Fusion/CDCR4," *Cell* 87:745-756 (1996).
Engelhard et al., "Molecular Characterization of Glioblastoma Cell Differentiation," *Neurosurgery* 41:886-897 (1997).
Faillot et al., "A Phase I Study of an Anti-epidermal Growth Factor Receptor Monoclonal Antibody for the Treatment of Malignant Gliomas," *Neurosurgery*, 39:478-483 (1996).
Federsppiel et al., "Molecular Cloning of the cDNA and Chromosomal Localization of the Gene for a Putative Seven-Transmembrane Segment (7-TMS) Receptor Isolated from Human Spleen," *Genomics* 16:707-712 (1993).
Feng et al., "HIV-1 Entry Cofactor: Functional cDNA Cloning of a Seven-Transmembrane, G Protein-Coupled Receptor," *Science* 272:872-877 (1996).
Furnari et al., "Genetics and Malignant Progression of Human Brain Tumours," *Cancer Surv.* 25:233-275 (1995).
Haribabu et al., "Regulation of Human Chemokine Receptors CDCR4," *J. Biol. Chem.* 272:28726 (1997).
Huang et al., "Egr-1 Negatively Regulates Human Tumor Cell Growth via the DNA-binding Domain," *Cancer Research* 55:5054-5062 (1995).
Jung et al., "Increased Levels of $p21^{WAF1/Cip1}$ in Human Brain Tumors," *Oncogene* 11:2021-2028 (1995).
Laws et al., "Brain Tumors," *CA Cancer J. Clin.* 43:263-271 (1993).
Loetscher et al., "Cloning of a Human Seven-Transmembrane Domain Receptor, LESTR, That Is Highly Expressed in Leukocytes," *J. Biol. Chem.* 269:232-237 (1994).
Nagasawa et al., "Defects of B-Cell Lymphopoiesis and Bone-Marrow Myelopoesis in Mice Lacking the CDC Chemokine PBSF/SDF-1," *Nature* 382:635638 (1996).

(Continued)

*Primary Examiner* — Lei Yao
(74) *Attorney, Agent, or Firm* — Christensen O'Connor Johnson Kindness PLLC

(57) ABSTRACT

The present invention relates to the identification of a novel role of CXCR-4 in cell transformation and aberrant cellular proliferation. In particular, the present invention relates to the altered gene expression of CXCR-4 in a number of primary tumors and cell lines derived from tumors, in addition to, the altered gene expression of ligands for CXCR-4. Further, the present invention relates, in part, to the Applicant's surprising discovery that the inhibition of CXCR-4 gene expression or the inhibition of CXCR-4 activity in transformed cells reverses the transformed phenotype.

10 Claims, 25 Drawing Sheets

OTHER PUBLICATIONS

Nomura et al., "Molecular Cloning of cDNAs Encoding a LD78 Receptor and Putative Leukocyte Chemotactic Peptide Receptors," *Int. Immunol.* 5:1239-1249 (1993).

Oberlin et al., "The CXC Chemokine SDF-1 is the Ligand for LESTR/fusin and Prevents Infection by T-Cell-Line-Adapted HIV-1," *Nature* 382:833-835 (1996).

Parker et al., "Cancer Statistics, 1996," *CA Cancer J. Clin.* 46:5-28 (1996).

Previtali et al., "α6β4 and α6β1 Integrins in Astrocytomas and Other CNS Tumors," *J. Neuropathol. Exp. Neurol.* 55:456-465 (1996).

Sehgal et al., "Characterization of C4-2 as a Tumor-Suppressor Gene in Human Brain Tumors," *J. Surg. Oncol.* 64:102-108 (1997).

Sehgal et al., "Cloning, Sequence, and Developmental Expression Analysis of C4-2, a Potential Brain Tumor-Suppressor Gene," *J. Surg. Oncol.* 65:249-257 (1997).

Sehgal, "Application of the Differential Hybridizaion of Atlas™ Human Expression Arrays Technique in the Identification of Differentially Expressed Genes in Human Glioblastoma Multiforme Tumor Tissue," *J. Surg. Oncol.* 67:234-241 (1998).

Sehgal et al., "CXCR-4, a Chemokine Receptor, is Overexpressed in and Required for Proliferation of Glioblastoma Tumor Cells," *J. Surg. Oncol.* 69:99-104 (1998).

Sehgal et al., "Molecular Characterization of CXCR-4: A Potential Brain Tumor-Associated Gene," *J. Surg. Oncol.* 69:239-248 (1998).

Takano et al., "Concentration of Vascular Endothelial Growth Factor in the Serum and Tumor Tissue of Brain Tumor Patients," *Cancer Res.* 56:2185-2190 (1996).

Tsuzuki et al., "Alterations of Retinoblastoma, p53, p16(CDKN2), and p15 Genes in Human Astrocytomas," *Cancer* 78:287-293 (1996).

vonDiemling et al., "Molecular Pathways in the Formation of Gliomas," *GLIA* 15:328-338 (1995).

Yamamoto et al., "Differential Expression of Membrane-Type Matrix Metalloproteinase and Its Correlation with Gelatinase A Activation in Human Malignant Brain Tumors in Vivo and in Vitro," *Cancer Res.* 56: 384-392 (1996).

Meier, R., et al., "The Chemokine Receptor CXCR4 Strongly Promotes Neuroblastoma Primary Tumour and Metastatic Growth, but Not Invasion," PLoS ONE 2(10):e1016, Oct. 2007.

Communication Pursuant to Article 94(3) EPC mailed Feb. 15, 2012, issued in corresponding European Application No. 10184637, filed Mar. 29, 1999, 4 pages.

* cited by examiner

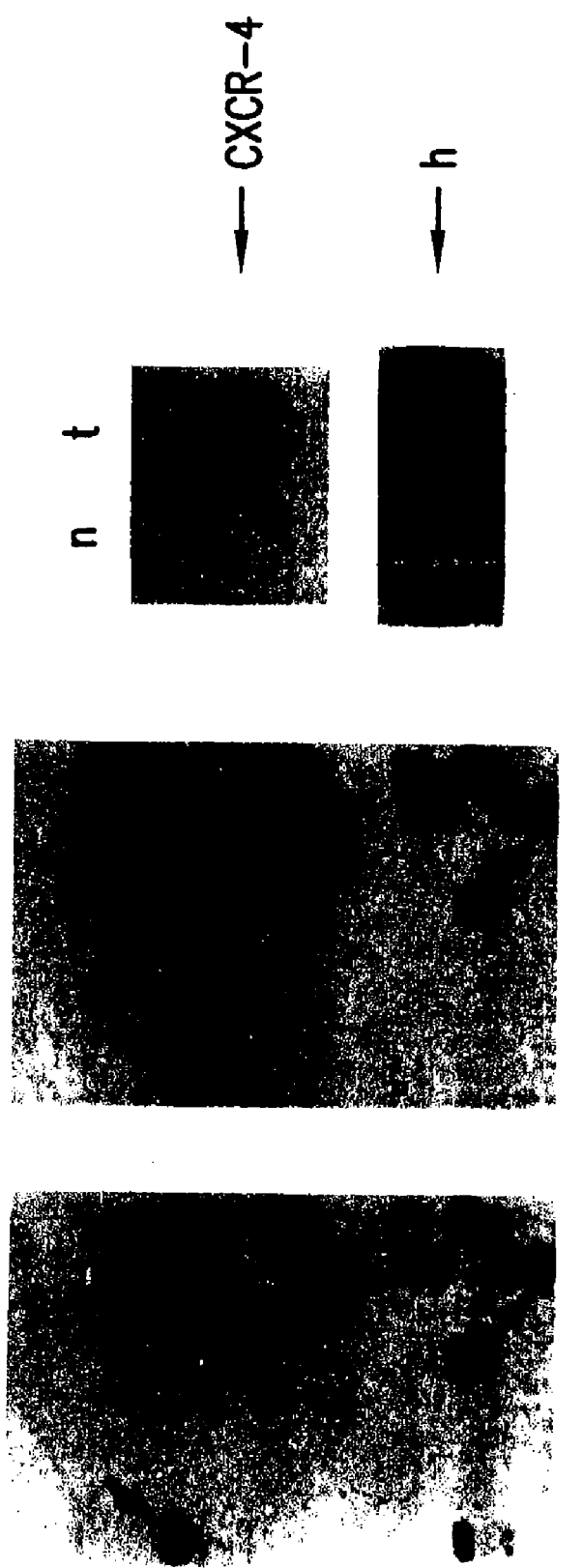

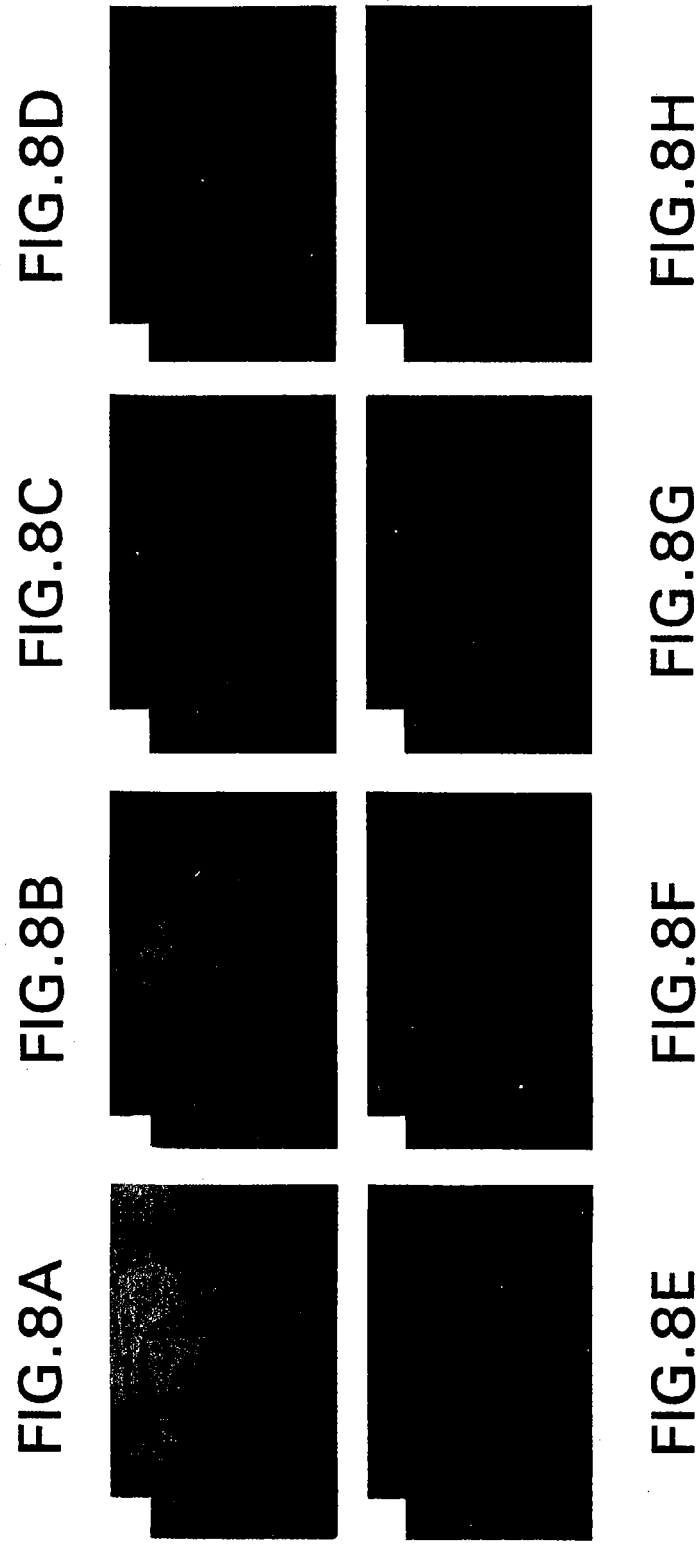

   
FIG.8I  FIG.8J  FIG.8K  FIG.8L
  
FIG.8M  FIG.8N  FIG.8O  FIG.8P FIG.12A
FIG.12B
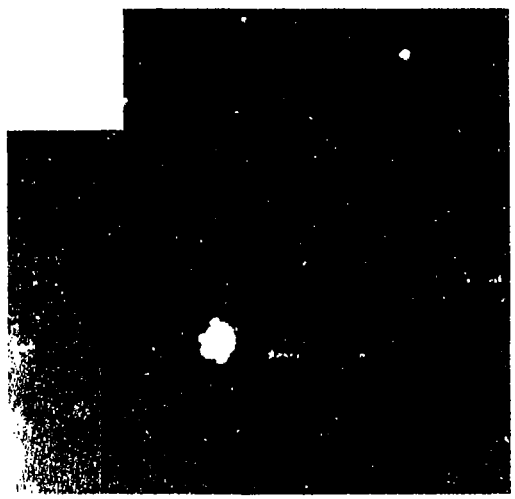
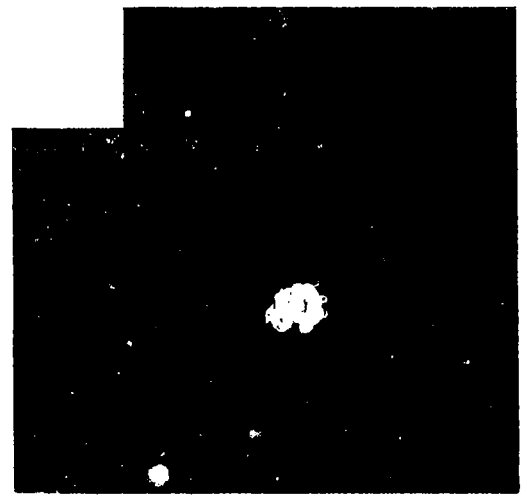
FIG.12C
FIG.12D

```
ATG GAG GGG ATC AGT ATA TAC ACT TCA GAT AAC TAC ACC GAG GAA ATG      48
Met Glu Gly Ile Ser Ile Tyr Thr Ser Asp Asn Tyr Thr Glu Glu Met
 1               5                  10                  15

GGC TCA GGG GAC TAT GAC TCC ATG AAG GAA CCC TGT TTC CGT GAA GAA      96
Gly Ser Gly Asp Tyr Asp Ser Met Lys Glu Pro Cys Phe Arg Glu Glu
                 20                  25                  30

AAT GCT AAT TTC AAT AAA ATC TTC CTG CCC ACC ATC TAC TCC ATC ATC     144
Asn Ala Asn Phe Asn Lys Ile Phe Leu Pro Thr Ile Tyr Ser Ile Ile
             35                  40                  45

TTC TTA ACT GGC ATT GTG GGC AAT GGA TTG GTC ATC CTG GTC ATG GGT     192
Phe Leu Thr Gly Ile Val Gly Asn Gly Leu Val Ile Leu Val Met Gly
         50                  55                  60

TAC CAG AAG AAA CTG AGA AGC ATG ACG GAC AAG TAC AGG CTG CAC CTG     240
Tyr Gln Lys Lys Leu Arg Ser Met Thr Asp Lys Tyr Arg Leu His Leu
65                  70                  75                  80

TCA GTG GCC GAC CTC CTC TTT GTC ATC ACG CTT CCC TTC TGG GCA GTT     288
Ser Val Ala Asp Leu Leu Phe Val Ile Thr Leu Pro Phe Trp Ala Val
                     85                  90                  95

GAT GCC GTG GCA AAC TGG TAC TTT GGG AAC TTC CTA TGC AAG GCA GTC     336
Asp Ala Val Ala Asn Trp Tyr Phe Gly Asn Phe Leu Cys Lys Ala Val
                100                 105                 110

CAT GTC ATC TAC ACA GTC AAC CTC TAC AGC AGT GTC CTC ATC CTG GCC     384
His Val Ile Tyr Thr Val Asn Leu Tyr Ser Ser Val Leu Ile Leu Ala
             115                 120                 125

TTC ATC AGT CTG GAC CGC TAC CTG GCC ATC GTC CAC GCC ACC AAC AGT     432
Phe Ile Ser Leu Asp Arg Tyr Leu Ala Ile Val His Ala Thr Asn Ser
         130                 135                 140

CAG AGG CCA AGG AAG CTG TTG GCT GAA AAG GTG GTC TAT GTT GGC GTC     480
Gln Arg Pro Arg Lys Leu Leu Ala Glu Lys Val Val Tyr Val Gly Val
145                 150                 155                 160
```

FIG. 14A

```
TGG ATC CCT GCC CTC CTG CTG ACT ATT CCC GAC TTC ATC TTT GCC AAC    528
Trp Ile Pro Ala Leu Leu Leu Thr Ile Pro Asp Phe Ile Phe Ala Asn
            165                 170                 175
GTC AGT GAG GCA GAT GAC AGA TAT ATC TGT GAC CGC TTC TAC CCC AAT    576
Val Ser Glu Ala Asp Asp Arg Tyr Ile Cys Asp Arg Phe Tyr Pro Asn
            180                 185                 190
GAC TTG TGG GTG GTT GTG TTC CAG TTT CAG CAC ATC ATG GTT GGC CTT    624
Asp Leu Trp Val Val Val Phe Gln Phe Gln His Ile Met Val Gly Leu
            195                 200                 205
ATC CTG CCT GGT ATT GTC ATC CTG TCC TGC TAT TGC ATT ATC ATC TCC    672
Ile Leu Pro Gly Ile Val Ile Leu Ser Cys Tyr Cys Ile Ile Ile Ser
            210                 215                 220
AAG CTG TCA CAC TCC AAG GGC CAC CAG AAG CGC AAG GCC CTC AAG ACC    720
Lys Leu Ser His Ser Lys Gly His Gln Lys Arg Lys Ala Leu Lys Thr
225                 230                 235                 240
ACA GTC ATC CTC ATC CTG GCT TTC TTC GCC TGT TGG CTG CCT TAC TAC    768
Thr Val Ile Leu Ile Leu Ala Phe Phe Ala Cys Trp Leu Pro Tyr Tyr
            245                 250                 255
ATT GGG ATC AGC ATC GAC TCC TTC ATC CTC CTG GAA ATC ATC AAG CAA    816
Ile Gly Ile Ser Ile Asp Ser Phe Ile Leu Leu Glu Ile Ile Lys Gln
            260                 265                 270
GGG TGT GAG TTT GAG AAC ACT GTG CAC AAG TGG ATT TCC ATC ACC GAG    864
Gly Cys Glu Phe Glu Asn Thr Val His Lys Trp Ile Ser Ile Thr Glu
            275                 280                 285
GCC CTA GCT TTC TTC CAC TGT TGT CTG AAC CCC ATC CTC TAT GCT TTC    912
Ala Leu Ala Phe Phe His Cys Cys Leu Asn Pro Ile Leu Tyr Ala Phe
            290                 295                 300
CTT GGA GCC AAA TTT AAA ACC TCT GCC CAG CAC GCA CTC ACC TCT GTG    960
Leu Gly Ala Lys Phe Lys Thr Ser Ala Gln His Ala Leu Thr Ser Val
305                 310                 315                 320
AGC AGA GGG TCC AGC CTC AAG ATC CTC TCC AAA GGA AAG CGA GGT GGA   1008
Ser Arg Gly Ser Ser Leu Lys Ile Leu Ser Lys Gly Lys Arg Gly Gly
            325                 330                 335
CAT TCA TCT GTT TCC ACT GAG TCT GAG TCT TCA AGT TTT CAC TCC AGC T 1057
His Ser Ser Val Ser Thr Glu Ser Glu Ser Ser Ser Phe His Ser Ser
            340                 345                 350
AA                                                                1059
```

FIG. 14B

```
TCTCCGTCAG CCGCATTGCC CGCTCGGCGT CCGGCCCCCG ACCCGTGCTC GTCCGCCCGC    60
CCGCCCGCCC GCCCGCGCC ATG AAC GCC AAG GTC GTG GTC GTG CTG GTC CTC   112
                    Met Asn Ala Lys Val Val Val Val Leu Val Leu
                     1               5                  10
GTG CTG ACC GCG CTC TGC CTC AGC GAC GGG AAG CCC GTC AGC CTG AGC   160
Val Leu Thr Ala Leu Cys Leu Ser Asp Gly Lys Pro Val Ser Leu Ser
             15                  20                  25

TAC AGA TGC CCA TGC CGA TTC TTC GAA AGC CAT GTT GCC AGA GCC AAC   208
Tyr Arg Cys Pro Cys Arg Phe Phe Glu Ser His Val Ala Arg Ala Asn
             30                  35                  40

GTC AAG CAT CTC AAA ATT CTC AAC ACT CCA AAC TGT GCC CTT CAG ATT   256
Val Lys His Leu Lys Ile Leu Asn Thr Pro Asn Cys Ala Leu Gln Ile
             45                  50                  55

GTA GCC CGG CTG AAG AAC AAC AAC AGA CAA GTG TGC ATT GAC CCG AAG   304
Val Ala Arg Leu Lys Asn Asn Asn Arg Gln Val Cys Ile Asp Pro Lys
 60              65                  70                  75

CTA AAG TGG ATT CAG GAG TAC CTG GAG AAA GCT TTA AAC AAG TAAGCACAA  355
Leu Lys Trp Ile Gln Glu Tyr Leu Glu Lys Ala Leu Asn Lys
                 80                  85

CAGCCAAAAA GGACTTTCCG CTAGACCCAC TCGAGGAAAA CTAAAACCTT GTGAGAGATG   415
AAAGGGCAAA GACGTGGGGG AGGGGGCCTT AACCATGAGG ACCAGGTGTG TGTGTGGGGT   475
GGGCACATTG ATCTGGGATC GGGCCTGAGG TTTGCAGCAT TTAGACCCTG CATTTATAGC   535
ATACGGTATG ATATTGCAGC TTATATTCAT CCATGCCCTG TACCTGTGCA CGTTGGAACT   595
TTTATTACTG GGGTTTTTCT AAGAAAGAAA TTGTATTATC AACAGCATTT TCAAGCAGTT   655
AGTTCCTTCA TGATCATCAC AATCATCATC ATTCTCATTC TCATTTTTTA AATCAACGAG   715
TACTTCAAGA TCTGAATTTG GCTTGTTTGG AGCATCTCCT CTGCTCCCCT GGGGAGTCTG   775
GCACAGTCA GGTGGTGGCT TAACAGGGAG CTGGAAAAAG TGTCCTTTCT TCAGACACTG   835
AGGCTCCCGC AGCAGCGCCC CTCCCAAGAG GAAGGCCTCT GTGGCACTCA GATACCGACT   895
GGGGCTGGGG CGCCGCCACT GCCTTCACCT CCTCTTTCAA ACCTCAGTGA TTGGCTCTGT   955
GGGCTCCATG TAGAAGCCAC TATTACTGGG ACTGTCTCAG AGACCCCTCT CCCAGCTATT  1015
CCTACTCTCT CCCCGACTCC GAGAGCATGC TTAATCTTGC TTCTGCTTCT CATTTCTGTA  1075
GCCTGATCAG CGCCGCACCA GCCGGGAAGA GGGTGATTGC TGGGGCTCGT GCCCTGCATC  1135
CCTCTCCTCC CAGGGCCTGC CCCACAGCTC GGGCCCTCTG TGAGATCCGT CTTTGGCCTC  1195
CTCCAGAATG GAGCTGGCCC TCTCCTGGGG ATGTGTAATG GTCCCCCTGC TTACCCGCAA  1255
```

FIG. 15A

```
AAGACAAGTC TTTACAGAAT CAAATGCAAT TTTAAATCTG AGAGCTCGCT TGAGTGACTG  1315
GGTTTGTGAT TGCCTCTGAA GCCTATGTAT GCCATGGAGG CACTAACAAA CTCTGAGGTT  1375
TCCGAAATCA GAAGCGAAAA AATCAGTGAA TAAACCATCA TCTTGCCACT ACCCCCTCCT  1435
GAAGCCACAG CAGGGGTTCA GGTTCCAATC AGAACTGTTG GCAAGGTGAC ATTTCCATGC  1495
ATAGATGCGA TCCACAGAAG GTCCTGGTGG TATTTGTAAC TTTTTGCAAG GCATTTTTTT  1555
ATATATATTT TTGTGCACAT TTTTTTTTAC GATTCTTTAG AAAACAAATG TATTTCAAAA  1615
TATATTTATA GTCGAACAAG TCATATATAT GAATGAGAGC CATATGAATG TCAGTAGTTT  1675
ATACTTCTCT ATTATCTCAA ACTACTGGCA ATTTGTAAAG AAATATATAT GATATATAAA  1735
TGTGATTGCA GCTTTTCAAT GTTAGCCACA GTGTATTTTT TCACTTGTAC TAAAATTGTA  1795
TCAAATGTGA CATTATATGC ACTAGCAATA AAATGCTAAT TGTTTCATGG TA           1847
```

FIG. 15B

SEQUENCE LISTING

<160> NUMBER OF SEQ ID NOS: 28

<210> SEQ ID NO 1
<211> LENGTH: 1059
<212> TYPE: DNA
<213> ORGANISM: Homo sapiens

<400> SEQUENCE: 1

| | | | | | |
|---|---|---|---|---|---|
| atggagggga | tcagtatata | cacttcagat | aactacaccg | aggaaatggg | ctcaggggac | 60 |
| tatgactcca | tgaaggaacc | ctgtttccgt | gaagaaaatg | ctaatttcaa | taaaatcttc | 120 |
| ctgcccacca | tctactccat | catcttctta | actggcattg | tgggcaatgg | attggtcatc | 180 |
| ctggtcatgg | gttaccagaa | gaaactgaga | agcatgacgg | acaagtacag | gctgcacctg | 240 |
| tcagtggccg | acctcctctt | tgtcatcacg | cttcccttct | gggcagttga | tgccgtggca | 300 |
| aactggtact | tgggaactt | cctatgcaag | gcagtccatg | tcatctacac | agtcaacctc | 360 |
| tacagcagtg | tcctcatcct | ggccttcatc | agtctggacc | gctacctggc | catcgtccac | 420 |
| gccaccaaca | gtcagaggcc | aaggaagctg | ttggctgaaa | aggtggtcta | tgttggcgtc | 480 |
| tggatccctg | ccctcctgct | gactattccc | gacttcatct | ttgccaacgt | cagtgaggca | 540 |
| gatgacagat | atatctgtga | ccgcttctac | cccaatgact | tgtgggtggt | tgtgttccag | 600 |
| tttcagcaca | tcatggttgg | ccttatcctg | cctggtattg | tcatcctgtc | ctgctattgc | 660 |
| attatcatct | ccaagctgtc | acactccaag | ggccaccaga | agcgcaaggc | cctcaagacc | 720 |
| acagtcatcc | tcatcctggc | tttcttcgcc | tgttggctgc | cttactacat | tgggatcagc | 780 |
| atcgactcct | tcatcctcct | ggaaatcatc | aagcaagggt | gtgagtttga | gaacactgtg | 840 |
| cacaagtgga | tttccatcac | cgaggcccta | gctttcttcc | actgttgtct | gaaccccatc | 900 |
| ctctatgctt | tccttggagc | caaatttaaa | acctctgccc | agcacgcact | cacctctgtg | 960 |
| agcagagggt | ccagcctcaa | gatcctctcc | aaaggaaagc | gaggtggaca | ttcatctgtt | 1020 |
| tccactgagt | ctgagtcttc | aagttttcac | tccagctaa | | | 1059 |

<210> SEQ ID NO 2
<211> LENGTH: 352
<212> TYPE: PRT
<213> ORGANISM: Homo sapiens

<400> SEQUENCE: 2

```
Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110
```

```
His Val Ile Tyr Thr Val Asn Leu Tyr Ser Ser Val Leu Ile Leu Ala
    115                 120                 125
Phe Ile Ser Leu Asp Arg Tyr Leu Ala Ile Val His Ala Thr Asn Ser
130                 135                 140
Gln Arg Pro Arg Lys Leu Leu Ala Glu Lys Val Val Tyr Val Gly Val
145                 150                 155                 160
Trp Ile Pro Ala Leu Leu Leu Thr Ile Pro Asp Phe Ile Phe Ala Asn
                165                 170                 175
Val Ser Glu Ala Asp Asp Arg Tyr Ile Cys Asp Arg Phe Tyr Pro Asn
            180                 185                 190
Asp Leu Trp Val Val Phe Gln Phe Gln His Ile Met Val Gly Leu
        195                 200                 205
Ile Leu Pro Gly Ile Val Ile Leu Ser Cys Tyr Cys Ile Ile Ser
    210                 215                 220
Lys Leu Ser His Ser Lys Gly His Gln Lys Arg Lys Ala Leu Lys Thr
225                 230                 235                 240
Thr Val Ile Leu Ile Leu Ala Phe Phe Ala Cys Trp Leu Pro Tyr Tyr
                245                 250                 255
Ile Gly Ile Ser Ile Asp Ser Phe Ile Leu Leu Glu Ile Ile Lys Gln
            260                 265                 270
Gly Cys Glu Phe Glu Asn Thr Val His Lys Trp Ile Ser Ile Thr Glu
        275                 280                 285
Ala Leu Ala Phe Phe His Cys Cys Leu Asn Pro Ile Leu Tyr Ala Phe
    290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Phe His Ser Ser
            340                 345                 350

<210> SEQ ID NO 3
<211> LENGTH: 1847
<212> TYPE: DNA
<213> ORGANISM: Homo sapiens

<400> SEQUENCE: 3
tctccgtcag ccgcattgcc cgctcggcgt ccggccccg acccgtgctc gtccgcccgc      60
ccgcccgccc gccgcgcca tgaacgccaa ggtcgtggtc gtgctggtcc tcgtgctgac     120
cgcgctctgc ctcagcgacg ggaagcccgt cagcctgagc tacagatgcc atgccgatt    180 cttcgaaagc catgttgcca gagccaacgt caagcatctc aaaattctca acactccaaa    240 ctgtgcccctt cagattgtag cccggctgaa gaacaacaac agacaagtgt gcattgaccc    300
gaagctaaag tggattcagg agtacctgga gaaagctta aacaagtaag cacaacagcc    360
aaaaaggact ttccgctaga cccactcgag gaaaactaaa accttgtgag agatgaaagg    420
gcaaagacgt gggggagggg gccttaacca tgaggaccag gtgtgtgtgt ggggtgggca    480
cattgatctg ggatcgggcc tgaggtttgc agcatttaga ccctgcattt atagcatacg    540
gtatgatatt gcagcttata ttcatccatg ccctgtacct gtgcacgttg aactttat    600 tactggggtt tttctaagaa agaaattgta ttatcaacag catttttcaag cagttagttc    660 cttcatgatc atcacaatca tcatcattct cattctcatt ttttaaatca acgagtactt    720
caagatctga atttggcttg tttggagcat ctcctctgct ccctggggga gtctgggcac    780
agtcaggtgg tggcttaaca gggagctgga aaaagtgtcc tttcttcaga cactgaggct    840
```

```
cccgcagcag cgcccctccc aagaggaagg cctctgtggc actcagatac cgactggggc      900
tggggcgccg ccactgcctt cacctcctct ttcaaacctc agtgattggc tctgtgggct      960
ccatgtagaa gccactatta ctgggactgt ctcagagacc cctctcccag ctattcctac     1020
tctctccccg actccgagag catgcttaat cttgcttctg cttctcattt ctgtagcctg     1080
atcagcgccg caccagccgg gaagagggtg attgctgggg ctcgtgccct gcatccctct     1140
cctcccaggg cctgcccac agctcgggcc ctctgtgaga tccgtctttg gcctcctcca      1200
gaatggagct ggccctctcc tggggatgtg taatggtccc cctgcttacc cgcaaaagac     1260
aagtctttac agaatcaaat gcaattttaa atctgagagc tcgcttgagt gactgggttt     1320
gtgattgcct ctgaagccta tgtatgccat ggaggcacta acaaactctg aggtttccga     1380
aatcagaagc gaaaaaatca gtgaataaac catcatcttg ccactacccc ctcctgaagc     1440
cacagcaggg gttcaggttc aatcagaac tgttggcaag gtgacatttc catgcataga      1500
tgcgatccac agaaggtcct ggtggtattt gtaacttttt gcaaggcatt ttttatata      1560 tattttgtg cacattttt tttacgattc tttagaaaac aaatgtattt caaatatat       1620 ttatagtcga acaagtcata tatgaatg agagccatat gaatgtcagt agtttatact      1680
tctctattat ctcaaactac tggcaatttg taaagaaata tatatgatat ataaatgtga     1740
ttgcagcttt tcaatgttag ccacagtgta tttttcact tgtactaaaa ttgtatcaaa      1800
tgtgacatta tatgcactag caataaaatg ctaattgttt catggta                   1847
```

<210> SEQ ID NO 4
<211> LENGTH: 89
<212> TYPE: PRT
<213> ORGANISM: Homo sapiens

<400> SEQUENCE: 4

```
Met Asn Ala Lys Val Val Val Leu Val Leu Val Leu Thr Ala Leu
  1               5                  10                  15

Cys Leu Ser Asp Gly Lys Pro Val Ser Leu Ser Tyr Arg Cys Pro Cys
                 20                  25                  30

Arg Phe Phe Glu Ser His Val Ala Arg Ala Asn Val Lys His Leu Lys
             35                  40                  45

Ile Leu Asn Thr Pro Asn Cys Ala Leu Gln Ile Val Ala Arg Leu Lys
         50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys
                 85
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: PCR primers

<400> SEQUENCE: 5

```
ctctccaaag gaaagcgagg tggacat                                           27
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: PCR primers

```
<400> SEQUENCE: 6
tgatttcagc acctacagtg tacagtct                                      28

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide amino acid residues 1-38 of SEQ ID NO. 2

<400> SEQUENCE: 7

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys
        35

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: PCR primers

<400> SEQUENCE: 8
ctctccaaag gaaagcgagg tggacat                                       27

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PCR primers

<400> SEQUENCE: 9
agactgtaca ctgtaggtgc tgaaatca                                      28

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PCR primers

<400> SEQUENCE: 10
cggagcaata tgaaatgatc t                                             21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: PCR primers

<400> SEQUENCE: 11
gcaaatacag ctcctattg                                                19

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: PCR primers
```

<400> SEQUENCE: 12
atctgtttcc actgagtctg atcttcaagt tttcacccag ctaacaca          48

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: PCR primers

<400> SEQUENCE: 13
taggcctgac tggcattgta ttagcaaact catcactaga                   40

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: PCR primers

<400> SEQUENCE: 14
caagctcgaa attaaaaccc tcactaaagg gctctccaaa ggaaagcgag gtggacat   58

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: PCR primers

<400> SEQUENCE: 15
cacttaacta atacgactca ctatagggag actgtacact gtaggtgcga aatca    55

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: PCR primers

<400> SEQUENCE: 16
ctctccaaag gaaagcgagg tggacat                                 27

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: PCR primers

<400> SEQUENCE: 17
tgatttcagc acctacagtg tacagtct                               28

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: PCR primers

<400> SEQUENCE: 18
agatagatcc gcggaccatg gagggatca gtatata                      37

<210> SEQ ID NO 19
<211> LENGTH: 38

```
<212> TYPE: DNA
<213> ORGANISM: Artificial Sequence
<220> FEATURE:
<223> OTHER INFORMATION: Description of Artificial Sequence: PCR primers

<400> SEQUENCE: 19
tagatacaac tagtgtgtta gctggagtga aaacttga                                38

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: PCR primers

<400> SEQUENCE: 20
agatagatcc gcgggtgtta gctggagtga aaacttga                                38

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: PCR primers

<400> SEQUENCE: 21
tagatacaac tagtaccatg gagggatca gtatata                                  37

<210> SEQ ID NO 22
<211> LENGTH: 61
<212> TYPE: DNA
<213> ORGANISM: Homo sapiens

<400> SEQUENCE: 22
gccaccgcat ctggagaacc agcggttacc atggagggga tccagtatat acacttcaga        60
t                                                                        61

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Antisense
      oligonucleotides for CXCR-4

<400> SEQUENCE: 23
cggtggcgta gacctcttgg                                                    20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Antisense
      oligonucleotides for CXCR-4

<400> SEQUENCE: 24
ccaatggtac ctcccctag                                                     19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Antisense
      oligonucleotides for CXCR-4
```

-continued

```
<400> SEQUENCE: 25
ggtcatatat gtgaagtcta                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Antisense
      oligonucleotides for CXCR-4

<400> SEQUENCE: 26
actagagata cagatcatat                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Antisense
      oligonucleotides for CXCR-4

<400> SEQUENCE: 27
catatacgat cgatcgatgc                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Antisense
      oligonucleotides for CXCR-4

<400> SEQUENCE: 28
gatagtgctg atcgatgcta                                                  20
```

THERAPEUTIC AND DIAGNOSTIC APPLICATIONS BASED ON THE ROLE OF THE CXCR-4 GENE IN TUMORIGENESIS

CROSS-REFERENCES TO RELATED APPLICATIONS

This application is a divisional application of U.S. patent application Ser. No. 10/985,324, filed on Nov. 9, 2004, now abandoned, which is a continuation of U.S. patent application Ser. No. 09/647,501, filed on Jun. 15, 2001, now granted as U.S. Pat. No. 6,863,887, Mar. 8, 2005, which is a United States national phase application under 35 U.S.C. §371 of International Patent application number PCT/US99/07431, filed Mar. 29, 1999, which claims priority to U.S. provisional application Ser. No. 60/079,916, filed Mar. 30, 1998 and U.S. provisional application Ser. No. 60/104,656, filed Oct. 16, 1998, all of which are incorporated herein by reference.

FIELD OF THE INVENTION

The present invention relates to the identification of a novel role for the CXCR-4 gene (SEQ ID NO:1) in tumorigenesis, in particular primary brain, breast and colon tumorigenesis. The present invention is related to the role of CXCR-4 nucleic acids and polypeptides as diagnostic tools to indicate a precancerous condition or cancer, and therapeutic agents based thereon to inhibit CXCR-4 gene expression and/or activity as a method of treating and/or preventing tumorigenesis.

BACKGROUND OF THE INVENTION 2.1 Brain Tumors

Brain tumors are among the leading cause of death among young children and adults. A survey by the American Cancer Society has documented that 13,300 people died of brain tumors in 1995 and predicated that over 17,900 would die in 1996 (Parker et al., 1996, CA Cancer J. Clin., 46:5-28). The number of deaths due to brain tumors has been increasing at a significant rate each year. On average, 25,000 Americans are diagnosed with brain cancer yearly. Brain tumors claim the lives of more children than any other form of cancer except leukemia.

The increased incidence of brain tumors is not only evident in children but also in adults. It has been documented that a significant increase in mortality has occurred in adult primary malignant tumors between 1982 and 1996 (Parker et al., 1996, CA Cancer J. Clin., 46:5-28). Glioblastomas, astrocytomas and meningiomas are the most common brain tumors that affect adults (Thapar and Laws, 1993, CA Cancer J. Clin., 43:253-271).

The transformation of normal human brain cells into gliomas occurs as a result of the accumulation of a series of cellular and genetic changes (Sehgal, 1998 Cancer Surv., 25:233-275; vonDiemiling et al., 1995 Glia 15:328-338; Furnari et al., 1995, J. Surg. Oncol. 67:234). These genetic alterations include the loss, gain or amplification of different chromosomes. These genetic changes lead to altered expression of proteins that play important roles in the regulation of normal cell proliferation. Several common genetic alternations at the chromosomal level (loss of 17p, 13q, 9p, 19, 10, 22q, 18q and amplification of 7 and 12q) have been observed (Sehgal et al., 1998, J. Surg. Oncol. 57:23; vonDiemiling et al., 1995, Glia 15:328-338; Furnari et al., 1995, Cancer Surv. 25:233-275). These alterations lead to changes in the expression of several genes (p53, RB, INFα/β, CDKN2, MMAC1, DCC, EGFR, PDGF, PDGFr, MDM2, GLI, CDK4 and SAS) during the genesis and progression of human gliomas (Sehgal, 1998, J. Surg. Oncol. 67:234; vonDiemiling et al., 1995, Glia 15:328-338). Recent studies have suggested that altered expression of several other genes (MET, MYC, TGFβ, CD44, VEGF, NCAML1, $p21^{waf1/CiP1}$, trkA, MMRs, C4-2, D2-2) and proteins (cathepsins, tenascin, matrix metalloproteases, tissue inhibitors of metalloproteases, nitric oxide synthetase, integrins, IL 13 receptor, Connexin 43, uPAR's extracellular matrix proteins and heat shock proteins) are associated with the genesis of human gliomas (Sehgal, 1998, J. Surg. Oncol. 57:234). Taken together, these findings point to the fact that accumulation of multiple genetic mutations coupled with extensive changes in gene expression may be a prerequisite in the etiology of human gliomas. Despite identification of these genetic alterations, the exact series of events that leads to the genesis of human gliomas is not clear.

Glioblastoma multiforme are high grade astrocytomas that grow very rapidly and contain cells that are very malignant (Laws and Thapar, 1993, CA Cancer J. Clin., 43:263-271). The molecular basis of glioblastoma multiforme occurrence may involve systematic events at the chromosomal level or at a gene expression level. These may include inactivation of tumor suppressor genes, activation of oncogenes or specific translocations at the chromosomal level. Some genetic changes at the chromosomal level and gene expression level have been well documented for other brain tumors (Furnari et al., 1995, Cancer Surv., 25:233-275). For example, it has been documented that loss of tumor suppressor(s) genes at chromosome 10, mutations in p53, or overexpression of epidermal growth factor receptor, may be major events leading to glioblastoma multiforme. A number of other genes such as EGFR, CD44, β4 integrins, membrane-type metalloproteinase (MT-MMP), p21, p16, p15, myc, and VEGF have been shown to be overexpressed in different types of brain tumors (Faillot et al., Neurosurgery, 39:478-483; Eibl et al., 1995, J. of Neurooncol., 26:165-170; Previtali et al., 1996, Neuropathol. Exp. Neurol., 55:456-465; Yamamoto et al., 1996, Cancer Res., 56:384-392; Jung et al., 1995, Oncogene, 11:2021-2028; Tsuzuki et al., 1996, Cancer, 78:287-293; Chen et al., 1995, Nature Med., 1:638-643; Takano, et al., Cancer Res., 56:2185-2190; Bogler et al., 1995, Glia, 15:308-327). Other genes such as p53 show mutations in the majority of brain tumors (Bogler et al., supra). How the interplay of one more of these genes leads to tumorigenesis is not known but most likely multiple steps are required for neoplastic transformation. The exact series of events that lead to initiation or progression of glioblastoma are not known at present and useful markers for early detection of brain tumors are lacking.

2.2 CXCR-4

Chemokine receptors play an important role in the chemotaxis of T cells and phagocytic cells to areas of inflammation. CXCR-4 was first identified as a cDNA that was amplified using degenerate primers made against leukocyte chemotactic factor receptors (N-formyl peptides, C5a and IL-8) and was termed HM89 (Endres et al., 1996, Cell 87:745). Ligand binding analysis showed that HM89 was not a N-formyl peptide receptor, but sequence analysis clearly demonstrated that it is a member of the G protein coupled receptor family. Cytogenetic analysis indicates that HM89 is localized to human chromosome 2q21 (Benl et al., 1996, Nature 382: 829). HM89 was later re-cloned using a rabbit IL-8 receptor cDNA upon screening a human monocyte library and was named LESTR (leukocyte derived seven transmembrane domain receptor (Nagasawa et al. 1996, Nature 382:635); and was again cloned and identified as a co-factor for HIV-1 fusion and entry into CD4+ cells (De Risi et al., 1996, Nature, Genetics 14:457). This co-factor was identical to the previously cloned HM89, and because of its role as a fusion protein between the HIV-1 virus and CD4+ cells it was designated as "fusin". Fusin in conjunction with CD4 is sufficient to allow HIV-1 entry into non-permissive murine 3T3 cells (De Risi et al., 1996, Nature, Genetics 14:457). Sequence analysis indicated that HM89, LESTR and fusin are all the same gene and because of chemo-attraction properties, these genes are now termed CXC-chemokine receptor-4 (CXCR-4). Recently, it is shown that the CD4-independent infection by HIV-1 was mediated by the CXCR-4 receptor (Feng et al., 1996, Science 172:872). The ligand for CXCR-4 was recently cloned and termed PBSF/SDF-1 (Pre-B-cell growth stimulating factor/Stromal cell derived factor-1) (Engelhard et al., 1997, Neurosurgery 41:886). Transgenic mice that lack PBSF/SDF-1 died prenatally and their B-cells and myeloid progenitors were severely reduced in numbers (Harihabu et al., 1997 J. Biol. Chem. 272:28726). This result clearly demonstrates that PBSF/SDF-1 is responsible for B-cell lymphoesis and bone marrow myelopoiesis.

Recent studies demonstrate that CXCR-4 functions as a co-receptor with CD4 for the entry of T-cell tropic strains of HIV into target cells (Nomura et al., 1993, Int. Immunol. 5:1239; Federsppiel et al., 1993, Genomics 16:707). The mechanism by which HIV-1 interacts with the CXCR-4 chemokine receptor and CD4+ molecules during infection is unclear. It was also demonstrated that HIV-2 infection of CD4-cells can occur rapidly by utilizing the HIV-1 co-factor CXCR-4 receptor (Loctscher et al., 1994, J. Biol. Chem. 269:232). Interaction and cytopathic effects caused by entry of HIV-2 into CD4-cells were inhibited by a monoclonal antibody to the CXCR-4 protein (Doranz et al., 1997, Immunol. Resh. 16:15) (Feng et al., 1996, Science 272:872). The role of CXCR-4 in HIV infection was further strengthened when its introduction into human and nonhuman CD4-cells allowed HIV-2 infection (Doranz et al., 1997, Immunol. Res. 16:15) (Feng et al., 1996, Science 272:872).

Citation of references herein shall not be construed as an admission that such references are prior art to the present invention.

BRIEF SUMMARY OF THE INVENTION

The present invention relates to the discovery of a novel role for CXCR-4 in the aberrant proliferative behavior of a number of cell types, including numerous primary tumors and derived cell lines. In particular, the present invention relates to the identification of the role of CXCR-4 in cell transformation and tumorigenesis, in particular, brain, breast and colon tumors. The present invention encompasses therapeutic and diagnostic applications based on CXCR-4 proteins, nucleic acids, and agonists and antagonists, for the treatment or prevention of tumorigenesis. The present invention further encompasses therapeutic and diagnostic applications based on a ligand of CXCR-4, SDF-1 and SPF-1 proteins, nucleic acids, and agonists and antagonists, for the treatment or prevention of tumorigenesis. The present invention further encompasses screening assays to identify modulators of CXCR-4 activity and/or expression as potential therapeutic agents for the treatment and/or prevention of a transformed phenotype or tumorigenesis.

The present invention is based, in part, on the Applicants' surprising discovery that the CXCR-4 nucleotide sequence (SEQ ID NO:1) and encoded gene product (SEQ ID NO:2) is expressed at high levels in glioblastoma multiforme tissue, as well as, certain other forms of tumors and cancers.

In one embodiment, the present invention encompasses nucleotide sequences complementary to the nucleotide sequence of CXCR-4 (SEQ ID NO:1), such as primers, fragments or antisense nucleotides which may be used to determine the level of CXCR-4 expression in a tissue or cell culture sample as prognostic of a pre-cancerous or transformed cell phenotype; or to inhibit CXCR-4 expression as a method of treating or preventing a pre-cancerous or transformed cell phenotype. In a specific embodiment, the CXCR-4 gene is a human gene (SEQ ID NO:1) and the CXCR-4 protein is a human protein (SEQ ID NO:2) is a human protein.

The present invention also encompasses inhibitors of CXCR-4 activities related to cellular transformation. CXCR-4 (SEQ ID NO:2) is a known G protein coupled receptor involved in transducing signals. The present invention encompasses peptide fragments or antagonists, antibodies, or small compounds which may inhibit or compete with ligands binding to CXCR-4 and thus inhibit CXCR-4 activity. The invention further encompasses peptide fragments (and derivatives and analogs thereof) which comprise one or more domains of a CXCR-4 protein which may be used to prevent ligands binding to CXCR-4. Antibodies to CXCR-4, and to CXCR-4 derivatives and analogs, are additionally provided. Methods of production of the CXCR-4 proteins, and to CXCR-4 derivatives and analogs, e.g., by recombinant means, are also provided.

The present invention further encompasses screening assays to identify compounds which inhibit CXCR-4 gene (SEQ ID NO:1) expression or gene product activity as potential therapeutics for the treatment and/or prevention of tumorigenesis. In particular, the present invention encompasses host cell lines or transgenic animals which express CXCR-4 at high levels which have utility as tools for screening assays to identify agents which inhibit CXCR-4 expression and/or activity as potential therapeutic agents for the treatment and prevention of tumorigenesis.

The present invention also encompasses therapeutic and diagnostic methods and compositions based on CXCR-4 proteins and nucleic acids. Therapeutic compounds of the invention include but are not limited to CXCR-4 proteins and analogs and derivatives (including fragments) thereof; antibodies thereto; nucleic acids encoding the CXCR-4 proteins, analogs, or derivatives; and CXCR-4 antisense nucleic acids.

The invention provides for treatment of disorders of overproliferation (e.g., tumors, cancer and hyperproliferative disorders) by administering compounds that decrease or antagonize (inhibit) CXCR-4 function (e.g., antibodies, antisense nucleic acids, ribozymes).

The invention also provides methods of treatment of disorders involving deficient cell proliferation (growth) or in which cell proliferation is otherwise desired (e.g., degenerative disorders, growth deficiencies, lesions, physical trauma) by administering compounds that promote CXCR-4 activity (e.g., an agonist of CXCR-4; nucleic acids that encode CXCR-4).

Animal models, diagnostic methods and screening methods for predisposition to disorders, and methods for identification of CXCR-4 agonists and antagonists, are also provided by the invention.

3.1 Definitions and Abbreviations

As used herein, underscoring or italicizing the name of a gene shall indicate the gene, in contrast to its encoded protein product, which is indicated by the name of the gene in the absence of any underscoring or italicizing. For example, "CXCR-4" shall mean the CXCR-4 gene, whereas "CXCR-4" shall indicate the protein product of the CXCR-4 gene.

As used herein, the following terms shall have the meanings indicated.

CXCR-4 nucleotides or coding sequences: DNA sequences encoding CXCR-4 mRNA transcripts, protein, polypeptide or peptide fragments of CXCR-4 protein, and CXCR-4 fusion proteins, and RNA sequences corresponding the CXCR-4 mRNA transcripts and RNA sequences which are complementary to the mRNA transcript, CXCR-4 nucleotide sequences encompass RNA, DNA, including genomic DNA (e.g., the CXCR-4 gene) and cDNA.

CXCR-4: gene products, e.g., transcripts and the CXCR-4 protein. Polypeptides or peptide fragments of the protein are referred to as CXCR-4 polypeptides or CXCR-4 peptides. Fusions of CXCR-4 protein, polypeptides, or peptide fragments to an unrelated protein are referred to herein as CXCR-4 fusion proteins.

As used herein, the following terms shall have the abbreviations indicated.

CD: cytoplasmic domain
DD-PCR: differential display-polymerase chain reaction
ECD: extracellular domain
FNHA: fetal normal human astrocytes
GMTT: glioblastomas multiforme tumor tissue
MTB: multiple tissue blot
MTT: meningioma tumor tissue
NBT: normal brain tissue
ORF: open reading frame
RT-PCR: reverse transcription-polymerise chain reaction
TM: transmembrane domain
UTR: untranslated region
Brain Tumor Cell Lines:
　CCF-STTG1: astrocytoma grade IV
　D283 Med: medulloblastoma
　DETRG-05MG: glioblastoma multiforme
　Hs 683: glioma
　IMR-32: neuroblastoma
　PFSK-1: primitive neuroectodermal tumor
　SW 1783: astrocytoma grade III

BRIEF DESCRIPTION OF THE DRAWINGS

FIGS. 1A-C. Identification of the CXCR-4 gene. Panels A and B show expression arrays hybridized with $P^{32}$ labeled cDNA from Normal and Tumor tissue, respectively. The CXCR-4 gene is indicated by a thick arrow in panel B. Two other genes that were expressed at similar levels in both normal and tumor tissue are indicated by small arrows. Panel C shows analysis of CXCR-4 expression in Normal and Tumor (N and T) tissue using the gene specific RT-PCR technique. The housekeeping gene (D1-2) is indicated by letter H.

FIGS. 4A and 4B show CXCR-4 expression in primary breast tissue (N=normal and T=tumor) and cell lines, respectively.

FIG. 7A shows the ethidium bromide stained gel and FIG. 7B shows the autoradiogram. To isolate the CXCR-4 0.55 Kb fragment for labeling as a probe, 125 ng of cDNA (prepared using oligodT and random hexamer primer from human neuroblastoma cell line) was used as a template. PCR amplification of CXCR-4 fragment was done using gene specific primers (5'CTCTCCAAAG-GAAAGCGAGGTGGACAT3' (SEQ ID NO:5) and 5'TGATTTCAGCACCTACAGTGTACAGTCT3' (SEQ ID NO:6)) using the PCR conditions described herein. CXCR-4 genomic band in the mouse lane is indicated by an arrow in FIG. 7B.

FIGS. 8A-P. In situ hybridization of CXCR-4 on mouse embryos. FIGS. 8A-D: A=8 day whole embryos, B=9 day embryo (head region), C=9 day embryo (organ region), D=10 day embryo (organ region), FIGS. 8E-F are same as FIGS. 8A-D but instead hybridized with CXCR-4 sense probe. FIGS. 8I-O: I=10 day embryo (head region), J=11 day embryo (heart region), K=11 day embryo (forehead region), L=13 day embryo (spinal cord), M=15 day embryo (pituitary), N=15 day embryo (forebrain), O=14 day embryo ribs (near spine) and P=16 day embryo fore limbs. High level of CXCR-4 expression are indicated by arrows.

FIG. 9A and FIG. 9B show cells transfected with pCMV-neoCS (CXCR-4 sense). FIG. 9C and FIG. 9D show cells transfected with pCMV-neoCA (CXCR-4 anti-sense). Neurite out-growth in pCMV-neoCA transfected cells are indicated by arrows in FIG. 9C. 48 hours after the transfection, cells were selected in G418 (1000 µg/ml) for 3 weeks. Cell morphology was observed under the inverted light microscope at 5× magnification. (FIG. 9A and FIG. 9B) Glioblastoma 5 GB cells transfected with pCMV-neo or pCMV-neoCA (CXCR-4 anti-sense), respectively. (FIG. 9C and FIG. 9D) Glioblastoma GB1690 cells transfected with pCMV-neo or pCMV-neoCA (CXCR-4 anti-sense), respectively, Neurite out-growth are indicated by arrows. Immunohistochemistry in the anti-sense transfected cells showed 50% reduced in the expression of CXCR-4 and increased expression of GFAP.

FIGS. 10A, B and C show cells transfected with pCMV-neo, pCMV-neoCS (CXCR-4 sense) and pCMV-neoCA (CXCR-4 anti-sense), respectively. Neurite out-growths in pCMV-neoCA transfected cells are indicated by arrows in FIG. 10C.

FIGS. 12A-E. Effect of CXCR-4 over-expression on colony formation in soft agar of Glioblastoma cell line GB 1690. GB 1690 cells that were transfected with vector alone and with CXCR-4 in sense direction were trypsinized. Approximately, $1 \times 10^6$ cells were mixed with 0.26% agar. Cells were then plated on top of a layer 0.65% agar in 60 mm petri dishes and incubated 37° C. for 2-4 weeks. Cells were fed with serum containing media after every 10 days. Colonies were counted under the inverted light microscope. FIGS. 12A-B, pCMV-neo vector alone; 12C-D, pCMV-neoCS; 12E is histogram of number colonies.

FIG. 14. Nucleotide (SEQ ID NO:1) and amino acid (SEQ ID NO:2) sequence of human CXCR-4.

FIG. 15. Nucleotide (SEQ ID NO:3) and amino acid (SEQ ID NO:4) sequence of human SDF-1.

DETAILED DESCRIPTION OF THE INVENTION

Figure 2A:
FIGS. 2A-B. Expression analysis of CXCR-4 in GMTT and NBT using the technique of in situ hybridization. Panel A shows GMTT hybridized with a sense probe. Panel B shows GMTT hybridized with a CXCR-4 anti-sense probe. CXCR-4 expression is indicated by arrows.

The present invention relates to the identification of a novel role of CXCR-4 in cell transformation and aberrant cellular proliferation. In particular, the present invention relates to the altered gene expression of CXCR-4 in a number of primary tumors and cell lines derived from tumors, in addition to, the altered gene expression of ligands for CXCR-4. Further, the present invention relates, in part, to the Applicants' surprising discovery that CXCR-4 in the presence of its ligand, SDFβ-1, is required for the proliferation of tumor cells and the inhibition of CXCR-4 gene expression or the inhibition of CXCR-4 activity in transformed cells reverses the transformed phenotype.

The present invention encompasses compounds and methods for the detection of aberrant CXCR-4 gene expression or activity as a diagnostic tool to indicate a transformed, pre-cancerous or cancerous cell phenotype. The present invention further encompasses compounds and methods for the detection of aberrant SDF-1 gene expression or activity as a diagnostic or prognostic tool to indicate a transformed, precancerous or cancerous cell phenotype. The present invention also encompasses compounds and methods for the modulation of CXCR-4 gene expression or activity as a method of treating or preventing a transformed, pre-cancerous or cancerous cell phenotype. In this regard, the present invention provides nucleotide sequences of CXCR-4 genes, and amino acid sequences of their encoded proteins. The invention further provides fragments and other derivatives, and analogs, of CXCR-4 proteins. Nucleic acids encoding such fragments or derivatives are also within the scope of the invention. The invention provides CXCR-4 genes and their encoded proteins of humans and related genes (homologs) in other species. In specific embodiments, the CXCR-4 genes and proteins are from vertebrates, or more particularly, mammals. In a preferred embodiment of the invention, the CXCR-4 genes and proteins are of human origin (SEQ ID NO:1 and SEQ ID NO:2, respectively). Production of the foregoing nucleic acids, proteins and derivatives, e.g., by recombinant means, is provided.

CXCR-4 is a gene identified by the method of the invention, that is expressed, at high levels in glioblastoma multiforme tissue as well as certain others forms of tumors and cancers.

The invention also provides CXCR-4 derivatives and analogs of the invention which are functionally active, i.e., they are capable of displaying one or more functional activities described herein associated with a full-length (wild-type) CXCR-4 protein. Such functional activities include, but are not limited to, antigenicity, i.e., ability to bind (or compete with CXCR-4 for binding) to an anti-CXCR-4 antibody, immunogenicity, i.e., ability to generate antibody which binds to CXCR-4, and ability to bind (or compete with CXCR-4 for binding) to a ligand for CXCR-4. The invention further provides fragments (and derivatives and analogs thereof) of CXCR-4 which comprise one or more domains of the CXCR-4 protein. Antibodies to CXCR-4, its derivatives and analogs, are additionally provided.

The present invention also provides therapeutic and diagnostic methods and compositions based on CXCR-4 proteins and nucleic acids and anti-CXCR-4 antibodies. The invention provides for treatment of disorders of overproliferation (e.g., cancer and hyperproliferative disorders) by administering compounds that decrease CXCR-4 activity (e.g., antibodies, CXCR-4 antisense nucleic acids).

The invention also provides methods of treatment of disorders involving deficient cell proliferation or in which cell proliferation (growth) is otherwise desirable (e.g., growth deficiencies, degenerative disorders, lesions, physical trauma) by administering compounds that promote CXCR-4 function.

The present invention further provides screening assays to identify novel agents which target CXCR-4 gene expression or CXCR-4 protein activity, including interaction with ligands, e.g., SDF-1, and, thus are potential therapeutic agents for the treatment or prevention of cell transformation, or pre-cancerous or cancerous phenotypes, i.e., tumorigenesis. The screening assays of the present invention may function to identify novel exogenous or endogenous agents that inhibit CXCR-4 expression or inhibit the interaction between CXCR-4 and its ligand, e.g., SDF-1. A variety of protocols and techniques may be used to identify drugs that inhibit CXCR-4 gene expression and/or CXCR-4 activity, and as a result inhibit CXCR-4 participation in aberrant cellular proliferative activity. such identified agents have utility in the treatment of hosts demonstrating a cellular transformed phenotype or aberrant cellular proliferative behavior, and advantageously would be effective to treat and/or prevent tumorigenesis.

The present invention further encompasses pharmaceutical compositions containing the novel agents identified by the screening assays described herein. The invention provides therapeutic modalities and pharmaceutical compositions for the treatment of tumorigenesis and the prevention of transformed phenotypes. The therapeutic modalities of the present invention further encompass combination therapies in which an agent which inhibits CXCR-4 gene expression and/or activity, and at least one other therapeutic agent, e.g., a chemotherapeutic agent, are administered either concurrently, e.g., as an admixture, separately but simultaneously or concurrently, or sequentially.

The novel therapeutic combinations of the present invention provide a means of treatment which may not only reduce the effective dose of either drug required for antitransformation or antitumorigenesis, thereby reducing toxicity, but may improve the absolute therapeutic effect as a result of attacking aberrant cellular proliferation through a variety of mechanisms.

The invention is illustrated by way of examples infra which disclose, inter alia, the isolation and characterization of CXCR-4 (SEQ ID NO:2), and patterns of expression of CXCR-4 in certain tumors (see Section 6).

For clarity of disclosure, and not by way of limitation, the detailed description of the invention is divided into the subsections which follow.

5.1 Identification of Role of CXCR-4 in Transformation

The present invention relates to the novel role of CXCR-4 in the promotion of cell transformation and tumorigenesis. In particular, the present invention relates to the Applicants' findings that (a) CXCR-4 (SEQ ID NO:2) is over-expressed in glioblastoma multiforme tumor tissue and a number of other primary tumors; (b) the expression of the CXCR-4 gene (SEQ ID NO:1) is required for continuous proliferation of glioblastoma cancer cells and blocking of its gene function results in growth arrest; and (c) over-expression of CXCR-4 in the sense orientation results in enhanced and rapid cellular proliferation and colony formation in soft agar.

The present invention further relates to the Applicants' findings that CXCR-4 (SEQ ID NO:2) is over-expressed in several brain tumor derived cell lines and primary brain tumor tissues, including neuroblastoma and neuroectodermal human tumor cell lines, medulloblastoma and astrocytoma grade III cell lines, and primary glioma and meningioma tumors. Further, CXCR-4 (SEQ ID NO:2) was found to be over-expressed in breast tumor tissues, lymphoblastic leukemia cell lines, Burkitt's lymphoma cell lines, colorectal adenocarcinomas, lung carcinoma, and melanoma cell lines.

The present invention relates to the role of CXCR-4 in promotion of cell transformation and tumorigenesis, and provides methods including the use of CXCR-4 nucleic acids and nucleic acids which hybridize or complement CXCR-4 nucleic acids, as diagnostic and prognostic tools for the detection of transformed, pre-cancerous and cancerous phenotypes. The present invention provides methods for use of CXCR-4 nucleic acids and those which complement and/or hybridize to nucleic acid sequences which encode CXCR-4 as therapeutics to treat or prevent transformed, pre-cancerous and cancerous phenotypes. In particular, the invention provides compositions comprising nucleic acid sequences which inhibit CXCR-4 expression as therapeutics to treat or prevent transformed, pre-cancerous, and cancerous phenotypes.

5.2 The Production of CXCR-4 Nucleic Acids, Polypeptides and Antibodies as Diagnostics, Therapeutics and Components for Screening Assays The present invention encompasses the use of agents for the detection of aberrant CXCR-4 gene expression as diagnostic or prognostic tools to detect a transformed phenotype, pre-cancerous or cancerous condition. Diagnostic or prognostic tools which may be used in accordance with the present invention include, but are not limited to, (a) nucleic acids which hybridize or are complementary to the CXCR-4 nucleotide sequence (SEQ ID NO:1); (b) polypeptides, peptide fragments or synthetic molecules which bind to the CXCR-4 ligand binding domain; and (c) antibodies which bind to CXCR-4.

The present invention relates to the use of agents which inhibit CXCR-4 gene expression and/or protein activity as therapeutics for the treatment and/or prevention of a transformed or pre-cancerous phenotype, or cancer or tumorigenesis, Therapeutic agents which may be used in accordance with the present invention include, but are not limited to, (a) nucleic acids which inhibit CXCR-4 gene expression, e.g., antisense molecules, ribozymes or triple helix molecules complementary to CXCR-4 (SEQ ID NO:1); (b) polypeptides, peptides, antibodies, small organic molecules or synthetic molecules which inhibit CXCR-4 activity or prevent CXCR-4 from binding its ligand; and (c) peptides, polypeptides, antibodies, small organic molecules or synthetic molecules which act as antagonists of CXCR-4 activity.

The present invention provides screening assays for the identification of agents which inhibit CXCR-4 gene expression and/or activity. In one embodiment of the invention, an important component of the screening assays of the present invention are nucleotide coding sequences encoding CXCR-4 proteins, polypeptides and peptides. The present invention further encompasses (a) DNA vectors that contain any of the foregoing CXCR-4 encoding sequences and/or their complements; (b) DNA expression vectors that contain any of the foregoing CXCR-4 coding sequences operatively associated with a regulatory element that directs the expression of the coding sequences in the host cell; and (c) genetically engineered host cells that contain any of the foregoing CXCR-4 coding sequences operatively associated with a regulatory element that directs the expression of the coding sequences in the host cell.

The present invention provides the use of agents for the detection of aberrant SDF-1 gene expression as diagnostic or prognostic tools to detect a transformed phenotype, pre-cancerous or cancerous condition. The present invention encompasses the use of agents which inhibit SDF-1 gene expression and/or protein activity as therapeutics for the treatment and/or prevention of a transformed or pre-cancerous phenotype, or cancer or tumorigenesis. The present invention further encompasses screening assays for the identification of agents which inhibit SDF-1 gene expression and/or activity. The present invention is described in terms of CXCR-4 by way of example, and not by way of limitation to exclude SDF-1. The present invention includes, but is not limited to (a) nucleic acids which hybridize or are complementary to the SDF-1 coding sequence (see FIG. 15, SEQ ID NO:3)); and (b) polypeptides, peptides, antibodies, small organic molecules or synthetic molecules which may be used for the detection or inhibition of SDF-1 gene expression or activity.

5.2.1. The CXCR-4 Nucleic Acids

The invention relates to the nucleotide sequences of CXCR-4 nucleic acids. In specific embodiments, CXCR-4 nucleic acids comprise the cDNA sequences of SEQ ID NO:1, or the coding regions thereof, or nucleotide sequences encoding a CXCR-4 protein (e.g., a protein having the sequence of SEQ ID NO:2). Nucleic acids of the present invention can be single or double stranded. The invention also relates to nucleic acids hybridizable to or complementary to the foregoing sequences. In specific aspects, nucleic acids are provided which comprise a sequence complementary to at least 10, 25, 50, 100, 200, or 250 contiguous nucleotides of a CXCR-4 gene. In a specific embodiment, a nucleic acid which is hybridizable to a CXCR-4 nucleic acid (e.g., having sequence SEQ ID NO:1), or to a nucleic acid encoding a CXCR-4 derivative, under conditions of low stringency is provided.

By way of example and not limitation, procedures using such conditions of low stringency are as follows (see also Shilo and Weinberg, 1981, Proc. Nat'l Acad. Sci. USA 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.20% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

In another specific embodiment, a nucleic acid which is hybridizable to a CXCR-4 nucleic acid (SEQ ID NO:1) under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well know in the art.

In another specific embodiment, a nucleic acid which is hybridizable to a CXCR-4 nucleic acid (SEQ ID NO:1) under conditions of moderate stringency is provided.

Various other stringency conditions which promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5 M NaHPO$_4$ (pH 7.2)/1 mM EDTA/7% SDS, or hybridization in 50% formamide/0.25 M NaHPO$_4$ (pH 7.2)/0.25 M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH 7.2)/1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y.

Nucleic acids encoding derivatives and analogs of CXCR-4 proteins (see Sections 5.2.2), and CXCR-4 antisense nucleic acids are additionally provided. As is readily apparent, as used herein, a "nucleic acid encoding a fragment or portion of a CXCR-4 protein" shall be construed as referring to a nucleic acid encoding only the recited fragment or portion of the CXCR-4 protein and not the other contiguous portions of the CXCR-4 protein as a continuous sequence.

Fragments of CXCR-4 nucleic acids comprising regions conserved between other CXCR-4 nucleic acids, of the same or different species, are also provided. Nucleic acids encoding one or more CXCR-4 domains are provided.

Specific embodiments for the cloning of a CXCR-4 gene, presented as a particular example but not by way of limitation, follow:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed CXCR-4 product. In one embodiment, anti-CXCR-4 antibodies can be used for selection.

In another embodiment, polymerase chain reaction (PCR) is used to amplify the desired sequence in a genomic or cDNA library, prior to selection. Oligonucleotide primers representing known CXCR-4 sequences can be used as primers in PCR. In a preferred aspect, the oligonucleotide primers represent at least part of the CXCR-4 sequence presented in FIG. 14, SEQ ID NO:1. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA, cDNA, or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known CXCR-4 nucleotide sequence (SEQ ID NO:1) and the nucleic acid homolog being isolated. For cross species hybridization, low stringency conditions are preferred. For same species hybridization, moderately stringent conditions are preferred. After successful amplification of a segment of a CXCR-4 homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding CXCR-4 proteins and CXCR-4 analogs may be identified.

The above-methods are not meant to limit the following general description of methods by which clones of CXCR-4 may be obtained.

Any eukaryotic cell potentially can serve as the nucleic acid source for the molecular cloning of the CXCR-4 gene. The nucleic acid sequences encoding CXCR-4 can be isolated from vertebrate sources, including mammalian sources, such as porcine, bovine, feline, and equine, canine, human, as well as additional primate sources, avian, reptilian, amphibian, piscine, etc. sources, non-vertebrate sources such as insects, from plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a CXCR-4 (of any species) gene or its specific RNA, or a fragment thereof (see Section 5.6), is available and can be purified and labeled, the generated DNA fragments may be screened by nucleic acid hybridization to the labeled probe (Benton and Davis, 1977, Science 196:180; Grunstein and Hogness, 1975, Proc. Nat'l Acad. Sci. U.S.A. 72:3961). Those DNA fragments with substantial homology to the probe will hybridize. It is also possible to identify the appropriate fragment by, restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, promotion of cell proliferation activity, substrate binding activity, or antigenic properties of CXCR-4. If an antibody to CXCR-4 is available, the CXCR-4 protein may be identified by binding of labeled antibody to the putatively CXCR-4 synthesizing clones, in an ELISA (enzyme-linked immunosorbent assay)-type procedure.

The CXCR-4 gene can also be identified by mRNA selection by nucleic acid hybridization followed by in vitro translation. In this procedure, fragments are used to isolate complementary mRNAs by hybridization. Such DNA fragments may represent available, purified CXCR-4 DNA of another species (e.g., human, mouse, etc.).

Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against CXCR-4 protein. A radiolabelled CXCR-4 cDNA can be synthesized using the selected mRNA (from the adsorbed polysomes) as a template. The radiolabelled mRNA or cDNA may then be used as a probe to identify the CXCR-4 DNA fragments from among other genomic DNA fragments.

Alternatives to isolating the CXCR-4 genomic DNA include, but are not limited to, chemically synthesizing the gene sequence itself from a known sequence or making cDNA to the mRNA which encodes the CXCR-4 protein. For example, RNA for cDNA cloning of the CXCR-4 gene can be isolated from cells which express CXCR-4. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CXCR-4 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated CXCR-4 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The CXCR-4 sequences provided by the present invention include those nucleotide sequences encoding substantially the same amino acid sequences as found in native CXCR-4 proteins, and those encoded amino acid sequences with functionally equivalent amino acids, as well as those encoding other CXCR-4 derivatives or analogs, as described in Section 5.2.2 infra for CXCR-4 derivatives and analogs.

The CXCR-4 sequences provided by the present invention include those that encode CXCR-4 mutants that are constitutively expressed.

5.2.2. Expression of the CXCR-4 Gene

The nucleotide sequence coding for a CXCR-4 protein or a functionally active analog or fragment or other derivative thereof, can be inserted into an appropriate expression vector, i.e., a vector which contains the necessary elements for the transcription and translation of the inserted protein-coding sequence. The necessary transcriptional and translational signals can also be supplied by the native CXCR-4 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of vectors vary in their strengths and specifications. Depending on the host-vector system utilized, any one of a number of suitable transcription and translation elements may be used. In specific embodiments, the human CXCR-4 gene (SEQ ID NO:1) is expressed, or a sequence encoding a functionally active portion of human CXCR-4. In yet another embodiment, a fragment of CXCR-4 comprising a domain of the CXCR-4 protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a CXCR-4 protein or peptide fragment may be regulated by a second nucleic acid sequence so that the CXCR-4 protein or peptide is expressed in a host transformed with the recombinant DNA molecule. For example, expression of a CXCR-4 protein may be controlled by any promoter/enhancer element known in the art. Promoters which may be used to control CXCR-4 expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Nat'l Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Nat'l Acad. Sci. U.S.A. 75:3727-3731), or the tac promoter (DeBoer, et al., 1983, Proc. Nat'l Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., 1983, Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlaaf et al., 1985, Mol. Cell. Biol. 5:1639-1648; Hammer et al., 1987, Science 235:53-58; alpha 1-antitrypsin gene control region which is active in the liver (Kelsey et al., 1987, Genes and bevel. 1:161-171), beta-globin gene control region which is active in myeloid cells (Mogram et al., 1985, Nature 315:338-340 Koilias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a CXCR-4-encoding nucleic acid, one or more origins of replication, and, optionally, one or more selectable markers (e.g., an antibiotic resistance gene).

In a specific embodiment, an expression construct is made by subcloning a CXCR-4 coding sequence into the EcoRI restriction site of each of the three pGEX vectors (Glutathione S-Transferase expression vectors; Smith and Johnson, 1988, Gene 7:31-40). This allows for the expression of the CXCR-4 protein product from the subclone in the correct reading frame.

Expression vectors containing CXCR-4 gene inserts can be identified by three general approaches: (a) nucleic acid hybridization, (b) presence or absence of "marker" gene functions, and (c) expression of inserted sequences. In the first approach, the presence of a CXCR-4 gene inserted in an expression vector can be detected by nucleic acid hybridization using probes comprising sequences that are homologous to an inserted CXCR-4 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a CXCR-4 gene in the vector. For example, if the CXCR-4 gene is inserted within the marker gene sequence of the vector, recombinants containing the CXCR-4 insert can be identified by the absence of the marker gene function. In the third approach, recombinant expression vectors can be identified by assaying the CXCR-4 product expressed by the recombinant. Such assays can be based, for example, on the physical or functional properties of the CXCR-4 protein in vitro assay systems, e.g., binding with anti-CXCR-4 antibody, promotion of cell proliferation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered CXCR-4 protein may be controlled. Furthermore, different host cells have characteristic and specific mechanisms for the translational and post-translational processing and modification (e.g., glycosylation, phosphorylation of protein). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the CXCR-4 protein, fragment, analog, or derivative may be expressed as a fusion, or chimeric protein product (comprising the protein, fragment, analog, or derivative joined via a peptide bond to a heterologous protein sequence (of a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Both cDNA and genomic sequences can be cloned and expressed.

5.2.3. Identification and Purification of the CXCR-4 Gene Products

In particular aspects, the invention provides amino acid sequence of CXCR-4, preferably human CXCR-4 (SEQ ID NO:2), and fragments and derivatives thereof which comprise an antigenic determinant (i.e., can be recognized by an antibody) or which are otherwise functionally active, as well as nucleic acid sequences encoding the foregoing. "Functionally active" CXCR-4 material as used herein refers to that material displaying one or more functional activities associated with a full-length (wild-type) CXCR-4 protein, e.g., promotion of cell proliferation, binding to a CXCR-4 substrate or CXCR-4 binding partner, antigenicity (binding to an anti-CXCR-4 antibody), immunogenicity, etc.

In other specific embodiments, the invention provides fragments of a CXCR-4 protein consisting of at least 6 amino acids, 10 amino acids, 50 amino acids, or of at least 75 amino acids. In other embodiments, the invention provides proteins comprising, having, or consisting essentially of a sequence of amino acids 100% identical with SEQ ID NO:2, or SEQ ID NO:7, or any combination of the foregoing, of a CXCR-4 protein. Fragments or proteins comprising such sequences are particularly advantageously used for immunotherapy as described below. Fragments, or proteins comprising fragments, lacking some or all of the foregoing regions of a CXCR-4 protein are also provided. Nucleic acids encoding the foregoing are provided.

Once a recombinant which expresses the CXCR-4 gene sequence is identified, the gene product can be analyzed. This is achieved by assays based on the physical or functional properties of the product, including radioactive labelling of the product followed by analysis by gel electrophoresis, immunoassay, etc.

Once the CXCR-4 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.3).

Alternatively, once a CXCR-4 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105-111).

In another alternate embodiment, native CXCR-4 proteins can be purified from natural sources, by standard methods such as those described above (e.g., immunoaffinity purification).

In a specific embodiment of the present invention, such CXCR-4 proteins, whether produced by recombinant DNA techniques or by chemical synthetic methods or by purification of native proteins, include but are not limited to those containing, as a primary amino acid sequence, all or part of the amino acid sequence substantially, as well as fragments and other derivatives, and analogs as shown in FIG. 14 (SEQ ID NO:2) thereof, including proteins homologous thereto.

5.2.4. Antibodies and Immune Cells to CXCR-4

5.2.4.1. Generation of Antibodies to CXCR-4 Proteins and Derivatives Thereof According to the invention, CXCR-4 protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human CXCR-4 protein are produced. In another embodiment, antibodies to a domain of a CXCR-4 protein are produced. In a specific embodiment, fragments of a CXCR-4 protein identified as hydrophilic are used as immunogens for antibody production. In yet another embodiment of the invention, SDF-1 protein, its fragments or other derivatives, or analogs thereof, may be used as an immunogen to generate antibodies which immunospecifically bind such an immunogen. In a specific embodiment, anti-SDFβ-1 antibodies are produced.

In another specific embodiment, the antibody to a human CXCR-4 protein is a bispecific antibody (see generally, e.g., Fanger and Drakeman, 1995, Drug News and Perspectives 8:133-137). Such a bispecific antibody is genetically engineered to recognize both (1) a human CXCR-4 epitope and (2) one of a variety of "trigger" molecules, e.g., Fc receptors on myeloid cells, and CD3 and CD2 on T cells, that have been identified as being able to cause a cytotoxic T-cell to destroy a particular target. Such bispecific antibodies can be prepared either by chemical conjugation, hybridoma, or recombinant molecular biology techniques known to the skilled artisan.

Various procedures known in the art may be used for the production of polyclonal antibodies to a CXCR-4 protein or derivative or analog. In a particular embodiment, rabbit polyclonal antibodies to an epitope of a CXCR-4 protein, or a subsequence thereof, can be obtained. For the production of antibody, various host animals can be immunized by injection with the native CXCR-4 protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward a CXCR-4 protein sequence or analog thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the ESV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing technology described in PCT/US90/02545. According to the invention, human antibodies may be used and can be obtained by using human hybridomas (Cote et al., 1983, Proc. Nat'l Acad. Sci. U.S.A. 80:2026-2030) or by transforming human 3 cells with ESV virus in vitro (Cole et al., 1985, in Monoclonal Antibodies and Cancer TheranY, Alan R. Liss, pp. 77-96). In fact, according to the invention, techniques developed for the production of "chimeric antibodies" (Morrison et al., 1984, Proc. Nat'l Acad. Sci. U.S.A. 81:6851-6855; Neuberger et al., 1984, Nature 312:604-608; Takeda et al., 1985, Nature 314:452-454) by splicing the genes from a mouse antibody molecule specific for CXCR-4 together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce CXCR-4-specific single; pain antibodies. An additional embodiment of the invention utilizes the techniques described for the construction of Fab expression libraries (Huse et al., 1989, Science 246:1275-281) to allow rapid and easy identification of monoclonal Fab fragments with the desired specificity for CXCR-4 proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired-antibody can be accomplished by techniques known in the art, e.g., ELISA (enzyme-linked immunosorbent assay). For example, to select antibodies which recognize a specific domain of a CXCR-4 protein, one may assay generated hybridomas for a product which binds to a CXCR-4 fragment containing such domain. For selection of an antibody that specifically binds a first CXCR-4 homolog but which does not specifically bind a different CXCR-4 homolog, one can select on the basis of positive binding to the first. CXCR-4 homolog and a lack of binding to the second CXCR-4 homolog.

Antibodies specific to a domain of a CXCR-4 protein are also provided.

The foregoing antibodies can be used in methods known in the art relating to the localization and activity of the CXCR-4 protein sequences of the invention, e.g., for imaging these proteins, measuring levels thereof in appropriate physiological samples, in diagnostic methods, etc.

In another embodiment of the invention (see infra), anti-CXCR-4 antibodies and fragments thereof containing the binding domain are Therapeutics.

Antibodies and antigen-binding antibody fragments may also be conjugated to a heterologous protein or peptide by chemical conjugation or recombinant DNA technology. The resultant chimeric protein possesses the antigen-binding specificity of the antibody and the function of the heterologous protein. For example, a polynucleotide encoding the antigen binding region of an antibody specific for the extracellular domain of CXCR-4 can be genetically fused to a coding sequence for the zeta chain of the T cell receptor. After expressing this construct in T cells, the T cells are expanded ex vivo and infused into a brain cancer patient. T cells expressing this chimeric protein are specifically directed to tumors that express CXCR-4 as a result of the antibody binding specificity and cause tumor cell killing. Alternatively, an antibody is fused to a protein which induces migration of leukocytes or has an affinity to attract other compounds to a tumor cite. A specific protein of this type is streptavidin. The binding of a streptavidin conjugated antibody to a tumor cell can be followed by the addition of a biotinylated drug, toxin or radioisotope to cause tumor specific killing.

Kits for use with such in vitro tumor localization and therapy methods containing the monoclonal antibodies (or fragments thereof) conjugated to any of the above types of substances can be prepared. The components of the kits can be packaged either in aqueous medium or in lyophilized form. When the monoclonal antibodies (or fragments thereof) are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

5.2.5. CXCR-4 Proteins Derivatives and Analogs

The invention further encompasses compositions comprising CXCR-4 proteins, and derivatives (including but not limited to fragments) and analogs of CXCR-4 proteins, in particular, those derivatives which act as antagonists of CXCR-4 activity. Nucleic acids encoding CXCR-4 protein derivatives and protein analogs are also provided. In one embodiment, the CXCR-4 proteins are encoded by the CXCR-4 nucleic acids described in Section 5.2.1. supra. In particular aspects, the proteins, derivatives, or analogs are of CXCR-4 proteins of animals, e.g., fly, frog, mouse, rat, pig, cow, dog, monkey, human, or of plants.

The production and use of derivatives and analogs related to CXCR-4 are within the scope of the present invention. In a specific embodiment, the derivative or analog is functionally active, i.e., capable of exhibiting one or more functional activities associated with a full-length, wild-type CXCR-4 protein. As one example, such derivatives or analogs which have the desired immunogenicity or antigenicity can be used, for example, in immunoassays, for immunization, for inhibition of CXCR-4 activity, etc. Derivatives or analogs that retain, or alternatively lack or inhibit, a desired CXCR-4 property of interest (e.g., binding to CXCR-4 binding partner, promotion of cell proliferation), can be used as inducers, or inhibitors, respectively, of such property and its physiological correlates. A specific embodiment relates to a CXCR-4 fragment that can be bound by an anti-CXCR-4 antibody. Derivatives or analogs of CXCR-4 can be tested for the desired activity by procedures known in the art, including but not limited to the assays described in Sections 5.3 and 5.5.

In particular, CXCR-4 derivatives can be made by altering CXCR-4 sequences by substitutions, additions or deletions that provide for functionally equivalent molecules. Due to the degeneracy of nucleotide coding sequences, other DNA sequences which encode substantially the same amino acid sequence as a CXCR-4 gene may be used in the practice of the present invention. These include but are not limited to nucleotide sequences comprising all or portions of CXCR-4 genes which are altered by the substitution of different codons that encode a functionally equivalent amino acid residue within the sequence, thus producing a silent change. Likewise, the CXCR-4 derivatives of the invention include, but are not limited to, those containing, as a primary amino acid sequence, all or part of the amino acid sequence of a CXCR-4 protein including altered sequences in which functionally equivalent-amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspaxtic acid and glutamic acid.

In a specific embodiment of the invention, proteins consisting of or comprising a fragment of a CXCR-4 protein consisting of at least 10 (continuous) amino acids of the CXCR-4 protein is provided. In other embodiments, the fragment consists of at least 20 or 50 amino acids of the CXCR-4 protein. In specific embodiments, such-fragments are not larger than 35, 100 or 200 amino acids. Derivatives or analogs of CXCR-4 include but are not limited to those molecules comprising regions that are substantially homologous to CXCR-4 or fragments thereof (e.g., in various embodiments, at least 60% or 70% or 800 or 900 or 9596 identity over an amino acid sequence of identical size or when compared to an aligned sequence in which the alignment is done by a computer homology program known in the art) or whose encoding nucleic acid is capable of hybridizing to a coding CXCR-4 sequence, under stringent, moderately stringent, or nonstringent conditions.

The CXCR-4 derivatives and analogs of the invention can be produced by various methods known in the art. The manipulations which result in their production can occur at the gene or protein level. For example, the cloned CXCR-4 gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequence can be cleaved at appropriate sites with restriction endonuclease(s), followed by further enzymatic modification if desired, isolated., and ligated in vitro. In the production of the gene encoding a derivative or analog of CXCR-4, care should be taken to ensure that the modified gene remains within the same translational reading frame as CXCR-4, uninterrupted by translational stop signals, in the gene region where the desired CXCR-4 activity is encoded.

Additionally, the CXCR-4-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for muCagenesis known in the art can be used, including but not limited to, chemical mutagenesis, in vitro site-directed mutagenesis (Hutchinson, C., et al., 1978, J. Biol. Chem. 253:6551, use of TABQ linkers (Pharmacia), etc.

Manipulations of the CXCR-4 sequence may also be made at the protein level. Included within the scope of the invention are CXCR-4 protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH; acetylation, formylation, oxidation, reduction; metabolic synthesis in the presence of tunicamycin; etc.

In addition, analogs and derivatives of CXCR-4 can be chemically synthesized. For example, a peptide corresponding to a portion of a CXCR-4 protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the CXCR-4 sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoroamino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the CXCR-4 derivative is a chimeric, or fusion, protein comprising a CXCR-4 protein or fragment thereof (preferably consisting of at least a domain or motif of the CXCR-4 protein, or at least 10 amino acids of the CXCR-4 protein) joined at its amino- or carboxy-terminus via a peptide bond to an amino acid sequence of a different protein. In one embodiment, such a chimeric protein is produced by recombinant expression of a nucleic acid encoding the protein (comprising a CXCR-4-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in. the art. Alternatively, such a chimeric product may be made by protein synthetic techniques, e.g., by use of a peptide synthesizer. Chimeric genes comprising portions of CXCR-4 fused to any heterologous protein-encoding sequences may be constructed. A specific embodiment relates to a chimeric protein comprising a fragment of CXCR-4 of at least six amino acids.

In another specific embodiment, the CXCR-4 derivative is a molecule comprising a region of homology with a CXCR-4 protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a CXCR-4 domain or a portion thereof.

Other specific embodiments of derivatives and analogs are described in the subsections below and examples sections infra.

5.3. Assays of CXCR-4 Proteins, Derivatives and Analogs

The functional activity of CXCR-4 proteins, derivatives and analogs can be assayed by various methods.

For example, in one embodiment, where one is assaying for the ability to bind or compete with wild-type CXCR-4 for binding to anti-CXCR-4 antibody, various immunoassays known in the art can be used, including but not limited to competitive and non-competitive assay systems using techniques such as radio immunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a CXCR-4-binding protein is identified, the binding can be assayed, e.g., by means well-known in the art. In another embodiment, physiological correlates of CXCR-4 binding to its substrates (signal transduction) can be assayed.

In addition, assays that can be used to detect or measure the ability to inhibit, or alternatively promote, cell proliferation are described in Section 5.4.

Other methods will be known to the skilled artisan and are within the scope of the invention.

5.4. Diagnosis and Screening

CXCR-4 proteins, analogs, derivatives, and subsequences thereof, CXCR-4 nucleic acids (and sequences complementary thereto), anti-CXCR-4 antibodies, have uses in diagnostics. Such molecules can be used in assays, such as immunoassays, to detect, prognose, diagnose, or monitor various conditions, diseases, and disorders affecting CXCR-4 expression, or monitor the treatment thereof. In particular, such an immunoassay is carried out by a method comprising contacting a sample derived from a patient with an anti-CXCR-4 antibody under conditions such that immunospecific binding can occur, and detecting or measuring the amount of any immunospecific binding by the antibody. In a specific aspect, such binding of antibody, in tissue sections, can be used to detect aberrant CXCR-4 localization or aberrant (e.g., high, low or absent) levels of CXCR-4. In a specific embodiment, antibody to CXCR-4 can be used to assay in a patient tissue or serum sample for the presence of CXCR-4 where an aberrant level of CXCR-4 is an indication of a diseased condition. By "aberrant levels," is meant increased or decreased levels relative to that present, or a standard level representing that present, in an analogous sample from a portion of the body or from a subject not having the disorder. In a specific embodiment, antibody to CXCR-4 can be used to assay and screen tissues or bodily fluids including but not limited to spinal fluid and brain tissue for elevated levels of CXCR-4 expression indicative of a tumor.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

CXCR-4 genes and related nucleic acid sequences and subsequences, including complementary sequences, can also be used in hybridization assays. CXCR-4 nucleic acid sequences, or subsequences thereof comprising about at least 8 nucleotides, can be used as hybridization probes.

Hybridization assays can be used to detect, prognose, diagnose, or monitor conditions, disorders, or disease states associated with aberrant changes in CXCR-4 expression and/or activity as described supra. In particular, such a hybridization assay is carried out by a method comprising contacting a sample containing nucleic acid with a nucleic acid probe capable of hybridizing to CXCR-4 DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting increased levels of CXCR-4 protein, CXCR-4 RNA, or CXCR-4 functional activity or by detecting mutations in CXCR-4 RNA, DNA or protein (e.g., translocations in CXCR-4 nucleic acids, truncations in the CXCR-4 gene or protein, changes in nucleotide or amino acid sequence relative to wild-type CXCR-4) that cause increased expression or activity of CXCR-4. Such diseases and disorders include but are not limited to those tumors or tissue types mentioned in Section 6 in which CXCR-4 is overexpressed. By way of example, levels of CXCR-4 protein can be detected by immunoassay, levels of CXCR-4 RNA can be detected by hybridization assays (e.g., Northern blots, dot blots), translocations and point mutations in CXCR-4 nucleic acids can be detected by Southern blotting, RFLP analysis, PCR using primers that preferably generate a fragment spanning at least most of the CXCR-4 gene, sequencing of the CXCR-4 genomic DNA or cDNA obtained from the patient, etc.

In a preferred embodiment, levels of CXCR-4 mRNA or protein in a patient sample are detected or measured, in which increased levels indicate that the subject has, or has a predisposition to developing, a malignancy or hyperproliferative disorder; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of CXCR-4 protein, CXCR-4 RNA, or CXCR-4 functional activity, or by detecting mutations in CXCR-4 RNA, DNA or protein (e.g., translocations in CXCR-4 nucleic acids, truncations in the gene or protein, changes in nucleotide or amino acid sequence relative to wild-type CXCR-4) that cause decreased expression or activity of CXCR-4. Such diseases and disorders include but are not limited to those tumors and tissue types mentioned in Section 6 and its subsections in which CXCR-4 is overexpressed. By way of example, levels of CXCR-4 protein, levels of CXCR-4 RNA, CXCR-4 binding activity, and the presence of translocations or point mutations can be determined as described above.

In a specific embodiment, levels of CXCR-4 mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

Kits for diagnostic use are also provided, that comprise, in one or more containers, an anti-CXCR-4 antibody, and, optionally, a labeled binding partner to the antibody. Alternatively, the anti-CXCR-4 antibody can be labeled (with a detectable marker, e.g., a chemiluminescent, enzymatic, fluorescent, or radioactive moiety). A kit is also provided that comprises, in one or more containers, a nucleic acid probe capable of hybridizing to CXCR-4 RNA. In a specific embodiment, a kit can comprise in one or more containers a pair of primers (e.g., each in the size range of 6-30 nucleotides) that are capable of priming amplification [e.g., by polymerase chain reaction (see, e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a; CXCR-4 nucleic acid. A kit can optionally further comprise, in a container, a predetermined amount of a purified CXCR-4 protein or nucleic acid, e.g., for use as a standard or control.

5.5. Therapeutic Uses

The invention provides for treatment or prevention of various diseases and disorders by administration of a therapeutic compound (termed herein "Therapeutic"). Such "Therapeutics" include but are not limited to: CXCR-4 proteins and analogs and derivatives (including fragments) thereof (e.g., as described hereinabove); antibodies thereto (as described hereinabove); nucleic acids encoding the CXCR-4 proteins, analogs, or derivativesas described hereinabove); CXCR-4 antisense nucleic acids, and CXCR-4 agonists and antagonists. Disorders involving tumorigenesis or cell overproliferation are treated or prevented by administration of a Therapeutic that antagonizes CXCR-4 function. Disorders in which cell proliferation is deficient or is desired are treated or prevented by administration of a Therapeutic that promotes CXCR-4 function. See details in the subsections below.

Generally, it is preferred to administer a product of a species origin or species reactivity (in the case of antibodies) that is the same as that of the recipient. Thus, in a preferred embodiment, a human CXCR-4 protein (SEQ ID NO:2), derivative, or analog, or nucleic acid (SEQ ID NO:1) or an antibody to a human CXCR-4 protein, is therapeutically or prophylactically administered to a human patient.

Additional descriptions and sources of Therapeutics that can be used according to the invention are found in Sections 5.1 through 5.7 herein.

5.5.1. Treatment and Prevention of Disorders Involving Over Proliferation of Cells Diseases and disorders involving cell overproliferation are treated or prevented by administration of a Therapeutic that antagonizes (i.e., inhibits) CXCR-4 function. Examples of such a Therapeutic include but are not limited to CXCR-4 antibodies, CXCR-4 antisense nucleic acids, derivatives, or analogs that are functionally active, particularly that are active in inhibiting cell proliferation (e.g., as demonstrated in in vitro assays or in animal models or in *Drosophila*). Other Therapeutics that can be used, e.g., CXCR-4 antagonists, can be identified using in vitro assays or animal models, examples of which are described infra.

In specific embodiments, Therapeutics that inhibit CXCR-4 function are administered therapeutically (including prophylactically); (1) in diseases or disorders involving an increased (relative to normal or desired) level of CXCR-4 protein or function, for example, in patients where CXCR-4 protein is overexpressed, genetically defective, or biologically hyperactive; or (2) in diseases or disorders wherein in vitro (or in vivo) assays (see infra) indicate the utility of CXCR-4 antagonist administration. The increased level in CXCR-4 protein or function can be readily detected, e.g., by obtaining a patient tissue sample (e.g., from biopsy tissue) and assaying it in vitro for RNA or protein levels, structure and/or activity of the expressed CXCR-4 RNA or protein. Many methods standard in the art can be thus employed, including but not limited to immunoassays to detect and/or visualize CXCR-4 protein (e.g., Western blot, immunoprecipitation followed by sodium dodecyl sulfate polyacrylamide gel electrophoresis, immunocytochemistry, etc.) and/or hybridization assays to detect CXCR-4 expression by detecting and/or visualizing CXCR-4 mRNA (e.g., Northern assays, dot blots, in situ hybridization, etc.), etc. Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.5.1.1. Malignancies

Malignancies and related disorders that can be treated or prevented by administration of a Therapeutic that inhibits CXCR-4 function include but are not limited to those listed in Table I (for a review of such disorders, see Fishman et al., 1985, Medicine, 2d Ed., J.B. Lippincott Co., Philadelphia).

Table 1

Malignancies and Related Disorders

Leukemia
acute leukemia
   acute lymphocytic leukemia
   acute lymphoblastic leukemia
   acute myelocytic leukemia
     myeloblastic
     myelogenous
     promyelocytic
     myelomonocytic
     monocytic
     erythroleukemia
chronic leukemia
   chronic myelocytic (granulocytic) leukemia
   chronic myelogenous leukemia
   chronic lymphocytic leukemia
Polycythemia vera
Lymphoma
   Hodgkin's disease
   non-Hodgkin's disease
Multiple myeloma
Waldenstrom's macroglobulinemia
Heavy chain disease
Solid tumors
   sarcomas and carcinomas
     adenocarcinoma
     fibrosarcoma
     myxosarcoma
     liposarcoma
     chondrosarcoma
     osteogenic sarcoma
     chordoma
     angiosarcoma
     endotheliosarcoma
     lymphangiosarcoma
     lymphangioendotheliosarcoma
     synovioma
     mesothelioma
     Ewing's tumor
     leiomyosarcoma
     rhabdomyosarcoma
     colon carcinomacolorectal adenocarcinoma
     colon tumor metastatic to brain
     lung carcinoma
     pancreatic cancer breast cancer
     ovarian cancer
     prostate cancer
     squamous cell carcinoma
     basal cell carcinoma
     adenocarcinoma
     sweat gland carcinoma
     sebaceous gland carcinoma
     papillary carcinoma
     papillary adenocarcinomas
     cystadenocarcinoma
     medullary carcinoma
     bronchogenic carcinoma
     renal cell carcinoma hepatoma
     bile duct carcinoma choriocarcinoma
     seminoma
     embryonal carcinoma
     Wilms' tumor
     cervical cancer
     uterine cancer
     testicular tumor
     lung carcinoma
     small cell lung carcinoma
     bladder carcinoma
     epithelial carcinoma
     glioblastoma
     gliomas
     astrocytomas
     medulloblastoma
     craniopharyngioma
     ependymoma
     pinealoma
     hemangioblastoma
     acoustic neuroma
     oligodendroglioma
     meningiomas
     melanoma
     neuroblastoma
     retinoblastoma In specific embodiments, malignancy or dysproliferative changes (such as metaplasias and dysplasias), or hyperproliferative disorders, are treated or prevented in the brain, breast, colon, prostate, lung, or skin. In other specific embodiments, carcinoma, melanoma, or leukemia is treated or prevented.

5.5.1.2. Premalignant Conditions

The Therapeutics of the invention that antagonize CXCR-4 activity can also be administered to treat premalignant conditions and to prevent progression to a neoplastic or malignant state; including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that inhibits CXCR-4 function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype.).

In a specific embodiment, leukoplakia, a benign-appearing hyperplastic or dysplastic lesion of the epithelium, or Bowen's disease, a carcinoma in situ, are preneoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.).

In another specific embodiment, a Therapeutic of the invention is administered to a human patient to prevent progression to brain, breast, colon, prostate, lung, or skin. In other specific embodiments, carcinoma, melanoma, or leukemia is treated or prevented.

5.5.1.3. Gene Therapy

In a specific embodiment, anti-sense nucleic acids complementary to a sequence encoding a CXCR-4 protein or functional derivative thereof, are administered to inhibit CXCR-4 function, by way of gene therapy. Gene therapy refers to therapy performed by the administration of a nucleic acid to a subject. In this embodiment of the invention, the antisense nucleic acid mediates a therapeutic effect by inhibiting CXCR-4 transcription and translation.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTEC14 11(5), 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one embodiment, the Therapeutic comprises an CXCR-4 sense or antisense nucleic acid that is part of an expression vector that expresses a CXCR-4 protein or fragment or chimeric protein thereof in a suitable host. In particular, such a nucleic acid has a promoter operably linked to the CXCR-4 coding region, said promoter being inducible or constitutive, and, optionally, tissue-specific. In another particular embodiment, a nucleic acid molecule is used in which the CXCR-4 coding sequences and any other desired sequences are flanked by regions that promote homologous recombination at a desired site in the genome, thus providing for intrachromosomal expression of the CXCR-4 nucleic acid (Koller and Smithies, 1989, Proc. Nat'l Acad. Sci. USA 86:8932-8935; Zijlstra et al., 1989, Nature 342:435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, a nucleic acidligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Nat'l Acad. Sci. USA 86:8932-8935; Zijlstra et al., 1989, Nature 342:435-438).

In a specific embodiment, a viral vector that contains the CXCR-4 nucleic acid is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The CXCR-4 nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin.

Invest. 93:644-651; Kiem et al., 1994, Blood 83:1467-1473; Salmons and Gunzberg, 1993, Human Gene Therapy 4:129-141; and Grossman and Wilson, 1993, Cum Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et. al., 1993, J. Clin. Invest. 91:225-234.

Adeno-associated virus (AAV) has also been proposed for use in gene therapy (Walsh et al., 1993, Proc. Soc. Exp. Biol. Med. 204:289-300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired affect, patient state, etc., and can be determined by one Skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a CXCR-4 nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include, but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973-985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1985, Mayo Clinic Proc. 91:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Nat'l Acad. Sci. USA 79:3608-3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Additional methods that can be adapted for use to deliver a nucleic acid encoding a CXCR-4 protein or functional derivative thereof are described in Section 5.5.2.2.2.

5.5.2. Treatment and Prevention of Hyperproliferative and Dysproliferative Disorders Diseases and disorders involving an increase in cell proliferation (growth) or in which cell proliferation is otherwise undesirable, are treated or prevented by administration of a Therapeutic that antagonizes (inhibits) CXCR-4 function. Therapeutics that can be used include but are not limited to anti-CXCR-4 antibodies (and fragments and derivatives thereof containing the binding region thereof), CXCR-4 antisense nucleic acids, and CXCR-4 nucleic acids that are dysfunctional (e.g., due to a heterologous (non-CXCR-4 sequence) insertion within the CXCR-4 coding sequence) that are used to "knockout" endogenous CXCR-4 function by homologous recombination (see, e.g., Capecchi, 1989, Science 244:1288-1292). In a specific embodiment of the invention, a nucleic acid containing a portion of a CXCR-4 gene in which CXCR-4 sequences flank (are both 5' and 3' to) a different gene sequence, is used, as a CXCR-4 antagonist, to promote CXCR-4 inactivation by homologous recombination (see also Koller and Smithies, 1989, Proc. Nat'l Acad. Sci. USA 86:8932-8935; Zijistra et al., 1989, Nature 342: 435-438). Therapeutics that inhibit CXCR-4 function can be identified by use of known convenient in vitro assays, e.g., based on their ability to inhibit binding of CXCR-4 to another protein or inhibit any known CXCR-4 function, as preferably assayed in vitro or in cell culture, although genetic assays in *Drosophila* or another species may also be employed. Preferably, suitable in vitro or in vivo assays, are utilized to determine the effect of a specific Therapeutic and whether its administration is indicated for treatment of the affected tissue.

In specific embodiments, Therapeutics that inhibit CXCR-4 function are administered therapeutically (including prophylactically): (1) in diseases or disorders involving an increased (relative to normal or desired) level of CXCR-4 protein or function, for example, in patients where CXCR-4 protein is overactive or overexpressed; or (2) in diseases or disorders wherein in vitro (or in vivo) assays (see infra) indicate the utility of CXCR-4 antagonist administration. The increased levels in CXCR-4 protein or function can be readily detected, e.g., by quantifying protein and/or RNA, by obtaining a patient tissue sample (e.g., from biopsy tissue) and assaying it in vitro for RNA or protein levels, structure and/or activity of the expressed CXCR-4 RNA or protein. Many methods standard in the art can be thus employed, including but not limited to immunoassays to detect and/or visualize CXCR-4 protein (e.g., Western blot, immunoprecipitation followed by sodium dodecyl sulfate polyacrylamide gel electrophoresis, immunocytochemistry, etc.) and/or hybridization assays to detect CXCR-4 expression by detecting and/or visualizing, respectively, CXCR-4 mRNA (e.g., Northern assays, dot blots, in situ hybridization, etc.), etc.

In other embodiments, chemical mutagenesis, or homologous recombination with an insertionally inactivated CXCR-4 gene (see Capecchi, 1989, Science 244:1288-1292 and Section 5.14 infra) can be carried out to reduce or destroy endogenous CXCR-4 function, in order to decrease cell proliferation. Suitable methods, modes of administration and compositions, that can be used to inhibit CXCR-4 function are described in Sections 5.5.2 through 5.5.2.1.2, above.

In an embodiment of the invention, a Therapeutic that inhibits CXCR-4 activity is used to treat or prevent hyperproliferative or benign dysproliferative disorders. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.5.2.1. Antisense Regulation of CXCR-4 Expression

In a specific embodiment, CXCR-4 function is inhibited by use of CXCR-4 antisense nucleic acids. The present invention provides the therapeutic or prophylactic use of nucleic acids of at least six nucleotides that are antisense to a gene or cDNA encoding CXCR-4 or a portion thereof. A CXCR-4 antisense nucleic acid as used herein refers to a nucleic acid capable of hybridizing to a portion of a CXCR-4 RNA (preferably mRNA) by virtue of some sequence complementarity. The antisense nucleic acid may be complementary to a coding and/or noncoding region of a CXCR-4 mRNA. Such antisense nucleic acids have utility as Therapeutics that inhibits CXCR-4 function, and can be used in the treatment or prevention of disorders as described supra in Section 5.5.2 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the CXCR-4 antisense nucleic acids provided by the instant invention can be used to prevent tumors or other forms of aberrant cell proliferation.

The invention further provides pharmaceutical compositions comprising an effective amount of the CXCR-4 antisense nucleic acids of the invention in a pharmaceutically acceptable carrier, as described infra.

In another embodiment, the invention is directed to methods for inhibiting the expression of a CXCR-4 nucleic acid sequence in a prokaryotic or eukaryotic cell comprising providing the cell with an effective amount of a composition comprising an CXCR-4 antisense nucleic acid of the invention. CXCR-4 antisense nucleic acids and their uses are described in detail below.

5.5.2.1.1. CXCR-4 Antisense Nucleic Acids

The CXCR-4 antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Nat'l Acad. Sci. U.S.A. 86:6553-6556; Lemaitre et al., 1987, Proc. Nat'l Acad. Sci. 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549).

In a preferred aspect of the invention, a CXCR-4 antisense oligonucleotide is provided, preferably of single-stranded DNA. The oligonucleotide may be modified at any position on its structure with substituents generally known in the art.

The CXCR-4 antisense oligonucleotide may comprise it least one modified base moiety which is selected from the group including but not limited to 5-fluorouracil, 5-bromouracil, 5-chlorouracil, 5-iodouracil, hypoxanthine, Xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including but not limited to arabinose, 2-fluoroarabinose, xylulose, and hexose.

In yet another. embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual O-units, the strands run parallel to each other (Gautier et al., 1987, Nucl. Acids Res. 15:6625-6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Nat'l Acad. Sci. U.S.A. 85:7448-7451), etc.

In a specific embodiment, the CXCR-4 antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-O-methylribonucleotide (Inoue et al., 1987, Nucl. Acids Res. 15:6131-6148), or a chimeric RNA-DNA analog (Inoue et al., 1987, FEES Lett. 215:327-330).

In an alternative embodiment, the CXCR-4 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the CXCR-4 antisense nucleic acid. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the CXCR-4 antisense RNA can be by any promoter known in the art to act in mammalian, preferably human cells. Such promoters can be inducible or constitutive.

Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Nat'l Acad. Sci. U.S.A. 78:1441-1445), the regulatory sequences of the metallothionein gene (Brinster et al., 1982, Nature 296:39-42), etc.

The antisense nucleic acids of the invention comprise a sequence complementary to at least a portion of an RNA transcript of a CXCR-4 gene, preferably a human CXCR-4 gene (SEQ ID NO:1). However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded CXCR-4 antisense nucleic acids, a single strand of the duplex may thus be tested, or triplex formation may be assayed. The ability to hybridize will depend on both the degree of complementarity and the length of the antisense nucleic acid. Generally, the longer the hybridizing nucleic acid, the more base mismatches with a CXCR-4 RNA it may contain and still form a stable duplex (or triplex, as the case may be). One skilled in the art can ascertain a tolerable degree of mismatch by use of standard procedures to determine the melting point of the hybridized complex.

5.5.2.1.2. Therapeutic Use of CXCR-4 Antisense Nucleic Acids

The CXCR-4 antisense nucleic acids can be used to treat (or prevent) disorders of a cell type that expresses, or preferably overexpresses, CXCR-4. In a specific embodiment, such a disorder is a hyperproliferative disorder, e.g., tumorigenesis. In a preferred embodiment, a single-stranded DNA antisense CXCR-4 oligonucleotide is used.

Cell types which express or overexpress CXCR-4 RNA can be identified by various methods known in the art. Such methods include but are not limited to hybridization with a CXCR-4-specific nucleic acid (e.g., by Northern hybridization, dot blot hybridization, in situ hybridization), observing the ability of RNA from the cell type to be translated in vitro into CXCR-4, immunoassay, etc. In a preferred aspect, primary tissue from a patient can be assayed for CXCR-4 expression prior to treatment, e.g., by immunocytochemistry or in situ hybridization.

Pharmaceutical compositions of the invention (see Section 5.10), comprising an effective amount of a CXCR-4 antisense nucleic acid in a pharmaceutically acceptable carrier, can be administered to a patient having a disease or disorder which is of a type that expresses or overexpresses CXCR-4 RNA or protein.

The amount of CXCR-4 antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising CXCR-4 antisense nucleic acids are administered via liposomes, microparticles, or microcapsules. In various embodiments of the invention, it may be useful to use such compositions to achieve sustained release of the CXCR-4 antisense nucleic acids. In a specific embodiment, it may be desirable to utilize liposomes targeted via antibodies to specific identifiable tumor antigens (Leonetti et al., 1990, Proc. Nat'l Acad. Sci. U.S.A. 87:2448-2451; Renneisen et al., 1990, J. Biol. Chem. 265:16337-16342). Additional methods that can be adapted for use to deliver a CXCR-4 antisense nucleic acid are described in Section 5.9.1.4.

5.6. Demonstration of Therapeutic or Prophylactic Utility

The Therapeutics of the invention are preferably tested in vitro, and then in vivo for the desired therapeutic or prophylactic activity, prior to use in humans.

For example, in vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described herein.

In another specific embodiment, a Therapeutic is indicated for use in treating cell injury or a degenerative disorder which exhibits in vitro promotion of growth/proliferation of cells of the affected patient type.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 435-446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.7 Therapeutic/Prophylactic Administration and Compositions

The invention provides methods of treatment (and prophylaxis) by administration to a subject of an effective amount of a Therapeutic of the invention, in a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429-4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

In addition, it may be desirable to introduce a Therapeutic of the invention into the central nervous system by any suitable route, including, but not limited to intraventricular and intrathecal injection. Intraventricular injection may be facilitated by an intraventricular catheter, for example, attached to a reservoir, such as an Ommaya reservoir. Agents which enhance the delivery of chemotherapeutics to brain tumors, such as agonists which activate specific receptors on endothelial cells which regulate permeability, including, e.g., bradykinin agonists (see, e.g., Elliott, et al., 1996, Cancer Research 56:3998-4005) tumor angiogenesis factors (Cserr and Knopf, 1992, Immunol Today 1:507-512), etc., can be used in formulations and methods of administration when the Therapeutic is intended for delivery to a tumor of the central nervous system.

In a specific embodiment, injection into spinal fluid, and/or procedures utilizing an Ommaya reservoir, can be used to introduce a therapeutic of the invention such as an anti- CXCR-4 antibody, e.g., a bispecific anti-CXCR-4 antibody, directly into the central nervous system for immunotherapy of a tumor.

In yet another specific embodiment, an anti-CXCR-4 antibody, e.g., a bispecific anti-CXCR-4 antibody, is employed as a Therapeutic in an immunotherapeutic treatment of a non-brain tumor and is infused into a recipient intravenously.

Immune cells, e.g., dendritic cells or cytotoxic T-cells, can cross the blood-brain barrier and have access to brain tissue, especially in the presence of tumor angiogenesis factors (Cserr and Knopf, 1992, Immunol. Today, 12:507-512). In a preferred embodiment, activated dendritic cells (HLA-matched to the recipient) (see generally, Tjoa et al., 1996, Prostate 28:65-69) that have been exposed to a CXCR-4 protein, analog or derivative thereof are infused into a recipient under conditions that permit their crossing the blood-brain barrier, e.g., in the presence of tumor angiogenesis factors. In another preferred embodiment, activated cytotoxic T-cells (HLA-matched to the recipient) (see generally, Tjoa et al., 1996, Prostate 28:65-69) that have been exposed ex vivo (i.e., in vitro) to a CXCR-4 protein, analog, or derivative thereof are infused into a recipient under conditions that permit their crossing the blood-brain barrier.

In yet another specific embodiment, a Therapeutic of the invention; e.g., activated dendritic cells that have been exposed to a CXCR-4 protein, analog or derivative thereof, or activated cytotoxic T-cells that have been exposed ex vivo dendritic cells that have been exposed to a CXCR-4 protein, analog, or derivative thereof, is administered for the treatment of a non-brain tumor.

Pulmonary administration of a Therapeutic can also be employed, e.g., by use of an inhaler or nebulizer; and formulation with an aerosolizing agent.

In a specific embodiment, it may be desirable to administer the Therapeutic of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, 1990 Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985 Science 228:190; During et al., 1989 Ann. Neurol. 25:351; Howard et al., 1989 J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984))

Other controlled release systems are discussed in the review by Langer (Science 249:1527-1533 (1990))

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,285), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Nat'l Acad. Sci. USA 88:1854-1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.7.1. Treatment and Prevention of Hypoproliferative Disorders

Diseases and disorders involving decreased cell proliferation or in which cell proliferation is desired for treatment or prevention, and that can be treated or prevented by promoting CXCR-4 function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

Lesions which may be treated according to the present invention include but are not limited to the following lesions
  (i) traumatic lesions, including lesions caused by physical injury or associated with surgery;
  (ii) ischemic lesions, in which a lack of oxygen results in cell injury or death, e.g., myocardial or cerebral infarction or ischemia, or spinal cord infarction or ischemia;
  (iii) malignant lesions, in which cells are destroyed or injured by malignant tissue;
  (iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;
  (v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;
  (vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;
  (vii) lesions associated with systemic diseases including but not limited to diabetes or systemic lupus erythematosus;
  (viii) lesions caused by toxic substances including alcohol, lead, or other toxins; and
  (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Nervous system lesions which may be treated in a patient (including human and non-human mammalian patients) according to the invention include but are not limited to the lesions of either the central (including spinal cord, brain) or peripheral nervous systems.

Therapeutics which are useful according to this embodiment of the invention for treatment of a disorder may be selected by testing for biological activity in promoting the survival or differentiation of cells (see also Section 5.9). For example, in a specific embodiment relating to therapy of the nervous system, a Therapeutic which elicits one of the following effects may he useful according to the invention:
  (i) increased sprouting of neurons in culture or in vivo;
  (ii) increased production of a neuron-associated molecule in culture or in vivo, e.g., choline acetyltransferase or acetylcholinesterase with respect to motor neurons; or
  (iii) decreased symptoms of neuron dysfunction in vivo.

Such effects may be measured by any method known in the art. In preferred, non-limiting embodiments, increased sprouting of neurons may be detected by methods set forth in Pestronk et al. (1980, Exp. Neurol. 70:65-82) or Brown et al. (1981, Ann. Rev. Neurosci. 4:17-42); and increased production of neuron-associated molecules may be measured by bioassay, enzymatic assay, antibody binding, Northern blot assay, etc., depending on the molecule to be measured.

5.8. Additional Use of Increased CXCR-4 Function to Promote Increased Growth

Promotion of CXCR-4 Function (e.g., by administering a compound that promotes CXCR-4 function as described above), has utility that, is not limited to therapeutic or prophylactic applications. For example, CXCR-4 function can be promoted in order to increase growth of animals (e.g., cows, horses, pigs, goats, deer, chickens) and plants (particularly edible plants, e.g., tomatoes, melons, lettuce, carrots, potatoes, and other vegetables), particularly those that are food or material sources. In an embodiment in which a CXCR-4 nucleic acid is under the control of a tissue-specific promoter, the invention can be used in plants or animals to increase growth where desired (e.g., in the fruit or muscle). For example, a CXCR-4 nucleic acid under the control of a temperature-sensitive promoter can be administered to a plant or animal, and the desired portion of the (or the entire) plant or animal can be subjected to heat in order to induce CXCR-4 nucleic acid production, resulting in increased CXCR-4 expression, and resulting cell proliferation. Methods to make plants recombinant are commonly known in the art and can be used. Regarding methods of plant transformation (e.g., for transformation with a CXCR-4 antisense nucleic acid), see, e.g., Valvekens et al., 1988, Proc. Nat'l Acad. Sci. USA. 85:5536-5540. Regarding methods of targeted gene inactivation in plants (e.g., to inactivate CXCR-4), see, e.g., Miao and Lam, 1995, The Plant J. 7:359-365.

Promotion of CXCR-4 function can also have uses in vitro, e.g., to expand cells in vitro, including but not limited to stem cells, progenitor cells, muscle cells, fibroblasts, liver cells, etc., e.g., to grow cells/tissue in vitro prior to administration to a patient (preferably a patient from which the cells were derived), etc.

5.9. Screening for CXCR-4 Agonists and Antagonists

CXCR-4 nucleic acids, proteins, and derivatives also have uses in screening assays to detect molecules that specifically bind to CXCR-4 nucleic acids, proteins, or derivatives and thus have potential use as agonists or antagonists of CXCR-4, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to CXCR-4 nucleic acids, proteins, or derivatives. For example, recombinant cells expressing CXCR-4 nucleic acids can be used to recombinantly produce CXCR-4 proteins in these assays, to screen for molecules that bind to a CXCR-4 protein. Molecules putative binding partners of CXCR-4) are contacted with the CXCR-4 protein (or fragment thereof) under conditions conducive to binding, and then molecules that specifically bind to the CXCR-4 protein are identified. Similar methods can be used to screen for molecules that bind to CXCR-4 derivatives or nucleic acids. Methods that can be used to carry out the foregoing are commonly known in the art.

By way of example, diversity libraries, such as random or combinatorial peptide or nonpeptide libraries can be screened for molecules that specifically bind to CXCR-4. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Nat'l Acad. Sci. USA 90:10922-10926; Erb et al., 1994, Proc. Nat'l Acad. Sci. USA 91:11422-11426; Houghten et al., 1992, Biotechniques 13:412; Jayawickreme et al., 1994, Proc. Nat'l Acad. Sci. USA 91:1614-1618; Salmon et al., 1993, Proc. Nat'l Acad. Sci. USA 90:11708-11712; PCT Publication No. WO 93/20242; and Brenner and Lerner, 1992, Proc. Nat'l Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152: 149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Nat'l Acad. Sci. USA 91:9022-9026.

By way of examples of nonpeptide libraries, a benzodiazepine library (see e.g., Bunin et al., 1994, Proc. Nat'l Acad. Sci. USA 91:4708-4712) can be adapted for use. Peptoid libraries (Simon et al., 1992, Proc. Nat'l Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Nat'l Acad. Sci. USA 91:11138-11142).

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Nat'l Acad. Sci. USA 89:5393-5397; Yu et al., 1994, Cell 76:933-945; Staudt et al., 1988, Science 241:577-580; Back et al., 1992, Nature 355:564-566; Tuerk et al., 1992, Proc. Nat'l Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and PCT Publication No. WO 94/18318.

In a specific embodiment, screening can be conducted out by contacting the library members with a CXCR-4 protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited hereinabove.

In another embodiment, the two-hybrid system for Selecting interacting proteins in yeast (Fields and Song, 1989, Nature 340:245-246; Chien et al., 1991, Proc. Nat'l Acad. Sci. USA 88:9578-9582) can be used to identify molecules that specifically bind to a CXCR-4 protein or derivative.

5.10. Animal Models

The invention also provides animal models. In one embodiment, animal models for diseases and disorders involving cell hypoproliferation (e.g., as described in Section 5.8.1) are provided. Such an animal can be initially produced by promoting homologous recombination between a CXCR-4 gene in its chromosome and an exogenous CXCR-4 gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated CXCR-4 gene, such that homologous recombination occurs, followed by injecting the ES cells into a blastocyst, and implanting the blastocyst into a foster mother, followed by the birth of the chimeric animal ("knockout animal") in which a CXCR-4 gene has been inactivated (see Capecchi, 1989, Science 244:1288-1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell hypoproliferation. Such animals can be used to screen, for or test molecules for the ability to promote proliferation and thus treat or prevent such diseases and disorders.

In a different embodiment of the invention, transgenic animals that have incorporated and express a functional CXCR-4 gene have use as animal models of diseases and disorders involving cell hyperproliferation or malignancy. Such animals are expected to develop or be predisposed to developing diseases or disorders involving cell hyperproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

6. Example

Isolation and Characterization of the CXCR-4 Gene Expression from Human Glioblastoma Multiforme Tumor Tissue In this study, the role of CXCR-4, a G protein coupled receptor in brain tumorigenesis was characterized.

6.1. Materials and Methods

Differential Hybridization of Human Atlas™ Expression Arrays

In order to identify genes altered during the genesis of human glioblastomas, the techniques of Different Display-PCR (DD-PCR) and differential hybridization of human cDNA expression arrays were utilized. (Examples of protocols of DD-PCR may be found in Sehgal et al., 1991, J. Surg. Oncol. 64:102-108; Sehgal et al., 1997, J. Surg. Oncol. 65:249-257; Sehgal et al., 1997, Int. J. Cancer 71:565-572; Sehgal et al., 1996, Exp. Lung. Res. 22:419-434)

The technique of Differential hybridization of Atlas™ human cDNA expression arrays was performed as in using the protocol recommended by Clonetech. Briefly, 10 µg of total RNA was isolated from human GMTT. Total RNA for NBT (normal brain tissue) was purchased from Clontech (Palo Alto, Calif.). 10 µg of total RNA from each tissue sample was treated with 5 µl of 2 units/µl of DNaseI for 30 minutes at 37° C. The first strand cDNA synthesis was carried out using oligo(dT) and random hexamer primers using the Advantage cDNA synthesis for PCR kit under the conditions recommended by Clonetech (Palo Alto, Calif.). An equal amount of GMTT or NBT cDNA (1×10$^6$ cpm/ml) was next hybridized to two identical Atlas™ Human cDNA expression array membranes in separate bags for 18 hours at 65° C. in express-hybridization solution from Clontech. Membranes were then washed and then exposed to X-ray film at −80° C. for 48 hours.

Gene Specific RT-PCR

Gene specific RT-PCR technique was carried out as described previously (Sehgal et al., 1997 J. Surg. Oncol. 64:102-108). CXCR-4 primers (5' CTCTCCAAAG-GAAAGCGAGGTGGACAT 3' (SEQ ID No.:8), 5' AGACT-GTACACTGTAGGTGCTGAAATCA 3' (SEQ ID NO.:9)) were used for carrying out PCR. PCR for D1-2 (a mitochondrial Cytochrome C oxidase subunit 1 gene, accession number D38112), a housekeeping gene was carried out using specific primers (5' CGGAGCAATATGAAATGATCT 3' (SEQ ID NO.: 10, 5' GCAAATACAGCTCCTATTG 3' (SEQ ID NO.:11). PCR was carried out using the conditions described in detail previously (Sehgal et al., 1997 J. Surg. Oncol. 64:102-108). The PCR product was then run on a 1.2% agarose gel. DNA was transferred on to Hybond N+magna-charge membrane (Amersham, Arlington Heights, Ill.) using the standard Southern blotting conditions as described previously (Sambrook et al., 1989 Cold Spring Harbour N.Y., Cold Spring Laboratory). Hybridization was using 1×10$^6$ cpm/ml gene specific probe at 42° C. for 18 hours. Gene specific probes were prepared by multiprime labeling the internal primers (CXCR-4, 5' ATCTGTTTCCACTGAGTCT-GATCTTCAAGTTTTCACCCAGCTAACACA 3' (SEQ ID NO.:27) and housekeeping gene D1-2,5' TAGGCCT-GACTGG CATTGTATTAGCAAACTCATCACTAGA 3' (SEQ ID No. 13)) using the megaprime labeling kit from Amersham (Arlington Heights, Ill.). D1-2 gene has been used in the past as a housekeeping gene in the RT-PCR application (Sehgal et al., 1997 J. Surg. Oncol. 64:102-105). Quantitation of Southern blots resulted from RT-PCR was performed using the ImageQuanNT™ volume quantitation program from the Molecular Dyamics Phosphor Imager. Volume quantitation calculates the volume under the surface created by a 3-D plot of pixel locations and pixel values. The volume (the integrated intensity of all the pixels in the spot excluding the background) of CXCR-4 bands in Southern blots were quantitated. These pixel values are then normalized with pixel valuates in the bands of housekeeping gene (D1-2 referred by letter H) and are shown as relative expression in FIG. 1. The subjective terms of "low," "medium" and "high," in text refer to relative expression and are based on CXCR-4 expression in NBT as "low" and in HTB16 and GB1690 as "high".

D1-2 gene has been used in the past as a housekeeping gene in the RT-PCR application (Sehgal et al., 1997 J. Surg. Oncol. 64:102-105).

Quantitation of Southern blots resulted from RT-PCR was performed using the ImageQuaN™ volume quantitation program from the molecular Dyamics Phosphor Imager. Volume quantitation calculates the volume under the surface created by a 3-D plot of pixel locations and pixel values. The volume (the integrated intensity of all the pixels in the spot excluding the background) of CXCR-4 bands in Southern blots was quantitated. These pixel values are then normalized with pixel values in the bands of housekeeping gene (D1-2 referred by letter H) and are shown as relative expression in FIG. 1. The subjective terms of "low," "medium" and "high," in text refer to relative expression and are based on CXCR-4 expression in NBT as "low" and in RT216 and GH1690 as "high".

In Situ Hybridization

The technique of In situ hybridization was done was described previously

Wilkinson, 1992 In Situ Hybridization, A practical approach. NY: Oxford University Press). Briefly, 6 µm formalin fixed, paraffin embedded human brain tumor sections were deparaffinized by 2 washes in xylene, followed by rehydration through graded concentrations of ethanol from 100% to 70%. These were then washed in PBS and treated with Proteinase K (25 mg/ml for 10 minutes), followed by fixation in 4% paraformaldehyde. After incubation in 0.25% acetic anhydride/0.1 M TEA (Tri-Ethyl Acetic acid), sections were dehydrated through graded concentrations of ethanol from 70% to 100% and prehybridized for 2 hours at 55° C. in 50% formamide, 5×SSC pH 4.5, 50 µmg/ml tRNA, 50 µg/ml heparin, and 1% SDS. Sections were hybridized with 1 µg/ml DIG (Digoxygenin) labeled antisense or sense probes for 18 hours at 55° C. Probes were synthesized with the Genius 4 kit (Boehringer Mannheim, Indianapolis, Ind.) using the T3 and T7 promoters of a PCR template derived from human CXCR-4 cDNA corresponding to bases 1061-1618. The PCR template was amplified using primers 5' CAAGCTCGAAAT-TAAAACCCTCACTAAAGGGCTCTC-CAAAGGAAAGCGAG GTGGACAT 3' (SEQ ID NO.:14)

and 5' CACTTAACTAATACGACTCACTATAGG-GAGACTGTACACTGTAGGTGCGAA ATCA 3' (SEQ ID NO.:15) which contain the T3 and T7 promoters, respectively, added to human CXCR-4 sequence corresponding to bases 1061-1087 and 1591-1618. Following hybridization, slides were washed in 50% formamide, 2×SSC pH; 4.5, 1% SDS at 50° C., treated with 5 µg/ml RNase A for 30 minutes at 37° C., and washed in 50% formamide, 2×SSC pH 4.5 at 50° C. Sections were pre blocked in 10% normal sheep serum (Sigma, St. Louis, Mo.) and incubated with a 1:2000 dilution of alkaline phosphatase conjugated anti-dioxigenin Fab fragments (Boehringer Mannheim) 18 hours at 4° C. For detection, slides were incubated with NBT/BCIP (5-Bromo-4-chloro-3-indilyl-phosphate, 4-toluidine salt) in the dark for 46 hours. After counter staining with eosin Y, slides were mounted with Permount and visualized using an Axioskop (Carl Zeiss, Thornwood, N.Y.) routine microscope.

Multiple Tissue Northern Blot Analysis

Multiple Normal Human tissue blots (MNHTB) were purchased from Clontech (Palo Alto, Calif.). These blots contained 2 µg of pure polyA+ mRNA. MNHTBs were prehybridized in express hybridization buffer solution (Clontech) for 3-4 hours. Hybridization was done with multiprime labeled 0.55 Kb (positions 1591-1618) CXCR-4 probe. Blots were washed in 0.1×SSC and 0.1% SDS solution for 60 minutes at 50° C. After autoradiographic exposure, the CXCR-4 probe was then removed, and the human β actin gene was used as internal control. Relative expression of CXCR-4 was calculated as described above.

Zoo Blot Analysis

A zoo blot membrane containing 5 µg of Predigested (EcoRI) genomic DNA was purchased from Clontech (Palo Alto, Calif.). The zoo blot was pre-hybridized according to the method recommended by Clontech (Palo Alto, Calif.). A 0.55 Kb (1061-1618) CXCR-4 fragment was labeled with dCTP$^{32}$ using decamer primer labeling kit from Ambion (Austin, Tex.) and was used as a probe for hybridization. Washing of the blot was performed as recommended by Clontech. To isolate the CXCR-4 0.557 Kb fragment for labeling as a probe, 125 ng of cDNA (prepared using oligo-dT and random hexamer primer from human neuroblastoma cell line) was used as a template. PCR amplification of CXCR-4 fragment was done using gene specific primers (5' CTCTC-CAAAGGAAAGCGAGGTGGACAT 3' (SEQ ID NO.:16) and 5' TGATTTCAGCACCTACAGTGTACAGTCT 3' (SEQ ID NO.:17) using the PCR conditions described previously (Sehgal et al., 1997 J. Surg. Oncol. 65:249-257, Sehgal et al., 1997 J. Surg. Oncol. 64: 102-108).

Cloning of the Full Length Clone for CXCR-4 Gene

A human fetal brain library (Stratagene, LaJolla, Calif.) was screened with a CXCR-4 specific 0.55 Kb PCR product (isolated from Neuroblastoma cell line using CXCR-4 specific PCR primers). Three positive clones were identified and single plaques were isolated after secondary screening of the library. To assess the insert size for these clones, PCR was performed using pfu Taq DNA Polymerase (Stratagene). PCR product was run on a 1.2% agarose gel. Sequence analysis indicated that clone #3 contained a 2.0 Kb insert and it is identical to the previously isolated full length CXCR-4 clone. To subclone the full length CXCR-4 gene into pCMV-neo, its coding region was PCR amplified with specific primers containing SacII and SpeI (underlined sites), (5' AGATAGAT CCGCGGACCATGGAGGGGATCAGTATATA 3' (SEQ ID No.:18), 5' TAGATACA ACTAGTGTGTTAGCTGGAGTGAAAACTTGA 3' (SEQ ID No.:19). The pCMV-neo vector then was digested with SacII and SpeI and ligated with CXCR-4 PCT product predigested with SacII and SpeI. To clone the CXCR-4 in the antisense direction, CXCR-4 specific primers (5' AGATA-GATCCGCGGGTGTTAGCTGGAGTGAAAACTTGA 3' (SEQ ID No.:20) and 5' TAGATACA ACTAGTACCATGGAGGGGATCAGTATATA 3' (SEQ ID No.:21) were used for carrying out the PCR and cloned into the predigested pCMV-neo vector in sense and antisense direction. Orientation of CXCR-4 gene was confirmed by sequencing.

Growth Assay

Growth assay of CXCR4 transfected cells was done using cell proliferation kit from Promega (Madison, Wis.) as described previously (Huang et al., 1995, Cancer Research 55:5054-5062). Briefly, 1000 cells for wild type and mutant expressing cells were plated in triplicate in a 96 well plate. Cells were incubated for 24 hours at 37° C. and 80 µl dye is added. After 4 hours, 15 µl of stop solution is added and incubated for 18 hours. Absorbance is then recorded at 570 nm using ELISA plate reader.

Soft agar assay was done as described previously (Huang et al., 1995, Cancer Research 55:5054-5062. Briefly, GB1690 cells that were transfected with vector alone and with CXCR-4 in sense direction were trypsinized. Approximately, $5 \times 10^6$ or $1 \times 10^6$ cell were mixed with 0.26% agar. Cells were then plated on top of a layer of 0.65% agar in 60 mm petri dishes and incubated 37° C. for 2-4 weeks. Cells were fed with serum containing media after every 10 days. Colonies were counted under the inverted light microscope.

Immunocytochemistry

Approximately $1 \times 10^4$ cells were plated in Lab Tek chamber slides (Nunc, Naperville Ill.). After 24 hours cells are washed in PBS. Cells were then covered with 4% paraformaldehyde (Sigma, St. Louis Mo.) and incubated at 4° C. for 2-4 hours. After washing cells in PBS again, 200 W of diluted (1:20) rabbit anti-human CXCR-4 antibody was applied to slides. CXCR-4 polyclonal antibody was prepared by Genemed Synthesis, Inc. (San Francisco, Calif.). This antibody was made against first 38 amino acids of the CXCR-4 protein (MEGISIYTSDNYTEEMGSGDYDSMKEPC-FREENANFNK (SEQ ID NO.:7). Slides were incubated for 18 hours at 4° C. in a humid chamber. After washing in PBS, FITC conjugated anti rabbit immunoglobulins (1:20) (DAKO, A/S, Denmark) were applied and the slides were incubated at 24° C. for 30 min in a humid chamber. Cells were washed with PBS and then stained with Hematoxylin (Richard Allen Scientific, Richland Mich.) for 30 seconds. Slides are then treated with a clarifying agent (Richard Allen Scientific, Richland Mich.) for 2 seconds and then in bluing agent (Richard Allen Scientific, Richland Mich.). After washing in water, slides are coverslipped with 2% DABCO (Sigma, St. Louis Mo.) in 50% glycerol/PBS, and visualized with a Zeiss Axioskop UV microscope.

6.2 Results

6.2.1. Identification of CXCR-4 Using the Technique of Differential Hybridization of Atlas™ Human cDNA arrays The major advantage of the technique of human cDNA arrays is that a large number of known or unknown genes can be analyzed for their altered expression under different biological conditions. The technique of differential hybridization of Atlas™ Human cDNA expression array was used to study the differences in gene expression between NBT and GMTT. Two Atlas™ Human cDNA expression array membranes were used (Clontech (Palo Alto, Calif.)), each membrane contained cDNA's from 588 known genes and 9 housekeeping genes. Equal amount cDNA from NBT and GMTT labeled with dCTP$^{32}$ was hybridized to two identical Atlas™ human cDNA microarrays. Several differentially expressed genes were identified in GMTT. One of these was the CXCR-4 gene that is over-expressed in GMTT as compared to NBT (FIGS. 1A & B). To confirm the differential expression of CXCR-4 in GMTT, the technique of gene specific RT-PCR was used. As shown in FIG. 3 (panels C and D), CXCR-4 is expressed at high levels in GMTT with low or no expression in NBT. Conditions for RT-PCR were decided after using different amounts of template and varying the number of PCR cycles.

6.2.2. Expression of CXCR-4 in GMTT

Figure 2B:

To further confirm the differential expression of CXCR-4 in GMTT, the technique of in situ hybridization was used to study the expression of CXCR-4 in eight different human GMTT. Four of the eight samples analyzed showed high levels of CXCR-4 expression. One such example is shown in FIG. 2. After identification of CXCR-4, the next step was understanding its function. To do so, its expression in a variety of tissues and cell types was examined.

Figure 3A:
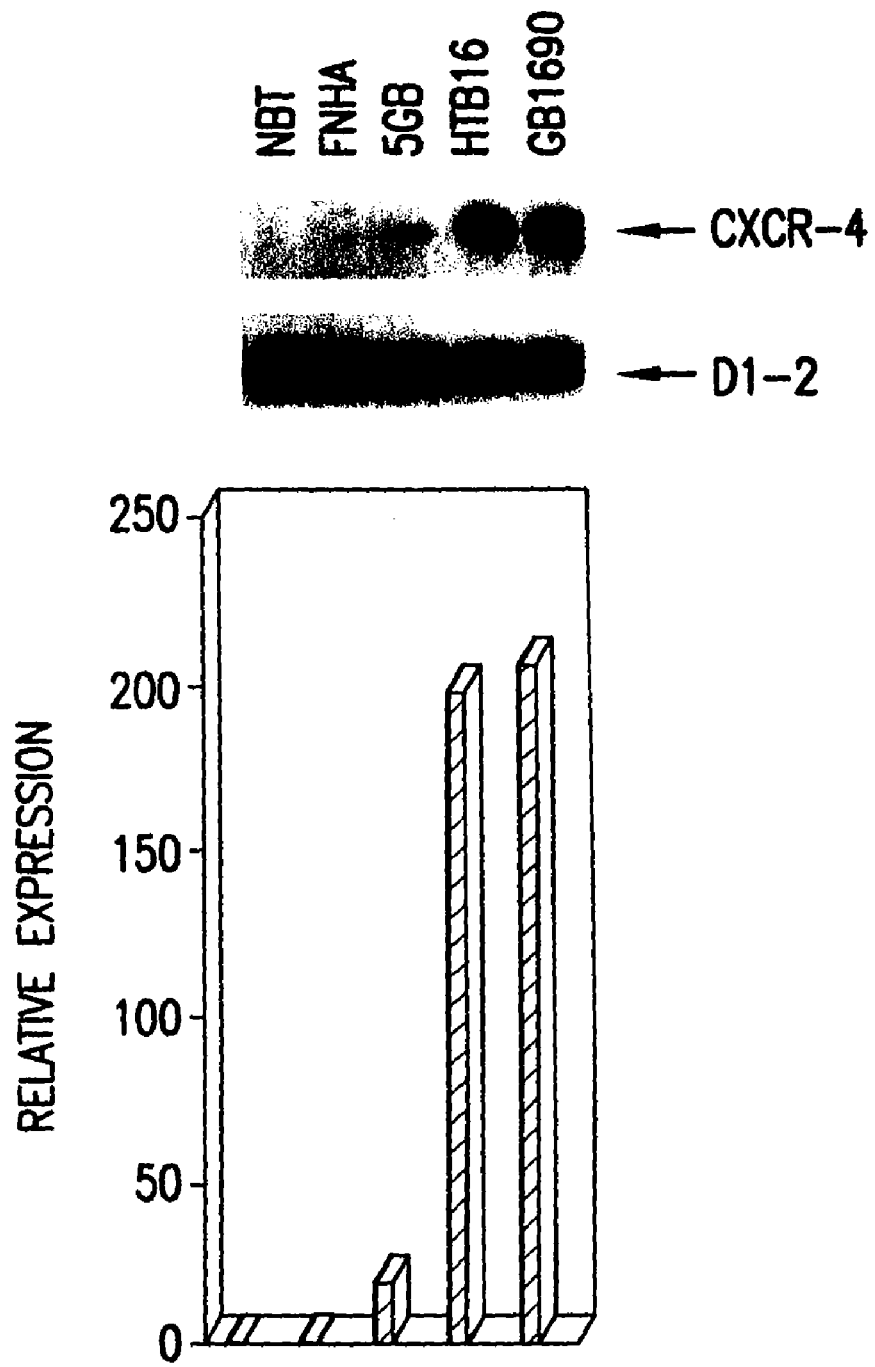
FIGS. 3A-C. Expression of CXCR-4 in human tumor cell lines and primary tissues. Gene specific RT-PCR was carried out using CXCR-4 and D1-2 specific primers. Panel A shows CXCR-4 expression in NBT, FNHA and three glioblastoma cell lines and tissues, respectively. Panels B and C show expression of CXCR-4 in brain tumor cell lines and tissues, respectively.
Figure 3B:
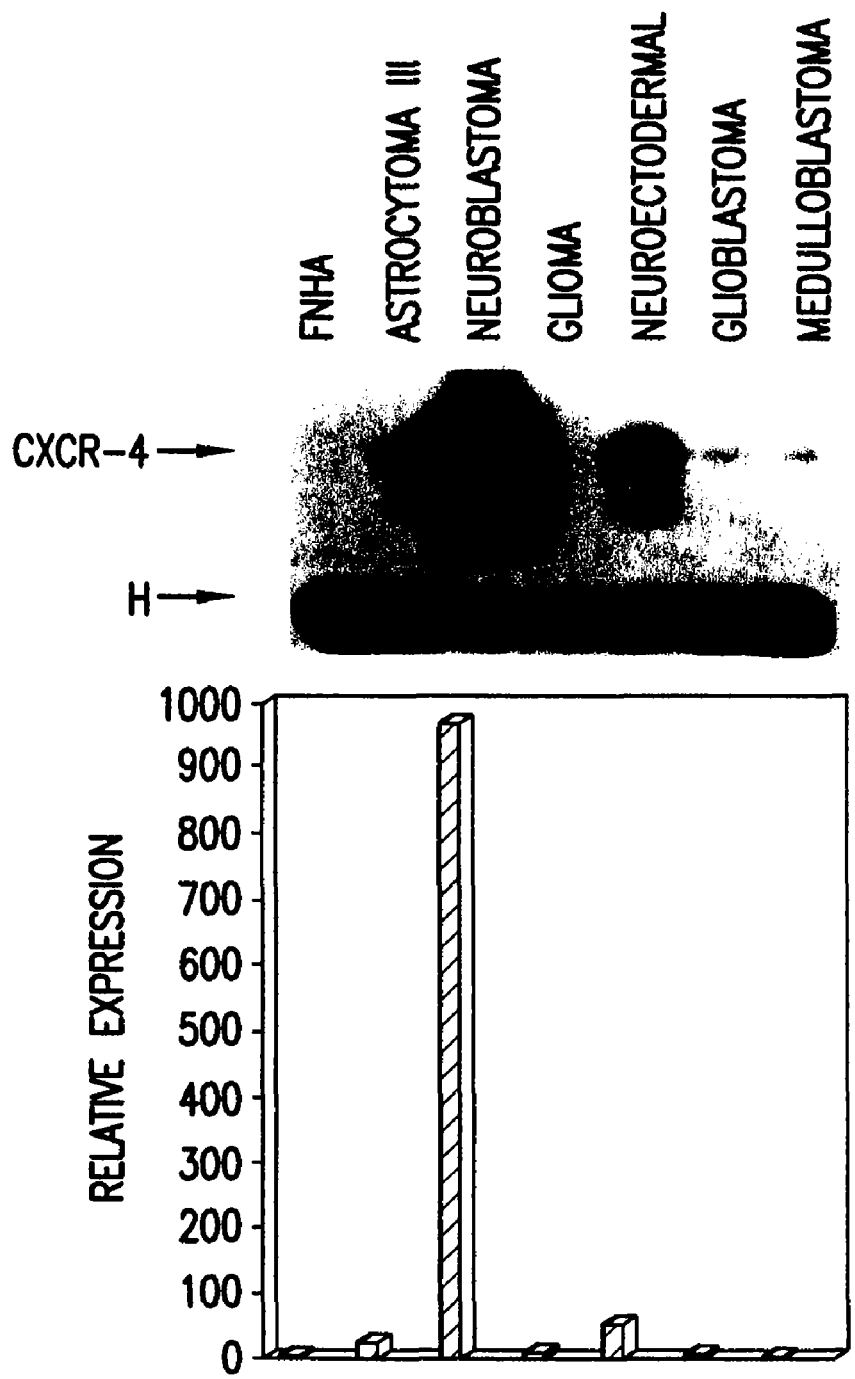
Figure 3C:
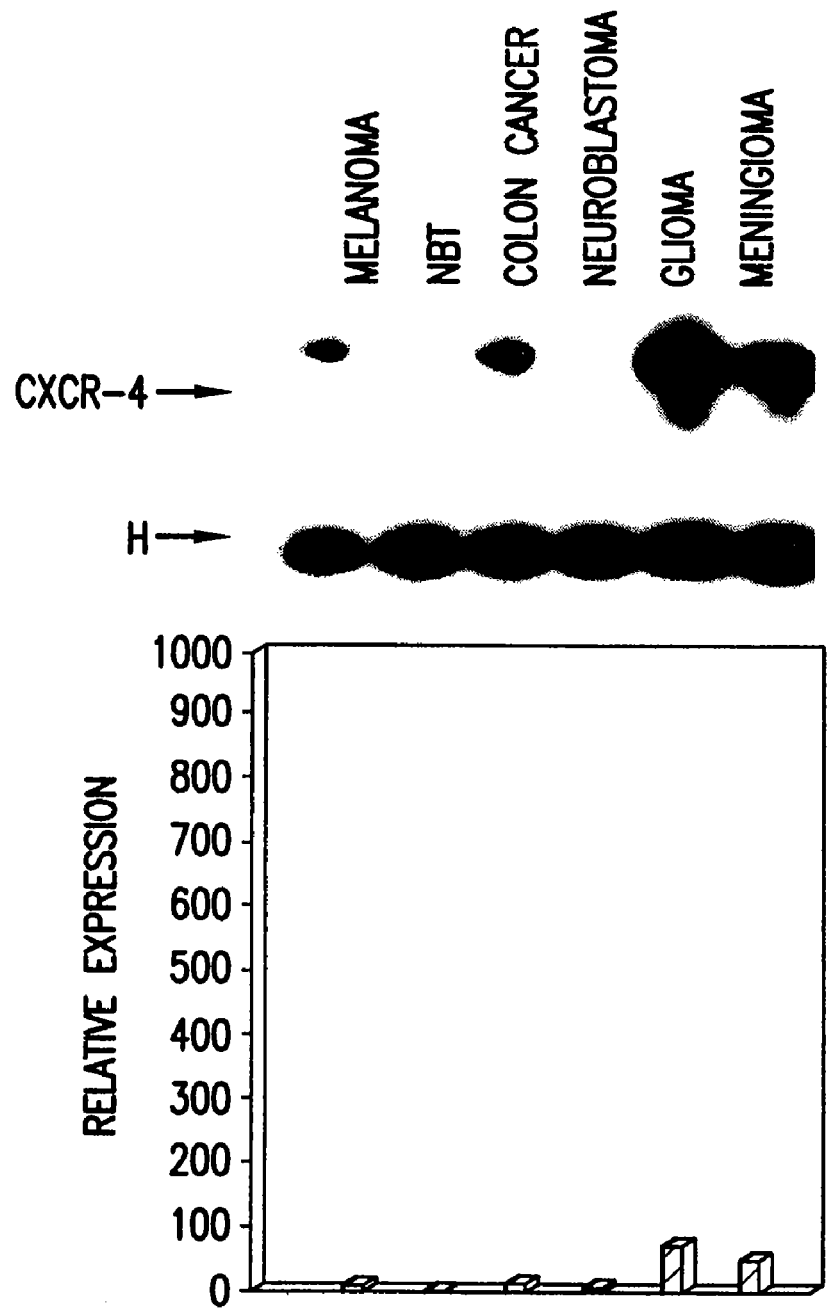

6.2.3. Expression of CXCR-4 in Glioblastoma and Other Brain Tumor Cell Lines and Tissues Since CXCR-4 is over expressed in glioblastoma multiforme tumor tissue, its expression in several brain tumor derived cell lines and primary brain tumor tissues was next studied. As shown in FIG. 3A, high levels of CXCR-4 expression is observed in several brain tumor derived cell lines and primary brain tumor tissues (see Table 2-below). As shown in FIG. 3A, high level of CXCR-4 expression is observed in three glioblastoma cell lines (5 GB, HTB-16 and GB1690) purchased from ATCC (Rockville, Md.). These three cell lines were originally derived from glioblastoma tumors of individual patients and are currently growing at different passage numbers (5 GB=15, HTB-16= and GB1690=425). RT-PCR analysis indicated that CXCR-4 is over-expressed in all three of these cell lines as compared to FNHA (Fetal Normal Human Astrocytes) and NBT. Glioblastoma cell lines HTB-16 and GB1690 showed CXCR-4 expression at a much higher level than the 5 GB cell line. Analysis of CXCR-4 in other cell lines have demonstrated that it is expressed at high levels in neuroblastoma and neuroectodermal human tumor cell lines. Moderate levels of expression of CXCR-4 are observed in medulloblastoma and astrocytoma grade III cell lines (FIG. 3B). In primary tissues, high levels of CXCR-4 expression are observed in glioma and meningioma tumors (FIG. 3C). On the basis of these results, it is concluded that CXCR-4 is over-expressed in human glioma tumors as compared to NBT. The ligand for CXCR-4, SDF-1, has recently been isolated and cloned. Therefore it was determined if this ligand is also over-expressed in brain tumor tissues and cell lines. SDF-1 was detected at very low levels in 5 GB cells but not in majority of the other cell lines. High levels of SDF-1 expression was observed in meningioma, malignant glioma, neuroblastoma tissue as compared to NBT.

6.2.4. Expression of CXCR-4 in Breast Tumor Primary Tissues and Cell Lines

Figure 4A:
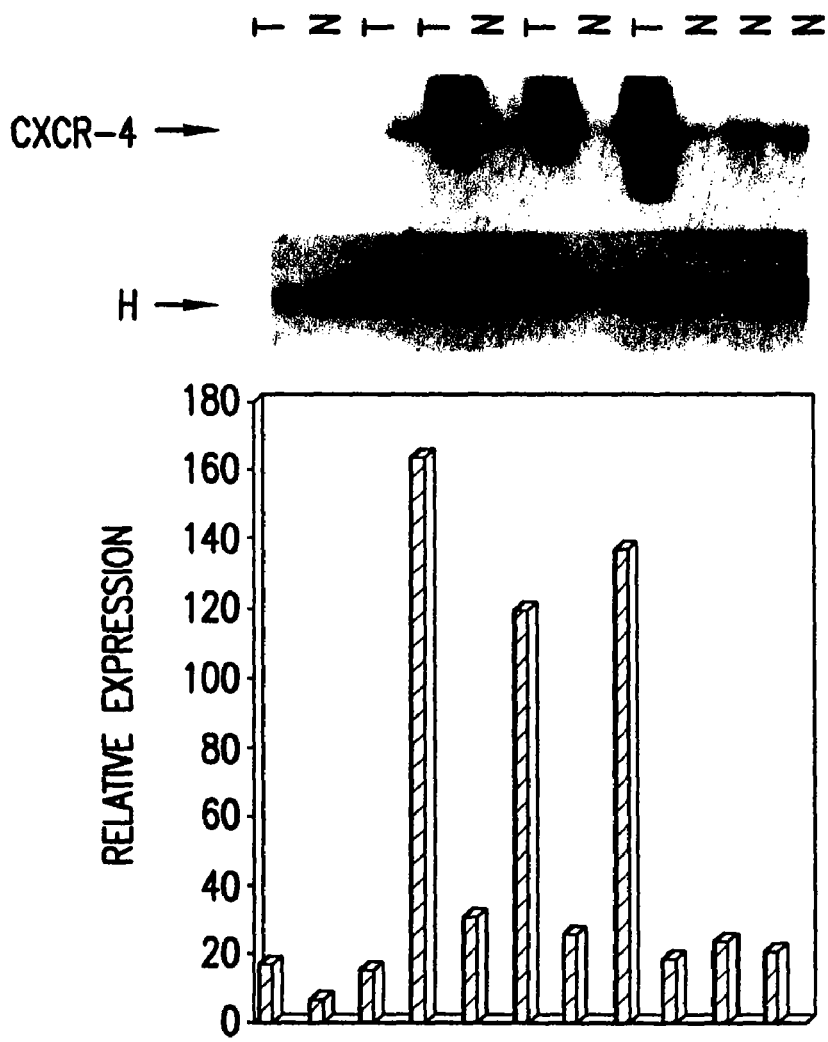
FIGS. 4A-B. Expression of CXCR-4 in breast tumor tissues and cell lines. Total RNA was isolated using the RNAzol solution from Gibco/BRL (Gaithersburg, Md.). After DNase 1 treatment, RT-PCR and Southern blotting was carried out.
Figure 4B:
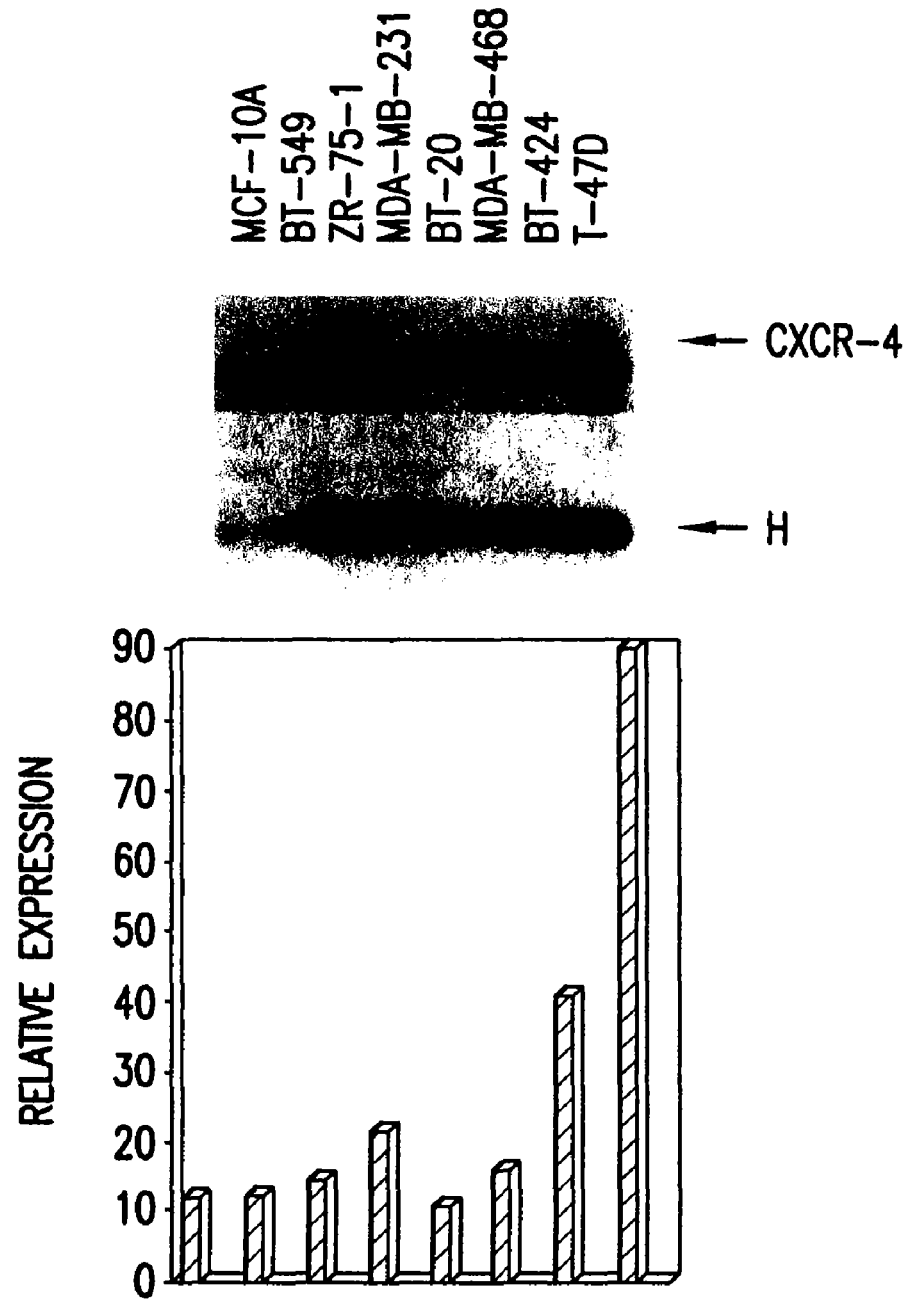

Since the CXCR-4 gene is over-expressed in brain tumor tissues and cell lines, the pattern of expression was tested in other tumor types and cell lines. The expression of CXCR-4 was tested in eleven primary breast tissues (5 tumors and 6 normal). As shown in FIG. 4A, CXCR-4 is expressed at high levels in three of the five breast tumor tissues studied and at low levels in six normal breast tissues (see Table 2 below). Two of the three breast tumor tissues that over express the CXCR-4 gene were estrogen and progesterone receptor positive and one was negative for both receptors. Expression analysis indicated that SDF-1 is also over-expressed in the same breast tissues that over-express CXCR-4. This may indicate that the role of CXCR-4 is ligand dependent. The expression of the CXCR-4 gene in one normal and seven breast tumor cell lines was determined next. As shown in FIG. 4B, high levels of CXCR-4 expression were observed in only one cell line, T-47D. Results from this experiment suggests that the CXCR-4 gene can play a role in the neoplastic transformation of normal breast tissue.

6.2.5. Expression of CXCR-4 in Cancer Cell Lines

Figure 5A:
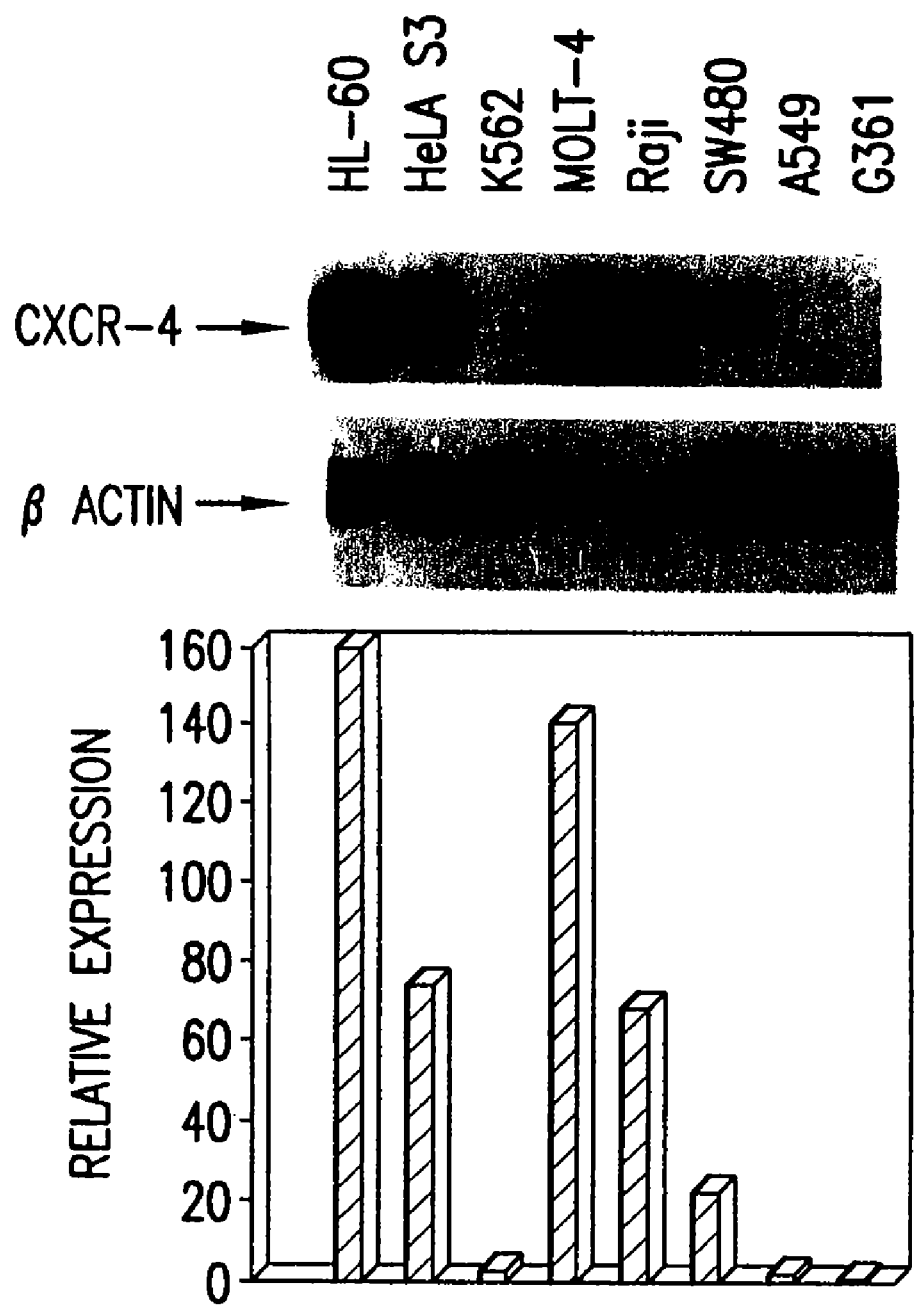
FIGS. 5A-B. Expression of CXCR-4 in cancer cell lines and normal tissues. To study the expression of CXCR-4 in human cancer cell lines (FIG. 5A) and normal Human tissues (FIG. 5B), a cancer cell line and three multiple normal Human tissue blots (MNHTB) were purchased from Clontech (Palo Alto, Calif.). These blots contained 2 µg of pure polyA+ mRNA. MNHTBs were prehybridized in express hybridization buffer solution (Clontech) for 3-4 hours. Hybridization was done with multiprime labeled 0.55 Kb (positions 1591-1618) CXCR-4 probe. The CXCR-4 probe was then removed, and the human β actin gene were used as internal control.

The results above demonstrate the CXCR-4 is over expressed in brain and breast tissues. Is CXCR-4 gene overexpressed in other tumor types? To address the question of whether CXCR-4 is over-expressed in other tumor types, its expression was studied in a variety of cancer cell lines using the technique of Northern blot analysis. As shown in FIG. 5A, high levels of CXCR-4 expression were observed in promyelocytic leukemia HL-60, HeLa cells S3, lymphoblastic leukemia MOLT-4, Burkitt's lymphoma Raji and low levels in colorectal adrenocarcinoma SW 480 (FIG. 5A). Low or no expression of CXCR-4 is observed in lung carcinoma A549, melanoma G361 and chronic myelogeneous Leukemia K-562. The data presented above clearly suggest that CXCR-4 is also over expressed in many tumor cell lines of lymphocytic origin.

6.2.6. Expression of CXCR-4 in Normal Human Tissues

Figure 5B:
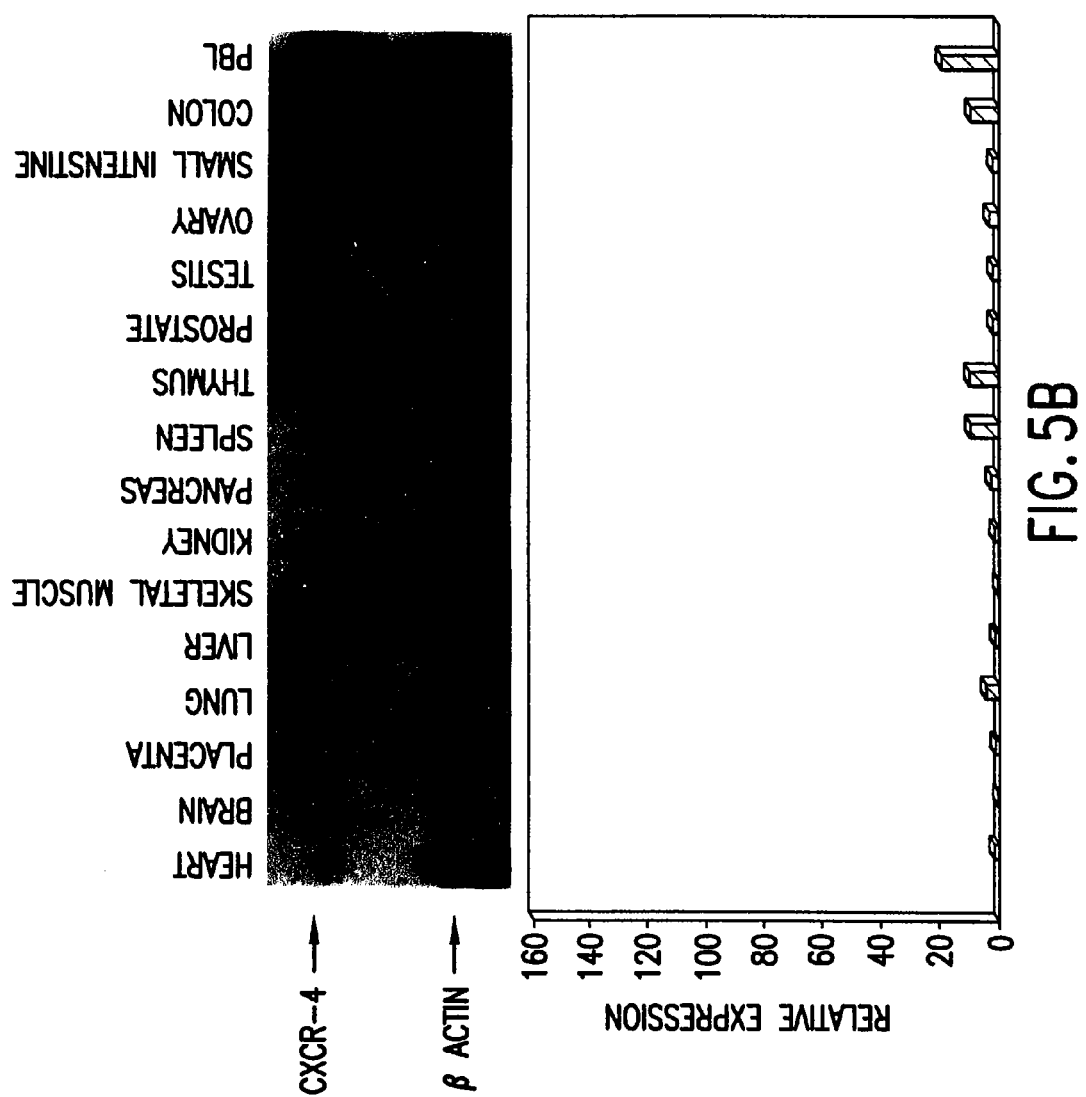

To begin to understand the role of the CXCR-4 gene in normal cell function, the expression of CXCR-4 gene in several normal human tissues was studied using the technique of Northern blot analysis. As shown in FIG. 5B, CXCR-4 is expressed in high levels in only four organs, (spleen, thymus, colon and PBLs). Low or no expression was observed in heart, brain, placenta, lung, liver, skeletal muscle, kidney, pancreas, prostate, testis, ovary and small intestine.

6.2.7 Expression of CXCR-4 in Different Regions of the Human Brain

Figure 6:
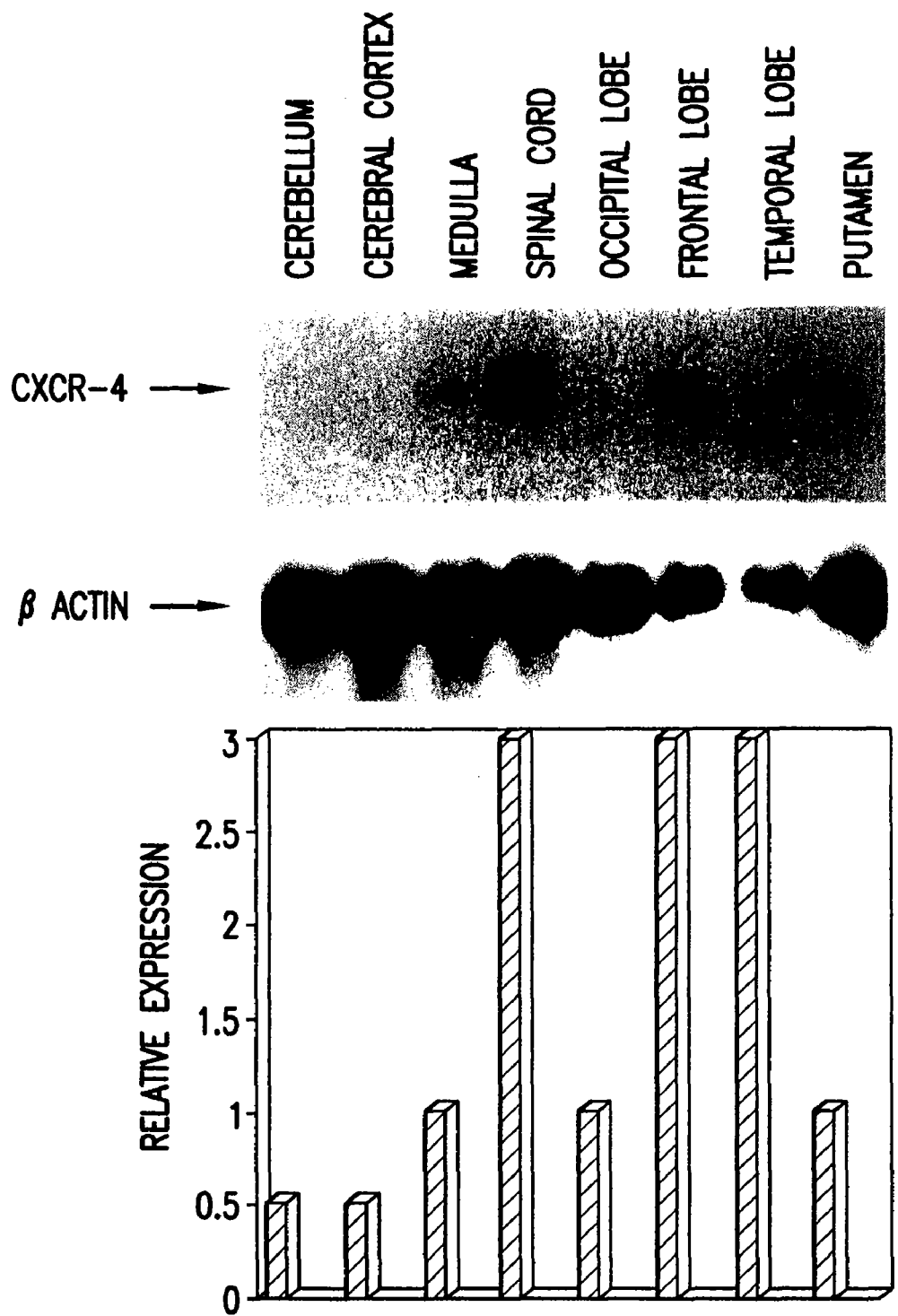
FIG. 6. Expression of CXCR-4 in different regions of the normal human brain. To study the expression of CXCR-4 in normal human, a normal human brain blot was purchased from Clontech (Palo Alto, Calif.). This blot contained 2 µg of polyA+ mRNA in each lane. Prehybridization of the blot was done in express hybridization buffer solution (Clontech) for 3-4 hours. Hybridization was done with multiprime labeled 0.55 Kb (positions 1591-1618) CXCR-4 probe. The CXCR-4 probe was then removed, and the human β actin gene was used as internal control. Relative expression of CXCR-4 was calculated as described previously (Sehgal et al., 1997 Int. J. Cancer 71:565).

The CXCR-4 gene was identified by its characteristic of being expressed at high levels in GMTT as compared to NBT. To begin to understand the role of CXCR-4, its expression was studied in different regions of the brain. As shown in FIG. 6, frontal lobe, temporal lobe and spinal cord express CXCR-4. Functional significance of such selective expression in these three areas of the brain is not known at present. Expression levels of CXCR-4 in these regions of the brain are lower than tissues of lymphocytic origin (compare relative expression units in FIGS. 5 and 6).

6.2.8. Expression of CXCR-4 During Development

Genes known to be up regulated during the process of tumorigenesis are also sometimes over-expressed during early stages of development. As a first step towards answering the question of whether CXCR-4 has a role during development, its expression during the early stages of mouse development was studied.

Figure 7A:
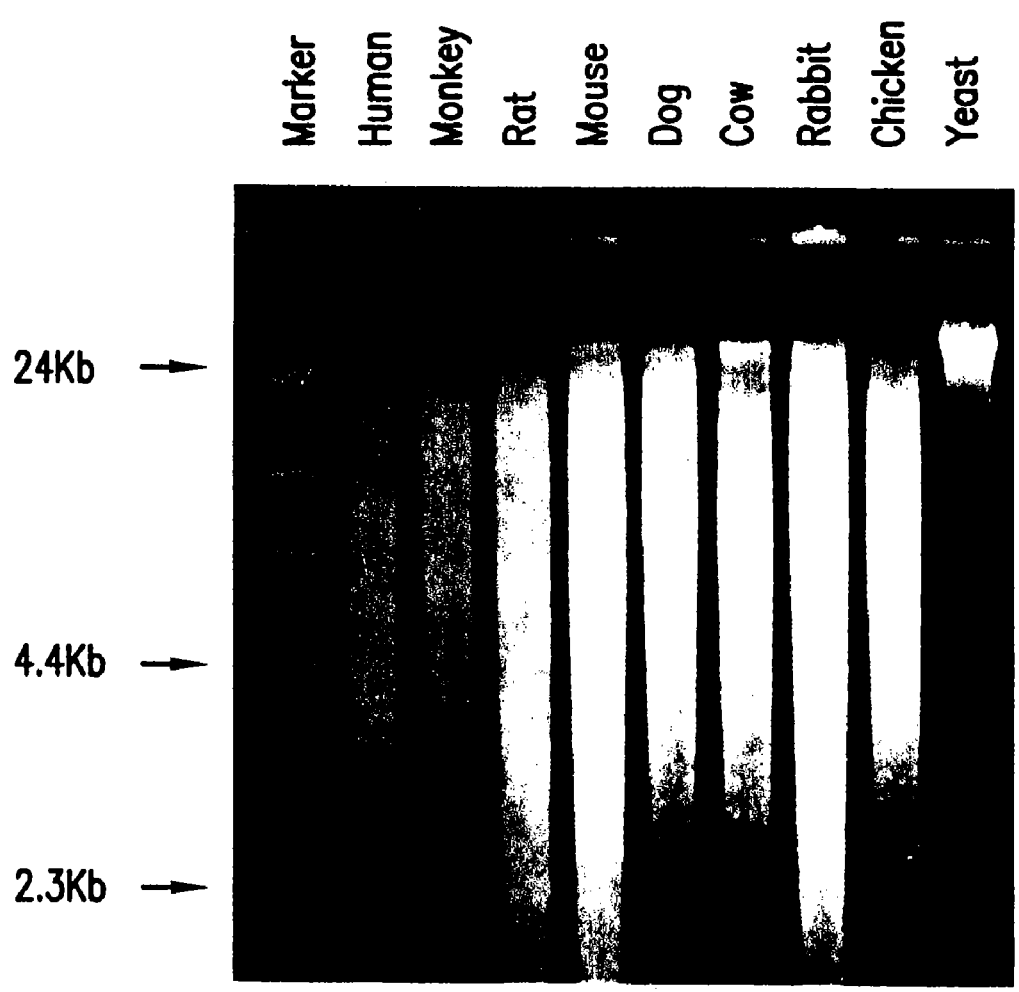
FIGS. 7A-B. Analysis of CXCR-4 sequence conservation in different animals. A zoo blot membrane containing 5 µg of predigested (EcoRI) genomic DNA was purchased from Clontech (Palo Alto, Calif.).
Figure 7B:
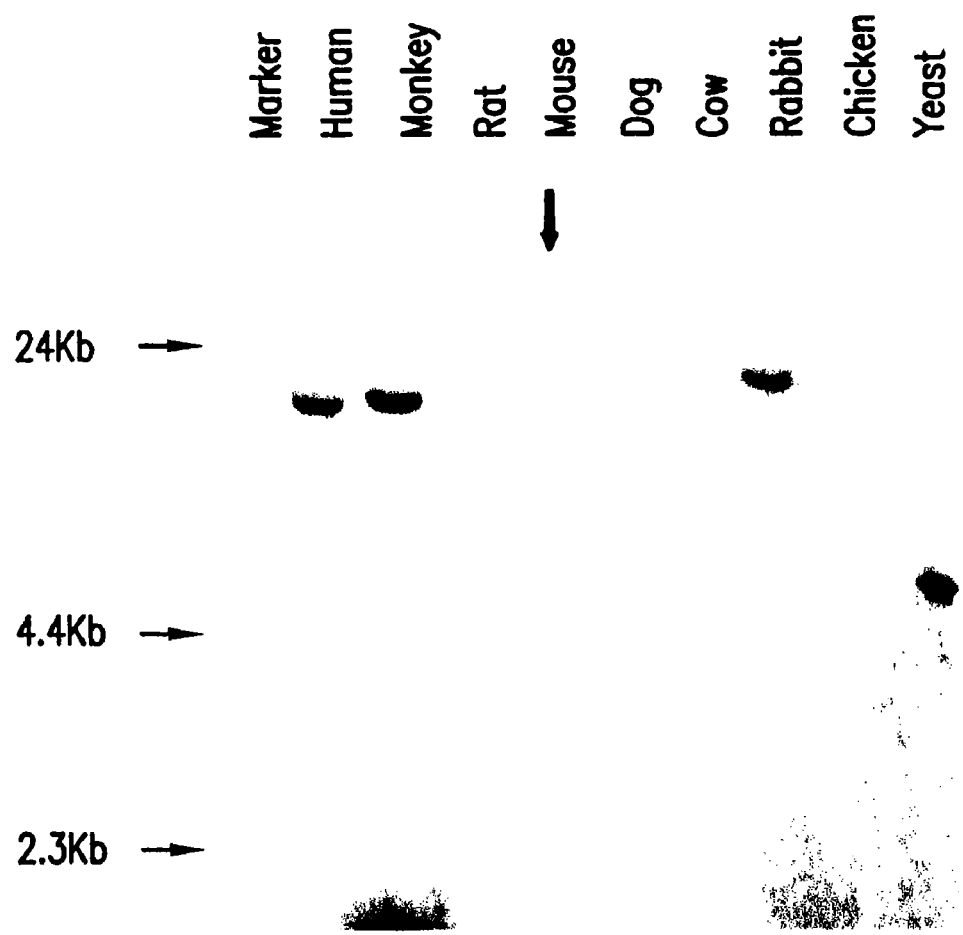
Figure 9B:
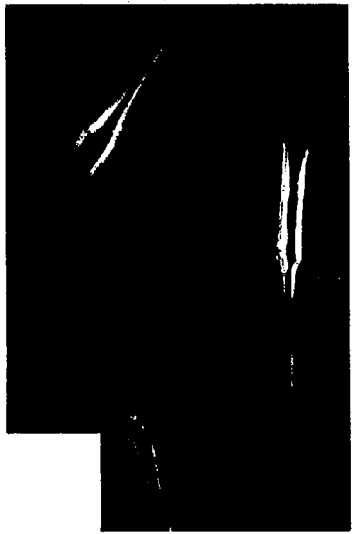
FIGS. 9A-D. Effect of CXCR-4 over-expression in 5 GB glioblastoma cell line.
Figure 9D:
Figure 9A:
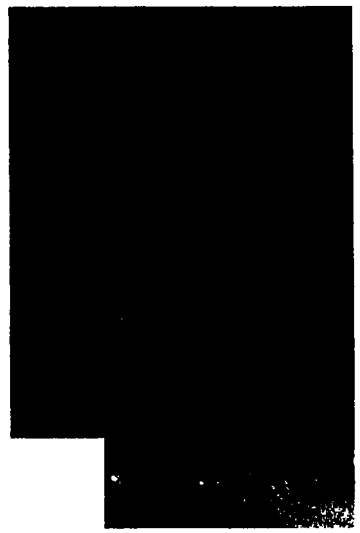
Figure 9C:
Figure 10A:
FIGS. 10A-C. Effect of CXCR-4 over-expression in GB1690 glioblastoma cell line.
Figure 10B:
Figure 10C:
Figure 11A:
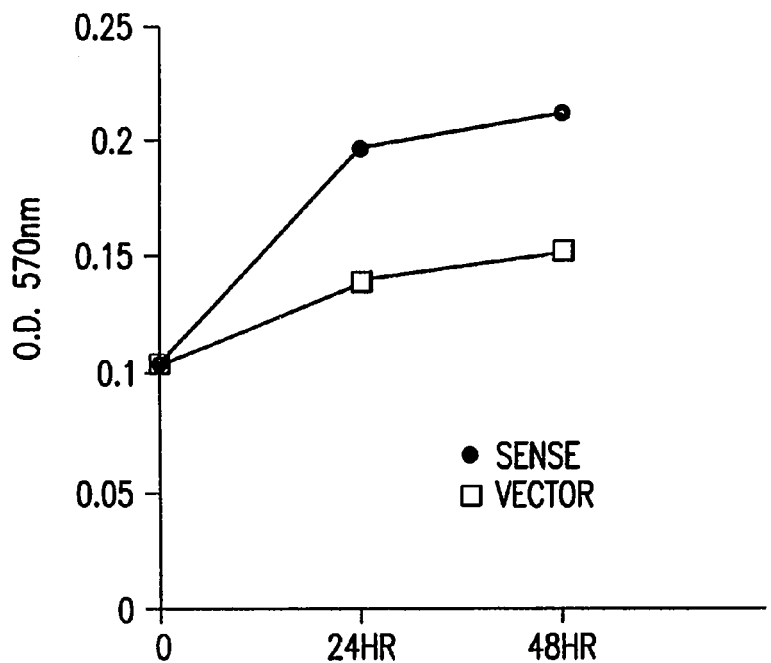
FIGS. 11A-B. Effect of CXCR-4 expression on GB1690 (FIG. 11B) and HTB-16 (FIG. 11A) glioblastoma cell lines. Briefly, 1000 cells for wild type and mutant expressing cells were plated in triplicates in a 96 well plate. Cells were incubated for 24 hours at 37° C. and 80 µl dye is added. After 4 hours, 15 µl of stop solution is added and incubated for 18 hours. Absorbance is then recorded at 570 nm using ELISA plate reader. Points in the graph represent average of two experiments done with triplicate samples.
Figure 11B:
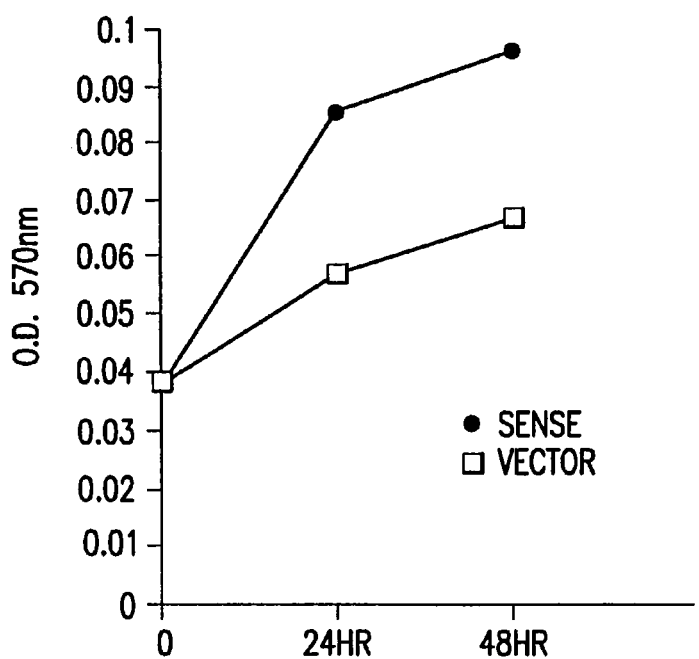

Before proceeding with the in situ hybridization of mouse embryos, we performed a zoo blot analysis to demonstrate that the sequence of CXCR-4 is conserved among human and mouse. As shown in FIG. 7, CXCR-4 is conserved among human, monkey, rat, mouse, dog, cow and chicken.

Eight developmental stages of mouse embryos (day 8 through day 16) were analyzed for CXCR-4 expression using the technique of in situ hybridization. CXCR-4 expression was observed in all tissues from day 8 through 12. By day 14, high levels of expression were observed in most of the tissues and all regions of the brain and bone marrow. By day 15, expression is very strong in the fore and mid brain and in pituitary. Low levels of expression were seen in the bone marrow, gut and ovary. By day 16, CXCR-4 expression was mainly confined to brain and bone marrow. These results demonstrate that CXCR-4 most likely has some important function during the early stages of development.

On the basis of data presented above it can be concluded that the CXCR-4 gene has some unique properties that are reflected by its differential expression not only in several primary tumor tissues and cell lines but also during embryonic development.

7. Example

Effect of Regulating CXCR-4 Expression in Glioblastoma Cell Lines

In order to asses the functional role of CXCR-4 in brain tumorigenesis the effects of over-expressing CXCR-4 and inhibiting both the activity and expression of CXCR-4 were examined in glioblastoma cell lines.

7.1 Materials and Methods
See Section 6.1.
7.2 Results 7.2.1. Expression of CXCR-4 Over-Expression in 5 GB Cell Line To study the role of the CXCR-4 gene in cell transformation, CXCR-4 was over-expressed in 5 GB cells in sense and anti-sense direction. Approximately 10 µg of pure DNA was transfected onto two 60 mm-diameter petri-dishes containing 10,000 cells using lipofectamine (Gibco/BRL). Transfected cells were selected in G418 (1000 µg/ml) for 2 weeks. After 3 weeks, cells were maintained in 400 µg/ml G418. Cell morphology was observed under the inverted light microscope and cell proliferation properties of transfected cell were analyzed using a non radioactive cell proliferation kit from Promega (Madison, Wis.). No change in cell growth and morphology was observed in glioblastoma cells transfected with pCMV-neo vector or CXCR-4 in sense direction (pCMV-neoCS) but cells transfected with CXCR-4 in anti-sense direction (pCMV-neoCA) showed extensive neurite out growth for the first two weeks (FIG. 9) followed by cell death after 5 weeks. Neurite out-growth is a unique characteristic of cells undergoing differentiation. Neurite out-growth and cell differentiation of neuroblastoma cells (LA-N-5HP) in response to retinoic acid (RA) and forskolin treatment has been observed (Moore et al., 1996 Clin Exp. Metastasis 14: 239-245). Recently, it was shown that treatment "of the glioblastoma cell line (5 GB) with sodium butyrate resulted in cell differentiation (Englehard et al., 1997 Neurosurgery 41: 886-897). Our results indicate that CXCR-4 over-expression in the antisense direction blocked CXCR-4 gene further in the 5 GB and GB 1690 glioblastoma cell line. This result strongly suggests that CXCR-4 expression is required for continuous proliferation of 5 GB cells.

7.2.2 Expression of CXCR-4 Over-Expression IN HTB16 and GB1690 Cell Line

Glioblastoma cell lines HTB16 and GB1690 express high levels of CXCR-4 as compared to NBT and the 5 GB cell line. These cell lines were transfected with vector alone or in sense direction (pCMV-neo, pCMV-neoCS). Even though no change in the cell morphology was observed, the rate of cellular proliferation was different. GB 1690 cells transfected with CXCR-4 in sense direction resulted in a rapid increase in cell proliferation as compared to cells transfected with vector only. This result was repeated when cells transfected with CXCR-4 in sense direction became confluent much faster than cells transfected with vector alone. These results demonstrate that over-expression of CXCR-4 in GB 1690 causes rapid proliferation of cells. When HTB16 cell were transfected with the CXCR-4 gene, similar results were obtained. Overall, cells transfected with CXCR-4 in sense direction proliferated at a rate 40% more than the vector alone transfected cells.

7.2.3 Soft Agar Colony Formation of CXCR-4 Over-Expressing GB1690 Cells

Figure 12E:
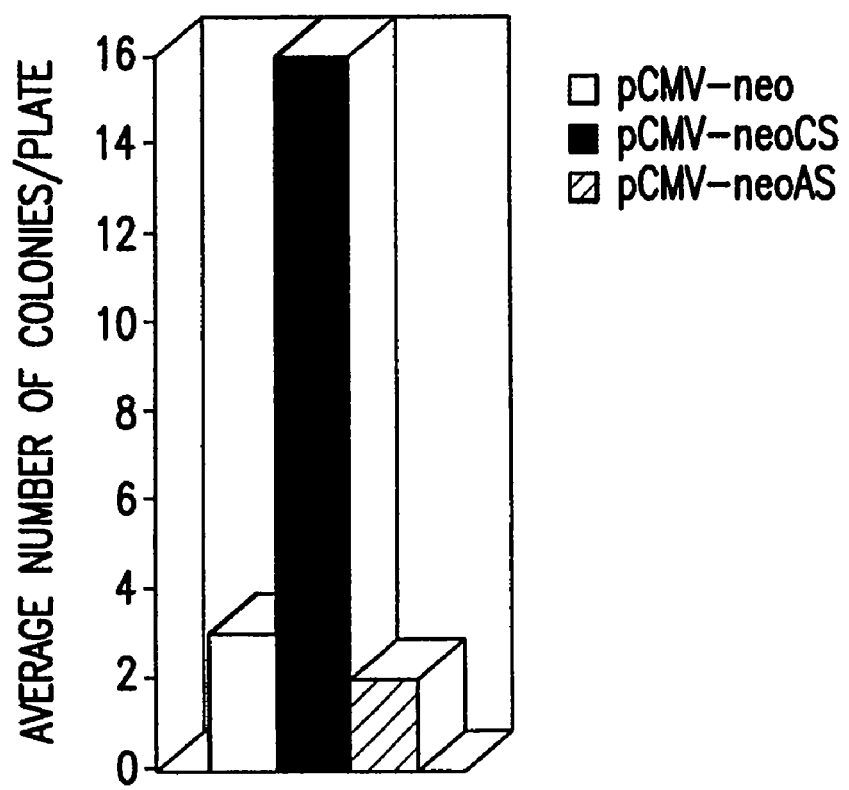

As is demonstrated above, the over-expression of CXCR-4 in HTB-16 and GB1690 cells resulted in rapid cellular proliferation in vitro. Does this alter certain phenotype in vitro? To address the question whether the over-expression of CXCR-4 would result in rapid cellular proliferation, soft agar colony formation assays were performed on GB 1690 cells that are over-expressing CXCR-4 in the sense direction. As shown in FIG. 12E, approximately 81% more colonies were formed in GB1690 cells over-expressing sense CXCR-4 gene as compared to same cells transfected with pCMV-neo vector alone. The colonies formed by the CXCR-4 over-expressing GB 1690 cells were significantly larger than those transfected with either vector alone. On the basis of this result, it is concluded that over-expression of CXCR-4 in GB1690 cells causes increase in their potential for cell transformation in vitro.

7.2.4. Effect of Inhibiting CXCR-4 and SDFβ-1

Figure 13:
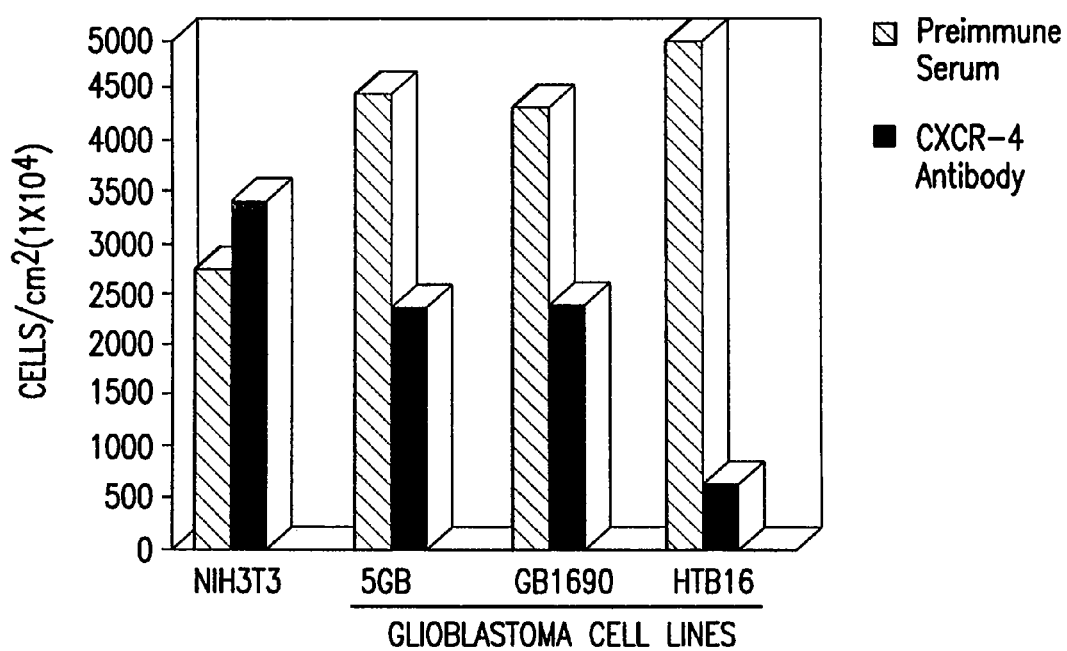
FIG. 13. Effect of CXCR-4 antibody treatment on tumor cell proliferation. A CXCR-4 polyclonal (rabbit anti-human) antibody was made against a synthetic peptide (MEGISIYTSDNYTEEMGSGDYDSMKEPC-FREENANFNK) (SEQ ID NO:7) corresponding to the first 38 amino acids of CXCR-4 protein. Approximately $1 \times 10^3$ cells (NIH3T3 and Glioblastoma) were plated in 60 mm petri dishes. 48 hours after plating, 1/50 final dilution of CXCR-4 polyclonal antibody or preimmune serum was added to the culture media. Cell were harvested after 192 hours and counted on cell counter. Results represent average of same experiment performed in triplicates.
Figure 16:
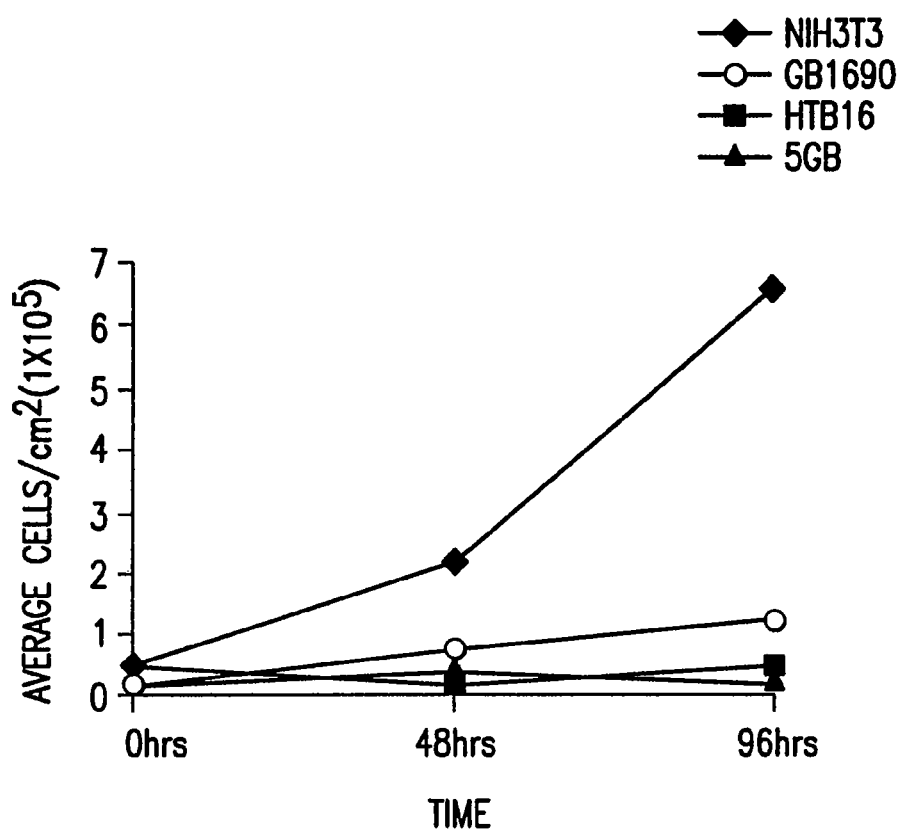
FIG. 16. Effect of SDF-1 antibody treatment on tumor cell proliferation. A monoclonal antibody against SDF-1 was purchased from R&D systems (Minneapolis, Minn.). Approximately $1 \times 10^3$ cells (NIH3T3 and Glioblastoma) were plated in 60 mm petri dishes. Twenty-four hours after plating anti-SDFβ-1 antibody or pre-immune serum was added to the culture media to a final concentration of 40 µg/ml. Cells were harvested every 48 hours and counted on a cell counter. Results represent average of same experiment performed in triplicates.

A role for CXCR-4 in cell proliferation was investigated first by transfecting and overexpressing a full length CXCR-4 cDNA into three different glioblastoma tumor cell lines. Enhanced proliferative activity was found in all three cell lines and the ability of the GB1690 cell line to form colonies in soft agar was greatly increased. To confirm the requirement of CXCR-4 and its ligand SDFβ-1, the effect of a specific antibodies on modulating proliferation of these cell lines was next studied (FIGS. 13 & 16). Specific CXCR-4 polyclonal antibodies or pre-immune serum were added to cultures 24 hours after plating and in two cell lines (GB1690 and 5 GB) cell proliferation was inhibited by 50% while in the third line, HTB-16, cell, proliferation was inhibited by 90% (FIG. 13). The effect, of SDFβ-1 monoclonal antibody on the proliferation of glioblastoma cell lines was next studied (FIG. 16). SDFβ-1 antibody caused approximately 90% inhibition of cell proliferation of three glioblastoma cell lines (5 GB, HTB-16, and GB1690). Conversely, treatment of NIH3T3 cells with SDFβ-1 antibody did not effect cell proliferation. Finally, CXCR-4 was inserted into the pCMV-neo vector in the sense and anti-sense direction and transfected into the 5 GB and GB1690 glioblastoma tumor cell lines. Within the first two weeks both cell lines transfected with the antisense CXCR-4 demonstrated extensive neurite outgrowth and cellular differentiation while cells transfected with sense CXCR-4 or vector only showed no changes in morphology (FIG. 9). Immunocytochemical analysis indicated that the glial cell differentiation cell marker, glial fibrillary associated protein (GFAP), was strongly induced in antisense transfected cells concomitant with the down regulation of CXCR-4 receptor protein expression). Neurite outgrowth is a typical characteristic of differentiating cells such as glioblastoma cells in response to sodium butyrate or neuroblastoma cells in response to retinoic acid (RA) and forskolin treatment. By three weeks after transfection and selection in G418, all cells transfected with the antisense CXCR-4 had undergone differentiation followed by cell death. Furthermore, cells transfected with the antisense CXCR-4 were unable to form colonies in soft agar (FIG. 12). Thus, inhibition of the cellular function of CXCR-4 by blocking its protein expression clearly demonstrates a role in the mechanism(s) regulating proliferative activity of these glioblastoma tumors and possibly other tumor types such as breast adenocarcinoma. These results also indicate that both CXCR-4 and its ligand SDF-1 are required for glioblastoma cell proliferation.

The over expression of the CXCR-4 receptor in glioblastoma and breast adenocarcinoma cancer is a surprising finding in light of the defined role of CXCR-4 in the entry of HIV into CD4+ cells. These observations coupled with the additional finding reported here that antisense inhibition of CXCR-4 receptor expression induces cellular differentiation supports a functional role for the CXCR-4 receptor in the maintenance of the neoplastic phenotype. Moreover, the concomitant expression of the CXCR-4 ligand SDF-1 by these cancers suggests an autocrine/paracrine role in the genesis of aberrant proliferative behavior of these cancers.

TABLE 2

Overexpression* of CXCR-4 in primary tissues and cell lines.

| Tumor Type | Source | # of Tissues with CXCR-4 overexpression/Total # of tissues analyzed |
| --- | --- | --- |
| Brain Tumors | Primary Tissue | 11/19 |
| | Cell Lines | 8/9 |
| Normal Brain | Primary Tissue | 0/10 |
| Breast Tumors | Primary Tissue | 3/5 |
| | Cell Lines | 3/7 |
| Normal Breast | Primary Tissue | 0/6 |

*Overexpression is more than two fold and is determined using RT-PCR Southern blots and In Situ hybridization.

Table 2. Overexpression of CXCR-4 in primary tumor and normal tissues and cell lines. Gene specific RT-PCR and Southern blotting was carried out using CXCR-4 and D1-2 specific primers for studying expression in brain and breast primary tissue and cell lines. RT-PCR and Southern blot was performed using methodology described above. To study the expression of CXCR-4 in human cancer cell lines, a cancer cell line and three multiple normal Human tissue blots (MNHTB) were purchased from Clontech (Palo Alto, Calif.). These blots contained 2 mg of pure polyA+ mRNA. Hybridization was done with multiprime labeled 0.55 Kb (positions 1591-1618) CXCR-4 probe. The CXCR-4 probe was then removed, and the human β actin gene used as internal control. Quantification of Southern and Northern blots was performed using the ImageQuaNT™ volume quantitation program from the Molecular Dynamics Phosphor Imager. Volume quantitation calculates the volume under the surface created by a 3-D plot of pixel locations and pixel values. The volume (the integrated intensity of all the pixels in the spot excluding the background) of CXCR-4 bands in Southern blots was quantitated. These pixel values are then normalized with pixel values in the bands of the housekeeping gene (D1-2 or β actin) and are shown as relative expression. Experiments were carried out twice and a two-fold or greater CXCR-4 expression in tumor compared to NBT was considered as over expression. Eight of the nineteen human brain glioblastoma surgical tissues were analyzed using the technique of in situ hybridization.

8. Example

Antisense Oligonucleotides to Inhibit CXCR-4 Expression

According to the present invention, antisense phosphorothioate oligonucleotides can be developed to inhibit the expression of CXCR-4. Briefly, six phosphorothioate oligodeoxynucleotides (ODN) against the translational initiation site and three random ODNs can be purchased from a commercial supplies, e.g., Oliogos Etc. Inc. (Wilsonville, Oreg.). The effect of ODNs on CXCR-4 expression inhibition is performed using the methodology described previously (Broaddus. et al., 1997, Neurosurgery 42:905-915). Briefly, 1000, HTB-16 and GB1690 cells are plated per well in 96-well plates in media without ODNs. Twenty four hours later, the culture media is changed to contain final concentration of 1 mmole/L, 3 mmol/L, or 10 mmol/L ODNs. Control cultures receive fresh culture media without added ODNs. After 4-5 days, cell proliferation is analyzed using cell proliferation assay kit from Promega (Madison, Wis.). To study effect of ODNs on CXCR-4 expression, HTB-16 and GB1690 cells are plated on glass chamber slides. Expression is analyzed using immunocytochemistry methods described above. Once the concentration of ODNs needed to inhibit the expression of CXCR-4 has been determined, RT-PCR, Northern and Western blot analysis are performed on cells treated with ODNs. Growth curves and soft agar colony formation are analyzed for cells that over-express and under-express the CXCR-4 gene.

ILLUSTRATIVE EXAMPLES OF
ANTISENSE OLIGONUCLEOTIDES WHICH CAN BE
USED IN ACCORDANCE WITH THE PRESENT INVENTION

5'GCCACCGCATCTGGAGAACCA    CXCR-4  (SEQ ID NO: 22)
GCGGTTACCATGGAGGGGATCCA
GTATATACACTTCAGAT3'

3'CGGTGGCGTAGACCTCTTGG5'   OL-1    (SEQ ID NO: 23)

3'CCAATGGTACCTCCCCTAG5'    OL-2    (SEQ ID NO: 24)

3'GGTCATATATGTGAAGTCTA5'   OL-3    (SEQ ID NO: 25)

5'ACTAGAGATACAGATCATAT3'   OL-4    (SEQ ID NO: 26)

5'CATATACGATCGATCGATGC3'           (SEQ ID NO: 27)

5'GATAGTGCTGATCGATGCTA3'           (SEQ ID NO: 28)

The present invention is not to be limited in scope by the microorganism deposited or the specific embodiments described herein. Indeed, various modifications of the invention in addition to those described herein will become apparent to those skilled in the art from the foregoing description

What is claimed is:

1. A method of inhibiting the proliferation of a cell within a brain tumor, neuroblastoma or breast tumor that over-expresses SDF-1 (SEQ ID NO: 4) in a subject comprising administering to the subject in which such treatment is desired a therapeutically effective amount of an antibody that specifically binds to SDF-1 (SEQ ID NO:4) and that inhibits SDF-1 binding to CXCR-4 on the tumor cell.

2. The method of claim 1 in which the cell that over-expresses SDF-1 (SEQ ID NO: 4) is malignant.

3. The method of claim 1 in which the subject is a human.

4. The method of claim 1 in which the cell that over-expresses SDF-1 (SEQ ID NO: 4) is within the brain tumor selected from meningioma, or malignant glioma and wherein the administration is into the central nervous system.

5. The method of claim 4 in which the glioma is glioblastoma multiforme.

6. The method of claim 1 in which the antibody is a polyclonal antibody or a monoclonal antibody or antigen binding fragment thereof.

7. The method of claim 1, wherein the antibody is a chimeric antibody, a single chain antibody, a Fab', a F(ab')$_2$ or a Fab fragment.

8. The method of claim 1, wherein the antibody is a bispecific antibody.

9. The method of claim 1, wherein the antibody is conjugated with a label or therapeutic moiety.

10. The method of claim 9, wherein the label or therapeutic moiety is a radioactive metal ion, a toxin, or a drug.

* * * * *